(12) United States Patent
Szeto et al.

(10) Patent No.: US 8,592,373 B2
(45) Date of Patent: *Nov. 26, 2013

(54) METHODS FOR PREVENTION AND TREATMENT OF ACUTE RENAL INJURY

(75) Inventors: Hazel H. Szeto, New York, NY (US); Diane Felsen, Brooklyn, NY (US)

(73) Assignee: Cornell University, Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/402,620

(22) Filed: Feb. 22, 2012

(65) Prior Publication Data

US 2013/0017150 A1    Jan. 17, 2013

Related U.S. Application Data

(63) Continuation of application No. 12/392,565, filed on Feb. 25, 2009, now Pat. No. 8,143,219.

(60) Provisional application No. 61/031,585, filed on Feb. 26, 2008.

(51) Int. Cl.
    *A61K 38/00* (2006.01)
    *A61K 38/06* (2006.01)
    *A61K 38/07* (2006.01)
    *A61P 13/12* (2006.01)

(52) U.S. Cl.
    USPC ........................... 514/15.4; 514/21.9

(58) Field of Classification Search
    None
    See application file for complete search history.

(56) References Cited

U.S. PATENT DOCUMENTS

| | | | |
|---|---|---|---|
| 4,522,811 A | 6/1985 | Eppstein et al. | |
| 5,312,899 A | 5/1994 | Schiller | |
| 5,602,100 A | 2/1997 | Brown et al. | |
| 5,652,122 A | 7/1997 | Frankel et al. | |
| 5,663,296 A | 9/1997 | Doherty et al. | |
| 5,674,534 A | 10/1997 | Zale et al. | |
| 5,716,644 A | 2/1998 | Zale et al. | |
| 5,885,958 A | 3/1999 | Zadina et al. | |
| 5,993,848 A | 11/1999 | Suzuki et al. | |
| 5,994,372 A | 11/1999 | Yaksh | |
| 6,221,355 B1 | 4/2001 | Dowdy | |
| 6,268,398 B1 | 7/2001 | Ghosh et al. | |
| 6,468,798 B1 | 10/2002 | Debs et al. | |
| 6,503,713 B1 | 1/2003 | Rana | |
| 6,703,483 B1 | 3/2004 | Schiller | |
| 6,759,520 B1 | 7/2004 | Carr et al. | |
| 6,900,178 B2 | 5/2005 | Oeltgen et al. | |
| 7,498,297 B2 | 3/2009 | Szeto et al. | |
| 7,541,340 B2 * | 6/2009 | Szeto et al. | 514/1.1 |
| 7,550,439 B2 * | 6/2009 | Szeto | 514/1.1 |
| 7,718,620 B2 | 5/2010 | Szeto et al. | |
| 7,781,405 B2 | 8/2010 | Szeto | |
| 7,811,987 B2 | 10/2010 | Szeto et al. | |
| 8,143,219 B2 * | 3/2012 | Szeto et al. | 514/15.4 |
| 2004/0248808 A1 | 12/2004 | Szeto et al. | |
| 2005/0096333 A1 | 5/2005 | Dugar et al. | |
| 2005/0158373 A1 | 7/2005 | Szeto et al. | |
| 2005/0192215 A1 | 9/2005 | Ghosh et al. | |
| 2006/0084606 A1 | 4/2006 | Szeto | |
| 2007/0015711 A1 | 1/2007 | Szeto | |
| 2007/0027070 A1 | 2/2007 | Szeto | |
| 2007/0027087 A1 | 2/2007 | Szeto et al. | |
| 2007/0093969 A1 | 4/2007 | Mendrick et al. | |
| 2007/0129306 A1 | 6/2007 | Szeto et al. | |
| 2008/0014604 A1 | 1/2008 | Devarajan et al. | |
| 2008/0027082 A1 | 1/2008 | Hocher et al. | |

FOREIGN PATENT DOCUMENTS

| | | |
|---|---|---|
| CA | 2361364 | 9/2000 |
| WO | WO 95/22557 | 8/1995 |
| WO | WO-96/40073 | 12/1996 |
| WO | WO-99/15154 | 4/1999 |
| WO | WO-00/38651 | 7/2000 |
| WO | WO 00/55189 | 9/2000 |
| WO | WO 02/05748 | 1/2002 |
| WO | WO 2004/070054 | 8/2004 |
| WO | WO 2005/001023 | 1/2005 |
| WO | WO 2005/072295 | 8/2005 |
| WO | WO 2007/035640 | 3/2007 |

OTHER PUBLICATIONS

Morcos, S.K., Ureteric obstruction and intravascular administration of contrast media: is there a risk? The British Journal of Radiology. 2003. vol. 76, pp. 564-565.*

Azzouz, Mimoun, Gene therapy for ALS: progress and prospects, *Biochemical et Biophysica Acta*, 1762:1122-1127, 2006.

Berendsen, Herman, A glimpse of the holy grail?, *Science*, 282:642-643, Oct. 23, 1998.

Bickel et al., Synthesis and bioactivity of monobiotinylated DALDA: A *Mu*-specific opioid peptide designed for targeted brain delivery. *J Pharmacol and Exp Therapeutics* 268(2): 791-196 (1994).

Bork et al., Go hunting in sequence databases but watch out for the traps, *Trends in Genetics*, 12:425-427, 1996.

Bork, Powers and pitfalls in sequence analysis: the 70% hurdle, *Genome Research*, 10:398-400, 2000.

Bradley et al., Limits of cooperativity in a structurally modular protein: response of the notch ankyrin domain to analogous alanine substitutions in each repeat, *J. Mol. Biol.*, 324:373-386, 2002.

Brenner, Errors in genome annotation, *Trends in Genetics*, 15:132-133, 1999.

Broekemeier et al., Inhibition of the mitochondrial permeability transition by Cyclosporin A during long time frame experiments: relationship between pore opening and the activity of mitochondrial phospholipases, *Biochemistry*, 34:16440-16449, 1995.

Cho et al., A novel cell-permeable antioxidant peptide, SS31, attenuates ischemic brain injury by down-regulating CD36. *J Biol Chem* 282(7): 4634-4642, 2007.

Cho et al., Potent mitochondria-targeted peptides reduce myocardial infarction in rats, *Coron Artery Dis.*, 18(3):215-220, May 2007.

(Continued)

*Primary Examiner* — Marcela M Cordero Garcia
(74) *Attorney, Agent, or Firm* — Foley & Lardner LLP

(57) ABSTRACT

The disclosure relates to a method for protecting a kidney from renal injury. For example, acute renal injury may be associated with decreased or blocked blood flow in the subject's kidney or exposure to a nephrotoxic agent, such as a radiocontrast dye. The methods include administering to the subject an effective amount of an aromatic-cationic peptide to a subject in need thereof.

8 Claims, 30 Drawing Sheets

(56) References Cited

OTHER PUBLICATIONS

Citron, Martin, Alzheimer's Disease: Treatments in discovery and development, *Nature Neuroscience Supplement*, 5:1055-1057, Nov. 2002.

Clapp III et al., Cardiovascular and metabolic responses to two receptor-selective opioid agonists in pregnant sheep, *American Journal of Obstetrics and Gynecology*, 178(2):397-401, Feb. 1998.

Demas, et al., Anaesthesia for heart transplantation, *Br J. Anaesth*, 58:1357-1564, 1986.

Dimaio et al., Synthesis and pharmacological characterization in vitro of cyclic enkephalin analogues, Effect of Conformational Constraints on Opiate Receptor Selectivity, *J. Med. Chem.*, 25:1432-1438, 1982.

Doerks et al., Protein annotation: detective work for function prediction, *Trends in Genetics*, 14:248-250, 1998.

Dooley, C T et al., Selective ligands for the mu, delta and kappa opioid receptors identified from a single mixture based tetrapeptide positional scanning combinatorial library, *Journal of Biological Chemistry, American Society of Biochemistry and Molecular Biology*, 273(30):18848-18856, Jul. 24, 1998.

Drin et al., Studies on the internalization mechanism of cationic cell-penetrating peptides, *Journal of Biological Chemistry*, 278(33):31192-31201, 2003.

Fuhrman et al., Oxidative stress increases the expression of the CD36 scavenger receptor and the cellular uptake of oxidized low-density lipoprotein in macrophages from atherosclerotic mice: protective role of antioxidants and of paraoxonase, *Atherosclerosis*, 161(2):307-316, Mar. 7, 2002.

Guerrini et al., Opioid receptor selectivity alteration by single residue replacement: synthesis and activity profile of [Dmt] deltorphin B, *European Journal of Pharmacology*, 302:37-42, 1996 (abstract only.).

Han et al., Mitochondria-derived reactive species mediate heme oxygenase-1 expression in sheared endothelial cells, *J Pharmacol Exp Ther.*, 329(1):94-101, Jan. 8, 2009 (epublished).

Herve et al., On the immunogenic properties of retro-inverso peptides. Total retro-inversion of t-cell epitopes causes a loss of binding to MHC II molecules, *Molecular Immunology*, 34(2):157-163, 1997.

Holsey et al., Cardiovascular effects of a μ-selective opioid agonist (Tyrosine-D-Arginine-Phenylalanine-Lysine-NH$_2$) in fetal sheep; Sites and Mechanisms of Action, *Am. J. Obstet. Gynecol.*, 180(5):1127-1130, May 1999.

Kett et al., Baroreflex-mediated bradycardia but not tachycardia is blunted peripherally by intravenous μ-opioid agonists, *Am. J. Obstet. Gynecol.*, 178(5):950-955, May 1998.

Korczyn et al., Emerging therapies in the pharmacological treatment of Parkinson's Disease, *Drugs*, 62(5):775-786, 2002.

Lasukova et al., Activation of mu-opioid receptors and cardiomyocyte resistance to free radical damage, *Patol Fiziol Eksp Ter.*, 2: English Abstract Only, 2001.

Lishmanov et al., Ligands for opioid and o-receptors improve cardiac electrical stability in rat models of post-infarction cardiosclerosis and stress, *Life Sciences*, 65:13-17, 1999.

Majer et al., Synthesis of methylated phenylalanines via hydrogenolysis of corresponding 1, 2, 3, 4 tetrahydroisoquinoline-3-caraboxylic acids, *Int. Journal of Peptide & Protein Research*, 43:62-68, 1994.

Margolis et al., Diagnosis of Huntington Disease, *Clinical Chemistry*, 49(10):1726-1732, 2003.

Mizuguchi et al., A novel cell-permeable antioxidant peptide decreases renal tubular apoptosis and damage in unilateral ureteral obstruction, *Am J Physiol Renal Physiol.*, 295(5):F1545-1553, Sep. 10, 2008 (epublished).

Moosman et al. Secretory peptide hormones are biochemical antioxidants: structure-activity relationship, *Mol Pharmacol* 61:260-268, 2002.

Neilan et al., Pharmacological characterization of the dermorphin analog [Dmt$^1$]DALDA, a highly potent and selective u-opioid peptide, *European Journal of Pharmacology*, 419(1):15-23, 2001.

Ngo et al., Computational complexity, protein structure prediction, and the leventhal paradox, the protein folding problem and tertiary structure prediction, (Ed. K. Merz Jr. And S. Le Grand), *Birkhauser Boston*, 492-495, 1994.

Omoniyi et al., A peripheral site of action for the attenuation of baroreflex-mediated bradycardia by intravenous μ-opioid agonists, *Journal of Cardiovascular Pharmocolgy*™, 35(2):269-274, 2000.

Pages et al., Cystamine and cysteamine increase brain levels of BDNF in Huntington Disease via HSJ1b and transglutaminase, *Journal of Clinical Investigation*, 116(5):1410-1424, May 2006.

Patel et al., Pharmacotherapy of cognitive impairment in Alzheimer's Disease: a review, *J. Geriatr. Psychiatry Neurol.*, 8:81-95, 1995.

Petri et al., Cell-permeable peptide antioxidants as a novel therapeutic approach in a mouse model of amyotrophic lateral sclerosis, *J Neurochem.*, 98(4):1141-1148, Aug. 2006.

Richard et al., Cell-penetrating peptides, *Journal of Biological Chemistry*, 278(1):585-590, 2003.

Rudinger, J., Peptide hormones, (Ed. J. A. Parson), *University Park Press*, Baltimore, 1-7, 1976.

Schiller et al., Dermorphin analogues carrying an increased positive net charge in their "message" domain display extremely high μ-opioid receptor selectivity, *Journal of Medicinal Chemistry*, 32(3):698-703, 1989.

Schiller et al., Opioid peptide analogs with novel activity profiles as potential therapeutic agents for use in analgesia, Peptide Science-Present and Future, Proc. 1$^{st}$ Int. Pept. Symp., 665-669, 1999.

Schiller et al., Opioid peptide analogs with novel activity profiles as potential therapeutic agents for use in analgesia, 1$^{st}$ Int. Pept. Symp., Program and Abstracts, 0-36, o. 77, 1997.

Schiller et al., Synthesis and in vitro opioid activity profiles of DALDA analogues, *European Journal of Medicinal Chemistry*, 35(10):895-901, Oct. 2000.

Schiller et al., Tipp: A highly potent and stable pseudopeptide opioid receptor antagonist with extraordinary selectivity, *J. Med. Chem.*, 36:3182-3187, 1993.

Schiller et al., Unsulfated C-terminal 7-peptide of cholecystokinin: a new ligand of the opiate receptor, *Biochemical and Biophysical Research Communications*, 85:1332-1338, 1978.

Schiller, P. W. et al., Opioid peptide analogs with novel activity profiles as potential therapeutic agents for use in analgesia, *Stn Caplus*, 132:102403, 1997.

Schwarze, Steven R., et al., In vivo protein transduction: intracellular delivery of biologically active proteins, compounds and DNA, *Trends in Pharmacological Sciences*, 21:45-48, 2000.

Shimoyama, et al. Antinociceptive and respiratory effects of intrathecal H-Tyr-D-Arg-Phe-Lys-NH$_2$ (DALDA) and [DMT$^1$]DALDA, *The Journal of Pharmacology and Experimental Therapeutics*, 297(1):364-371, Apr. 2001.

Shroff et al., Effects of intrathecal opioid on extubation time, analgesia and intensive care unit stay following coronary artery bypass grafting, *Journal of Clinical Anesthesia*, 9:415-419, 1997.

Simmons, Zachary, Management strategies for patients with Amyotrophic Lateral Sclerosis from diagnosis through death. *The Neurologist* 11(5):257-270, Sep. 2005 (abstract only) (File Medline on STN. An No. 2005478947).

Skolnick et al., From genes to protein structure and function: novel applications of computational approaches in the genomic era, *Trends in Biotech*, 18(1):34-39, 2000.

Smith et al., The challenges of genome sequence annotation or the devil is in the details, *Nature Biotechnology*, 15:1222-1223, 1997.

Song et al., A potent opiate agonist protects against myocardial stunning during myocardial ischemia and reperfusion in rats, *Coronary Artery Disease*, 16:407-410, 2005.

Spetea, Mariana et al., Interaction of agonist peptides (3H) Tyr-D-Ala-Phe-Phe-NH2 with mu-opioid receptor in rat brain and CHO-mu/1 cell line, *Peptides*, 19(6):1091-1098, 1998.

Sriram et al., Experimental allergic encephalomyelitis: a misleading model of Multiple Sclerosis, *Ann. Neurol.*, 58:939-945, 2005.

(56) References Cited

OTHER PUBLICATIONS

Steinman et al., How to successfully apply animal studies in experimental allergic encephalomyelitis to research on Multiple Sclerosis, *Ann. Neurol.*, 60:12-21, 2006.

Szeto et al., In vivo disposition of dermorphin analog (DALDA) in nonpregnant and pregnant sheep, *The Journal of Pharmacology and Experimental Therapeutics*, 284(1):61-65, 1998.

Szeto et al., In vivo pharmacokinetics of selective u-opioid peptide agonists, *The Journal of Pharmacology and Experimental Therapeutics*, 298(1):57-61, Jul. 2001.

Szeto et al., Mu-opioid receptor densensitization and resensitization in vivo, International Narcotics Research Conference, Poster Abstracts, Monday, Mon19:5, 1999.

Szeto et al., Respiratory depression after intravenous administration of o-Selective opioid peptide analogs, *Peptides*, 20:101-105, 1999.

Szeto, Hazel H., Development of mitochondria-targeted aromatic-cationic peptides for neurodegenerative diseases, *Annals of the New York Academy of Sciences*, 1147:112-121, 2008.

Szeto, Hazel H., Mitochondria-targeted cytoprotective peptides for ischemia-reperfusion injury, *Antioxid Redox Signal*, 10(3):601-619, Mar. 2008.

Szeto, Hazel H. Cell-permeable, mitochondrial-targeted, peptide antioxidants. *The AAPS Journal* 8(2): E277-E283, 2006.

Szeto, Hazel H. Mitochondria-targeted peptide antioxidants: Novel Neuroprotective Agents. *The AAPS Journal* 8(3): E521-E531, 2006.

Thomas et al., Mitochondrial targeting with antioxidant peptide SS-31 prevents mitochondrial depolarization, reduces islet cell apoptosis, increases islet cell yield, and improves posttransplantation function. *J Am Soc Nephrol* 18: 213-222, 2007.

Wells, James A., Additivity of mutational effects in proteins, *Biochemistry, American Chemical Society*, 29(37):8509-8517 Sep. 18, 1990.

Wu et al., Myocardial protective effect of mu opioid agonists, International Narcotics Research Conference, Poster Abstracts, Sun59:15, 1999.

Wu, et al., A highly potent peptide analgesic that protects against ischemia-reperfusion-induced myocardial stunning, *Am J Physiol Heart Circ Physiol*, 283:H783-H791, 2002.

Yang et al., Mitochondria targeted peptides protect against 1-methyl-4-phenyl-1, 2, 3, 6-tetrahydropyridine neurotoxicity, *Antioxid Redox Signal*, 2009 (epublished ahead of print).

Zadina, J. et al., A potent and selective endogenous agonist for the mu-opiate receptor, *Nature*, 386:499-502, Apr. 3, 1997.

Zhao et al., Mitochondrial-targeted peptide prevents mitochondrial depolarization and apoptosis induced by tert-butyl hydroperoxide in neuronal cell lines, *Biochem Pharmacol.*, 70(12):1796-1806, Oct. 10, 2005 (epublished).

Zhao et al., Cell-permeable peptide antioxidants targeted to inner mitochondrial membrane inhibit mitochondrial swelling, oxidative cell death, and reperfusion injury, *J. Biol. Chem.*, 279(33):34682-34690, Aug. 2004.

Zhao, Guo-Min et al., Profound spinal tolerance after repeated exposure to a highly selective u-opioid peptide agonist: Role of o-opioid receptors, *J Pharma. Exper. Thera.*, 302(1):188-196, 2002.

Zhao, Kesheng, et al., Transcellular transport of a highly polar 3+ net charge opioid tetrapeptide, *Journal of Pharmacology and Experimental Therapeutics*, 304(1):425-432, 2003.

Zhao, Kesheng et al., Comparison of [Dmt1]DALDA and DAMGO in Binding and G Protein Activation at μ, δ, and κ Opioid Receptors. *J. Parmacology and Experimental Therapeutics* 307(3): 947-954, 2003.

Zhao, Kesheng, et al., Translocation of a 3+ net charge tetrapeptide across plasma membrane of mammalian cells, abstract published on-line May 1, 2002, World Congress of Pharmacology Meeting, held Jul. 2002.

International Search Report and Written Opinion in International Application No. PCT/US2009/35132, dated May 8, 2009.

Schnellmann et al. Pathophysiology of Nephrotoxic Acute Renal Failure. Atlas of the Diseases of the Kidney. CHpater 15. 1999. 14 pages.

Non-Final Office Action for U.S. Appl. No. 12/392,565 Dtd Jun. 15, 2011.

Notice of Allowance for U.S. Appl. No. 12/392,565 Dtd Nov. 22, 2011.

Restriction Requirement for U.S. Appl. No. 12/392,565 Dtd Mar. 21, 2011.

Hricik et al., Uric acid nephrolithiasis and acute renal failure secondary to streptozotocin nephrotoxicity. American Journal of Medicine 1988; 84(1): 153-156.

International Preliminary Report on Patentability for PCT Application No. PCT/US2009/035132; mailed Sep. 10, 2010 (6 pages).

Extended European Search Report in EP Application No. 09713874.7; issued Jan. 31, 2012 (8 pages).

Anderson et al.; "Mitochondrial H2O2 emission and cellular redox state link excess fat intake to insulin resistance in rodents and humans"; J. Clin. Invest. (2009); vol. 119(3), pp. 573-581.

Anderson et al.; "Mitochondrial production of reactive oxygen species contributes to the β adrenergic stimulation of mouse cardiomyocytes"; J. Physiol. (2011); vol. 589(7); pp. 1791-1801.

Calkins et al.; "Impaired mitochondrial biogenesis, defective axonal transport of mitochondria, abnormal mitochondrial dynamics and synaptic degeneration in a mouse model of Alzheimer's disease"; Hum. Mol. Genet. (2011); vol. 20(23); pp. 4515-4529.

Cao et al.; "Mitochondria-targeted antioxidant attenuates high glucose-induced P38 MAPK pathway activation in human neuroblastoma cells"; Mol. Med. Report. (2012); vol. 5(4); pp. 929-934.

Carter et al.; "Evaluation of the antioxidant peptide SS31 for treatment of burn-induced insulin resistance"; Int. J. Mol. Med. (2011); vol. 28(4); pp. 589-594.

Chen et al.; "Mitochondria-targeted peptide MTP-131 alleviates mitochondrial dysfunction and oxidative damage in human trabecular meshwork cells"; Invest. Ophthalmol. Vis. Sci. (2011); vol. 52(10); pp. 7027-7037.

Dai et al.; "Mitochondrial targeted antioxidant peptide ameliorates hypertensive cardiomyopathy"; J. Am. Coll. Cardiol. (2011); vol. 58(1); pp. 73-82.

Eirin et al.; "A mitochondrial permeability transition pore inhibitor improves renal outcomes after revascularization in experimental atherosclerotic renal artery stenosis" J. Am. Heart Assoc. (2012) (manuscript) 35 pages.

Gilliam et al.; "Doxorubicin acts via mitochondrial ROS to stimulate catabolism in C2C12 Myotubes"; Am. J. Physiol. Cell Physiol. (2012); vol. 302(1); pp. C195-C202.

Kloner et al.; "Reduction of ischemia/reperfusion injury With Bendavia, a mitochondria-targeting cytoprotective peptide"; J. Am. Heart Assoc. (2012) (proof) 15 pages.

Lee et al.; "Novel mitochondria-targeted antioxidant peptide ameliorates burn-induced apoptosis and endoplasmic reticulum stress in the skeletal muscle of mice"; Shock (2011); vol. 36(6); pp. 580-585.

Li et al.; "Mitochondria-targeted antioxidant peptide SS31 attenuates high glucose-induced injury on human retinal endothelial cells"; Biochem. Biophys. Res. Commun. (2011); vol. 404(1); pp. 349-356.

Ma et al.; "Superoxide flashes: early mitochondrial signals for oxidative stress-induced apoptosis"; J. Biol. Chem. (2011); vol. 286(31); pp. 27573-27581.

Manczak et al.; "Mitochondria-targeted antioxidants protect against amyloid-β toxicity in Alzheimer's Disease neurons"; J. Alzheimer's Dis. (2010); vol. 20(2); pp. S609-S631.

Min et al.; "Mitochondrial-targeted antioxidants protect skeletal muscle against immobilization-induced muscle atrophy"; J. Appl. Physiol. (2011); vol. 111(5); pp. 1459-1466.

Nieborowska-Skorska et al.; "Rac2-MRC-cIII-generated ROS cause genomic instability in chronic myeloid leukemia stem cells and primitive progenitors"; Blood (2012); vol. 119(18); pp. 4253-4263.

Powers et al.; "Mitochondria-targeted antioxidants protect against mechanical-ventilation-induced diaphragm weakness"; Crit. Care Med. (2011); vol. 39(7); pp. 1749-1759.

(56) References Cited

OTHER PUBLICATIONS

Reddy et al.; "Toxicity of neurons treated with herbicides and neuroprotection by mitochondria-targeted antioxidant SS31"; Int. J. Environ. Res. Public Health. (2011); vol. 8(1); pp. 203-221.

Sharma et al.; "Mitochondrial respiratory complex I dysfunction promotes tumorigenesis through ROS alteration and AKT activation"; Hum. Mol. Genet. (2011); vol. 20(23); pp. 4605-4616.

Sloan et al.; "Mitochondrial permeability transition in the diabetic heart: Contributions of thiol redox state and mitochondrial calcium to augmented reperfusion injury"; J. Mol. Cell. Cardiol. (2012); vol. 52(5); pp. 1009-1018.

Szeto et al.; "Mitochondria-targeted peptide accelerates ATP recovery and reduces ischemic kidney injury"; J. Am. Soc. Nephrol. (2011); vol. 22(6); pp. 1041-1052.

Szeto, H. & Schiller, P.; "Novel therapies targeting inner mitochondrial membrane—from discovery to clinical development"; Pharm. Res. (2011); vol. 28(11); pp. 2669-2679.

Wang et al.; "Elevated mitochondrial reactive oxygen species generation affects the immune response via hypoxia-inducible factor-1 α in long-lived Mclk1+/−mouse mutants"; J. Immunol. (2010); vol. 184(2); pp. 582-590.

Whiteman et al.; "Do mitochondriotropic antioxidants prevent chlorinative stress-induced mitochondrial and cellular injury?"; Antioxid. Redox Signal. (2008); vol. 10(3); pp. 641-650.

Zhu et al.; "Histone deacetylase-3 activation promotes tumor necrosis factor-alpha (TNF-α) expression in cardiomyocytes during lipopolysaccharide stimulation"; J. Biol. Chem. (2010); vol. 285(13); pp. 9429-9436.

Zhu et al.; "MicroRNA-195 promotes palmitate-induced apoptosis in cardiomyocytes by down-regulating Sirt1"; Cardiovasc. Res. (2011); vol. 92(1); pp. 75-84.

Second Office Action for Chinese Application. No. 200980106215.9 dated Mar. 13, 2013. English Translation 5 pages.

Alam, N.M. et al., "Reducing Mitochondrial Oxidative Stress to Treat Diabetes and Age-related Visual Decline," Society of Neuroscience, (2011), Poster Presentation (1 page).

Alam, N.M., et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).

Alam, Nazia et al., "A novel Peptide that Improves Mitochondrial Function Reverses Diabetes- and Age-Related Visual Decline," American Aging Association, (2012), Abstract (1 page).

Brown, David A. et al., "Bendavia, a mitochondria-targeting peptide, reduces reperfusion injury and reactive oxygen species levels through a mechanism independent of direct oxygen radical scavenging: A multicenter study," American Heart Association, (2012), Abstract (1 page).

Brown, David A., Ph.D., "Mitochondrial Derived Cardioprotection in Exercised Hearts: Role of Cardiac Glutathione," American College of Sports Medicine, (2012), DB Lab Presentation (28 pages).

Chonn, et al., "Recent Advances in Liposome Drug Delivery Systems," Current Opinion in Biotechnology, (1995), vol. 6, pp. 698-708.

Eirin, Alfonso et al., "A Mitochondrial Permeability Transition Pore Inhibitor Improves Renal Outcomes After Revascularization in Experimental Atherosclerotic Renal Artery Stenosis," J. Am. Heart Assoc., (2012), vol. 60, pp. 1242-1249; available at http://hyper.ahajournals.org/content/60/5/1242 and supplemental content available at http://hyper.ahajournals.org/content/suppl.2012/10/08/HYPERTENSIONAHA.112.199919.DC1.html (26 pages total).

Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).

Eirin, Alfonso et. al., "Mitochondrial Targeted Peptides Attenuate Myocardial Damage after Renal Revascularization in Experimental Atherosclerotic Renovascular Hypertension," American Society of Nephrology, (2012), Abstract & figures (2 pages).

Eirin, Alfonso, et. al., "MTP-131 reduces renal injury after percutaneous transluminal renal angioplasty (PTRA) in swine atherosclerotic renal artery stenosis (ARAS)," American Society of Nephrology, 2011, Poster Presentation (1 page).

First Office Action for Chinese Application No. 200980106215.9 dated May 30, 2012 (5 pages)—English Translation Provided.

Gregoriadis, "Engineering Liposomes for Drug Delivery: Progress and Problems," Trends Biotechnol., vol. 13, No. 12, (1995), pp. 527-537.

Hale, Sharon L. et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).

Kloner, Robert A., et. al., "Bendavia, A Novel Mitochondrial-Targeted Cytoprotective Compound Reduces Ischemia/Reperfusion Injury: Experience in 3 Independent Laboratories," American Heart Association, (2011), Abstract (2 pages).

Liang, XL., et. al., "SS31 protects human RPE cells from oxidative damage and reduces laser-induced choroidal neovascularization," Association for Research in Vision and Opthamology, 2010, Poster Presentation (1 page).

Lichtenberg, et al., "Liposomes: Preparation, Characterization and Preservation," Methods Biochem Anal., (1988), vol. 33, pp. 337-462.

Liu, S., et. al., "Boosting mitochondrial function to minimize ischemia-reperfusion injury," Experimental Biology, (2011), Poster Presentation (1 page).

Liu, S., et. al., "Mitochondria-targeting peptide (SS-31) promotes rapid repair of actin cytoskeleton following ischemia and protects tubular epithelial cell architecture," American Society of Nephrology, (2012), Abstract (2), 1 page.

Marcinek, David J., et al., "Acute pharmacological intervention reverses mitochondrial deficits and improves function in aged skeletal muscle," American Aging Association, (2012), Abstract (1 page).

Min, K., et. al., "Mitochondrial-targeted antioxidants attenuate immobilization-induced skeletal muscle atrophy," Experimental Biology, (2011), Abstract (1 page).

Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.

Putney, Scott D., "Encapsulation of proteins for improved delivery," Current Opinion in Chemical Biology, (1998), vol. 2, No. 4, pp. 548-552.

Rabinovitch, Peter, "Mitochondrial Oxidative Stress and Cardiac Aging," Basic Cardiovascular Sciences, 2011, Presentation (19 pages).

Reddy, KR., "Controlled-release, pegylation, liposomal formulations: new mechanisms in the delivery of injectable drugs," Ann Pharmacother., (2000), vol. 34, Nos. 7-8, pp. 915-923.

Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, 2010, Abstract (1 page).

Sabbah, H.N., et al., "Acute Intravenous Infusion of Bendavia (MTP-131), A Novel Mitochondria-Targeting Peptide, Improves Left Ventricular Systolic Function in Dogs With Advanced Heart Failure," American Heart Association, (2012), Abstract (1 page).

Szeto, H.H., et al., "Mitochondria-targeting peptide (SS-31, Bendavia (Registered Trademark)) prvents microvascular rarafaction, inflammation, and fibrosis caused by ischemia-reperfusion injury," American Society of Nephrology, (2012), Abstract (1 page).

Szeto, Hazel H., "Mitochondrial Protection as Strategy to treat Ischemia-Reperfusion Injury," American Society of Nephrology, 2010, Presentation (17 pages).

Szeto, Hazel H., "The development of a therapeutic peptide for mitochondrial protection—from bench to bedside," Experimental Biology, 2011, Poster Presentation (1 page).

Szeto, Hazel H., et al., "Rapid Restoration of ATP by SS-31, an Inhibitor of Mitochondrial Permeability Transition, Prevents Tubular

(56) References Cited

OTHER PUBLICATIONS

Cytoskeletal Rearrnagement in Renal Ischemia-Reperfusion Injury," American Siciety of Nephrology, 2010, Poster Presentation (1 page).
Tiganis, Tony, "Reactive Oxygen Species & NAPDH Oxidases in Insulin Signalling," NOX Gordon Research Conference, Jun. 3-8, 2012, Presentation (44 pages).

Weiner, "Liposomes for Protein Delivery: Selecting Manufacture and Development Processes," Immunomethods, vol. 4, No. 3, (1994), pp. 201-209.
English translation of Office Action on Japanese Application No. 2010-547861 dated Jul. 10, 2013 (3 pages).
English translation of Third Office Action on Chinese Application No. 200980106215.9 dated Jun. 20, 2013 (6 pages).

* cited by examiner

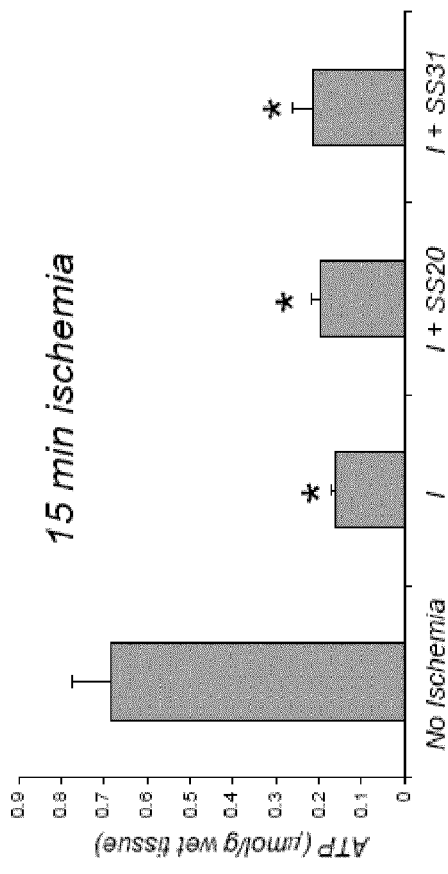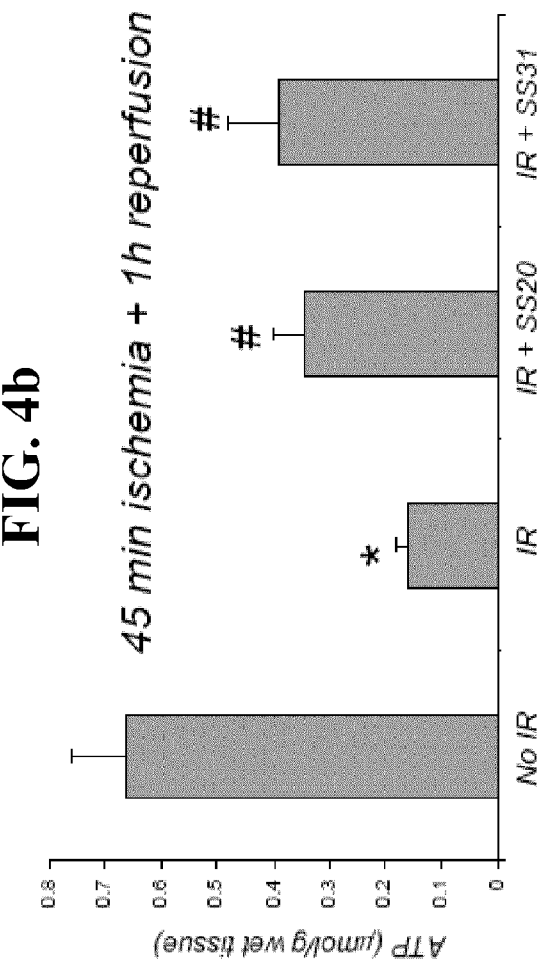

Control OK

Control CK

SS31 OK 3mg/kg

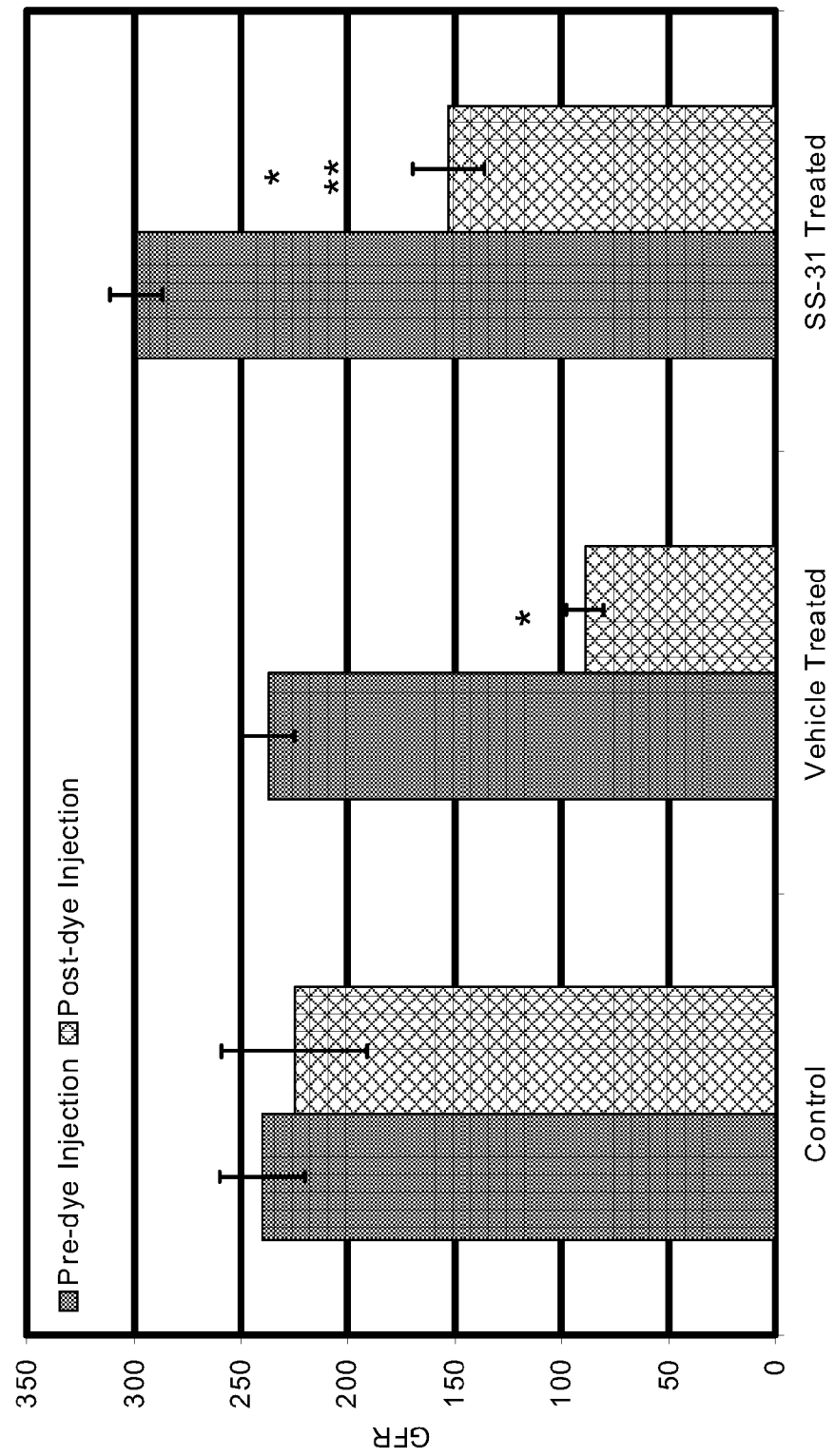

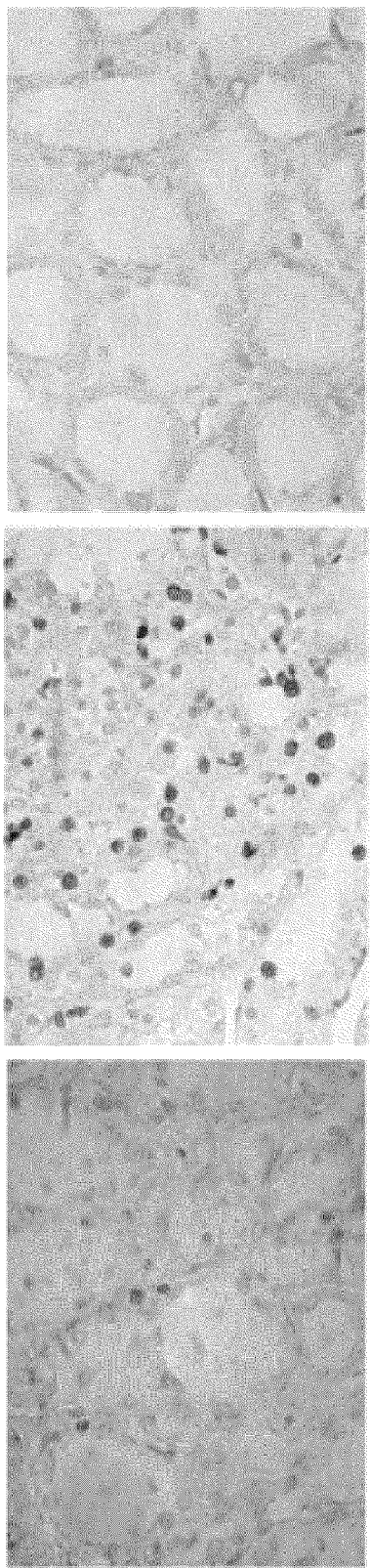

FIG. 16c 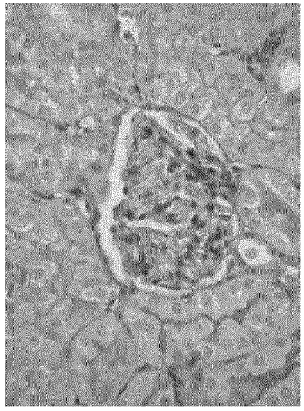 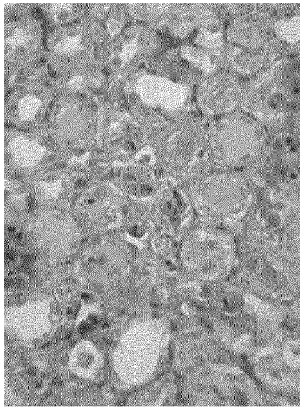 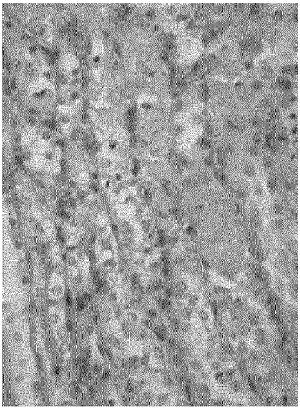 Normal rat
FIG. 16b  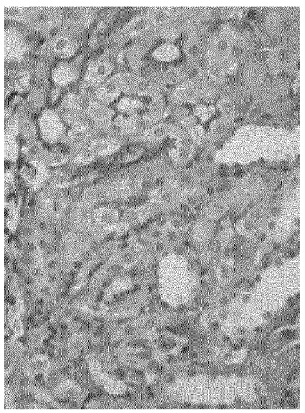 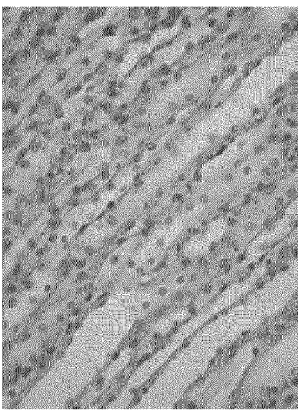 Indo/L-Name/dye/SS-31
FIG. 16a 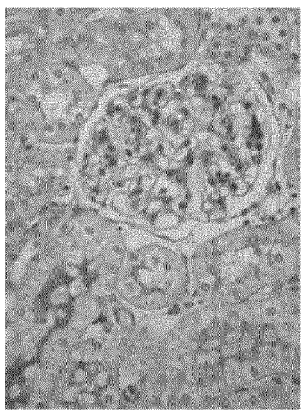 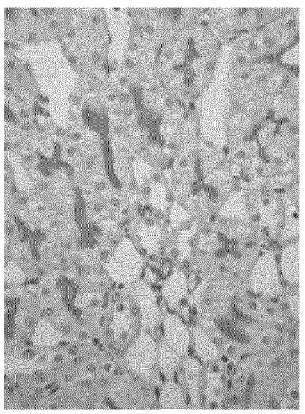 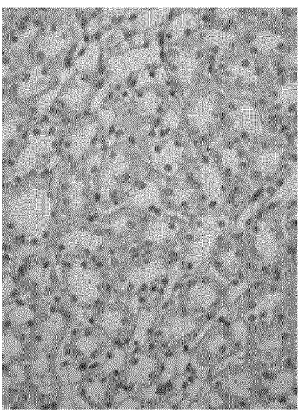 Indo/L-Name/dye/saline
Cortex — Outer medulla — Inner medulla Group A, HFD/STZ rat, PBS+Dye+PBS, (n=10)
Group B, HFD/STZ rat, SS-31+Dye+SS-31 (n=9)
Group C, NRC rat, PBS+Dye+PBS (n=9)

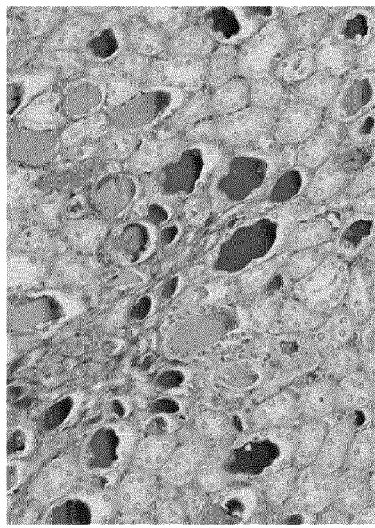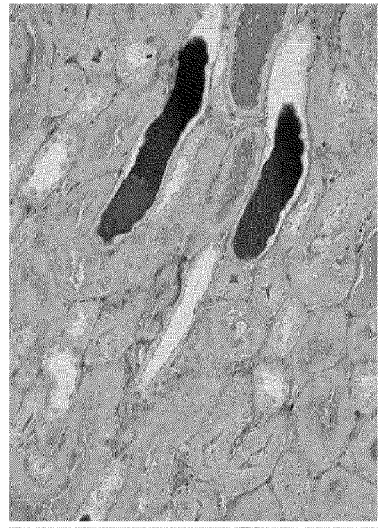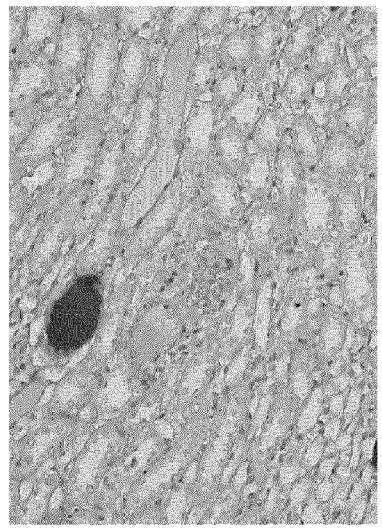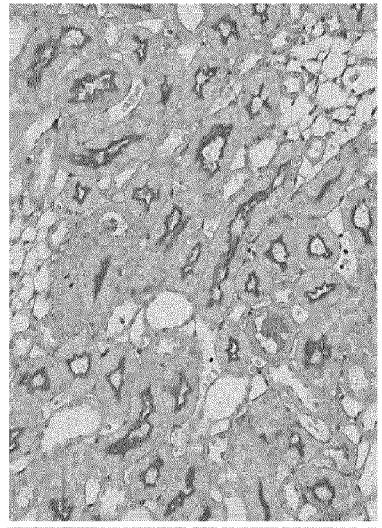
FIG. 22a  FIG. 22b

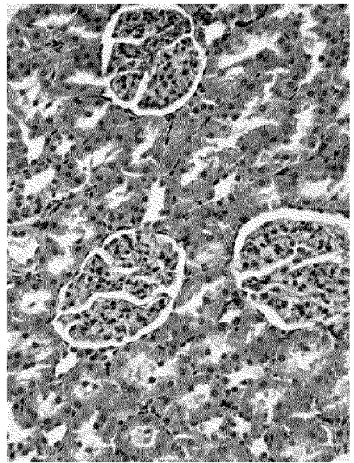
FIG. 31b SS-31 treated group
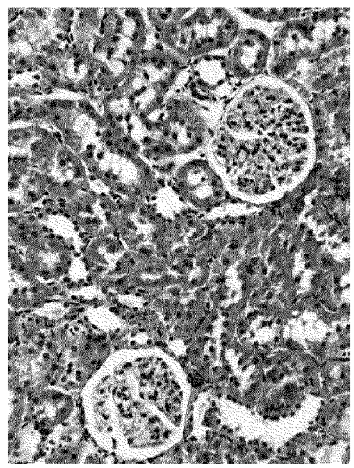
FIG. 31c Naïve control group
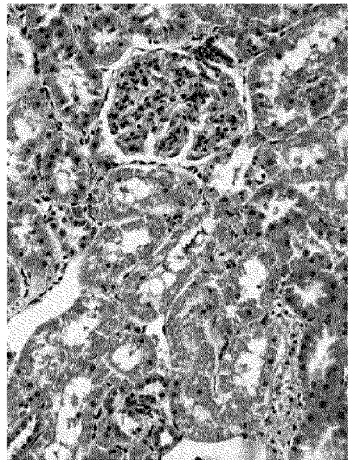
FIG. 31a CCl4 control group

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ctgaagaaga ttgcgcagaa                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
atggcataaa ttcccactgc                                                    20

METHODS FOR PREVENTION AND TREATMENT OF ACUTE RENAL INJURY

CROSS-REFERENCE TO RELATED APPLICATIONS

This application is a continuation of U.S. patent application Ser. No. 12/392,565, filed Feb. 25, 2009, which claims priority to U.S. Provisional Application No. 61/031,585, filed Feb. 26, 2008. The entire contents of the foregoing applications are hereby incorporated herein by reference.

GOVERNMENT SUPPORT

The invention was made with United States government support awarded by the following agencies: NIH DK58355; NIH DA08924; and NIH DK73595. The United States government has certain rights in this invention.

BACKGROUND

Acute Renal Injury (ARI), also known as acute renal failure (ARF) or acute kidney injury (AKI), is a serious medical condition of the kidneys. ARI is characterized by a decline of glomerular filtration rate, urine output, or both. ARI is accompanied by an inflammatory response that if unchecked can lead to renal fibrosis and chronic renal failure. ARI usually occurs over a period of hours or days and is potentially reversible. ARI is a common complication in hospitalized patients, and its incidence has risen significantly in the past 15 years. A particular type of ARI, contrast-induced nephropathy, is caused by the toxic effects of some radiocontrast agents.

SUMMARY

The present invention provides a method for protecting a kidney from acute renal injury in a subject in need thereof. The method includes administering to the subject an effective amount of an aromatic-cationic peptide. The aromatic-cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; and (e) a relationship between the minimum number of aromatic groups (a) and the total number of net positive charges ($p_t$) wherein 3a is the largest number that is less than or equal to $p_t+1$, except that when a is 1, $p_t$ may also be 1.

In one embodiment, peptide is administered to a subject prior to or simultaneously with a radiocontrast agent, in order to prevent or ameliorate the incidence of contrast-induced nephropathy. In one embodiment, the peptide is selected from the group consisting of Phe-D-Arg-Phe-Lys-NH$_2$ (SS-20) or D-Arg-2'6'Dmt-Lys-Phe-NH2 (SS-31).

In one embodiment, the acute renal injury is associated with exposure of the subject to a nephrotoxic agent. In one embodiment, the peptide is administered to the subject prior to or simultaneously with the exposure to the nephrotoxic agent.

In one embodiment, the nephrotoxic agent is a radiocontrast dye, e.g., acetrizoate; diatrizoate; iodamide; ioglicate; iothalamate; ioxithalamate; metrizoate; metrizamide; iohexol; iopamidol; iopentol; iopromide; and ioversol.

In one embodiment, the nephrotoxic agent is a drug or chemical. In illustrative embodiments, the drug or chemical is one or more of the compounds selected from the group consisting of: cisplatin; gentamicin; cephaloridine; cyclosporine; amphotericin; carbon tetrachloride; trichloroethylene; and dichloroacetylene.

In another aspect, the invention provides a method of treating acute or chronic renal injury in a subject in need thereof. The method includes administering to the subject an effective amount of an aromatic-cationic peptide. The aromatic-cationic peptides have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; and (e) a relationship between the minimum number of aromatic groups (a) and the total number of net positive charges ($p_t$) wherein 3a is the largest number that is less than or equal to $p_t+1$, except that when a is 1, $p_t$ may also be 1. In one embodiment, the peptide is administered after exposure of the subject to a nephrotoxic agent.

In one embodiment, the peptide is selected from the group consisting of Phe-D-Arg-Phe-Lys-NH$_2$ (SS-20) and D-Arg-2'6'Dmt-Lys-Phe-NH$_2$ (SS-31) peptide.

In one embodiment, the peptide is defined by formula I:

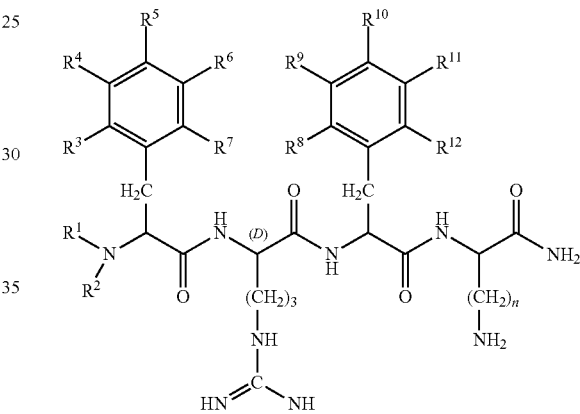

wherein $R^1$ and $R^2$ are each independently selected from
(i) hydrogen;
(ii) linear or branched $C_1$-$C_6$ alkyl;

(iii)

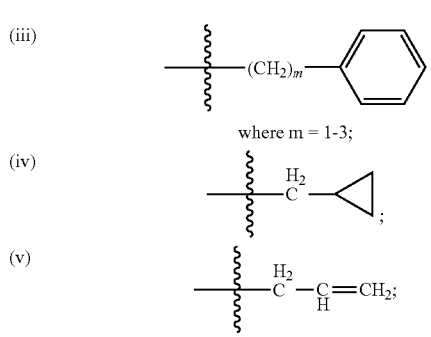

where m = 1-3;

(iv)

(v)

$R^3$, $R^4$, $R^5$, $R^6$, $R^7$, $R^8$, $R^9$, $R^{10}$, $R^{11}$ anFd $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;

(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

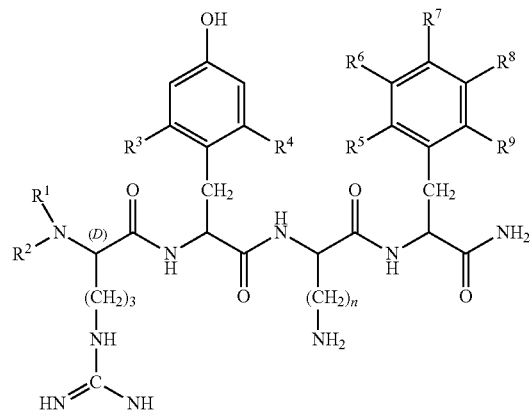

wherein $R^1$ and $R^2$ are each independently selected from
(i) hydrogen;
(ii) linear or branched $C_1$-$C_6$ alkyl;

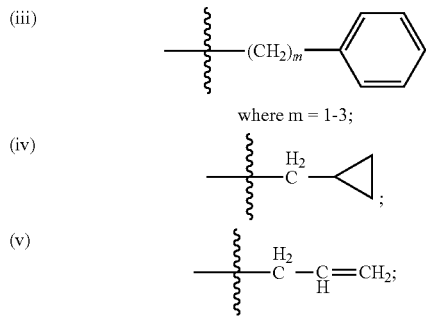

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one aspect, the disclosure provides a method for protecting a kidney from chronic renal injury in a subject in need thereof, the method comprising administering to the subject an effective amount of a peptide selected from the group consisting of Phe-D-Arg-Phe-Lys-NH2 (SS-20) and D-Arg-2'6'Dmt-Lys-Phe-NH2 (SS-31). In one embodiment, the chronic renal injury is associated with administration of or exposure to a nephrotoxic agent, e.g., a drug or chemical capable of causing chronic kidney injury. In a particular embodiment, the drug or chemical is carbon tetrachloride.

In some embodiments, the peptides are useful for the prevention and/or treatment of acute hepatic injury caused by ischemia, drugs (acetaminophen, alcohol), viruses, obesity (non-alcoholic steatohepatitis), and obstruction (bile duct obstruction, tumors). In some embodiments, the aromatic-cationic peptides of the invention are administered to a subject to prevent or treat acute liver failure (ALF).

BRIEF DESCRIPTION OF THE FIGURES

FIG. 4 presents charts showing treatment with SS-20 or SS-31 significantly increased rate of ATP production after reperfusion. FIG. 4a shows the ATP content in renal tissue at the end of 15 min ischemia. FIG. 4b shows the ATP content in renal tissue after 1 h reperfusion following 45 min ischemia.

FIG. 6 presents data showing that SS-1 decreases medullary fibrosis in a 14-day unilateral ureteral obstruction (UUO) model.

FIG. 11 presents data showing that SS-31 decreases oxidative damage in a 14-day UUO model.

FIG. 12 is a chart showing SS-31 reduced renal dysfunction caused by radiocontrast dye.

FIG. 13 is a series of micrographs showing that SS-31 protected renal tubules from radiocontrast dye injury. PAS staining revealed control rat kidneys with normal morphology, demonstrated by intact brush borders on proximal tubules (FIG. 13a). Dye treatment resulted in loss of the characteristic renal brush border in proximal tubule cells, flattening of the epithelial cells, as well as some vacuolization (FIG. 13b). These effects were attenuated with SS-31 treatment. PAS staining in these samples revealed intact brush borders and normal glomeruli (FIG. 13c).

FIG. 14 is a series of micrographs showing that SS-31 prevented renal tubular apoptosis induced by radiocontrast dye injury. The TUNEL stain was used to visualize apoptotic renal tubules. Control kidneys showed few apoptotic cells/hpf (FIG. 14a). Vehicle-treated, dye-injected kidneys had numerous apoptotic cells per high power field (hpf) (FIG. 14b). This effect was greatly attenuated in SS-31-treated, dye injected kidneys (FIG. 14c).

FIG. 16 is a series of PAS-stained micrographs showing that dye treatment resulted in a loss of the characteristic renal brush border in proximal tubule cells, as well as some vacuolization (FIG. 16a). These effects were attenuated with SS-31 treatment, PAS staining in these samples revealed intact brush borders and normal glomeruli (FIG. 16b). FIG. 16c showed the control rat kidneys with normal morphology, demonstrated by intact brush borders on proximal tubules.

FIG. 22a shows a series of micrographs of PAS staining of renal sections from rats treated with glycerin, Diatrizoate, and a control (PBS). FIG. 22b shows a series of micrographs of PAS staining of renal sections from rats treated with glycerin, Diatrizoate, and SS-31.

FIG. 31 is a series of micrographs showing H&E staining of a $CCl_4$ control group (FIG. 31a), an SS-31-treated group (FIG. 31b), and a naïve control group (FIG. 31c).

DETAILED DESCRIPTION

Figure 1:
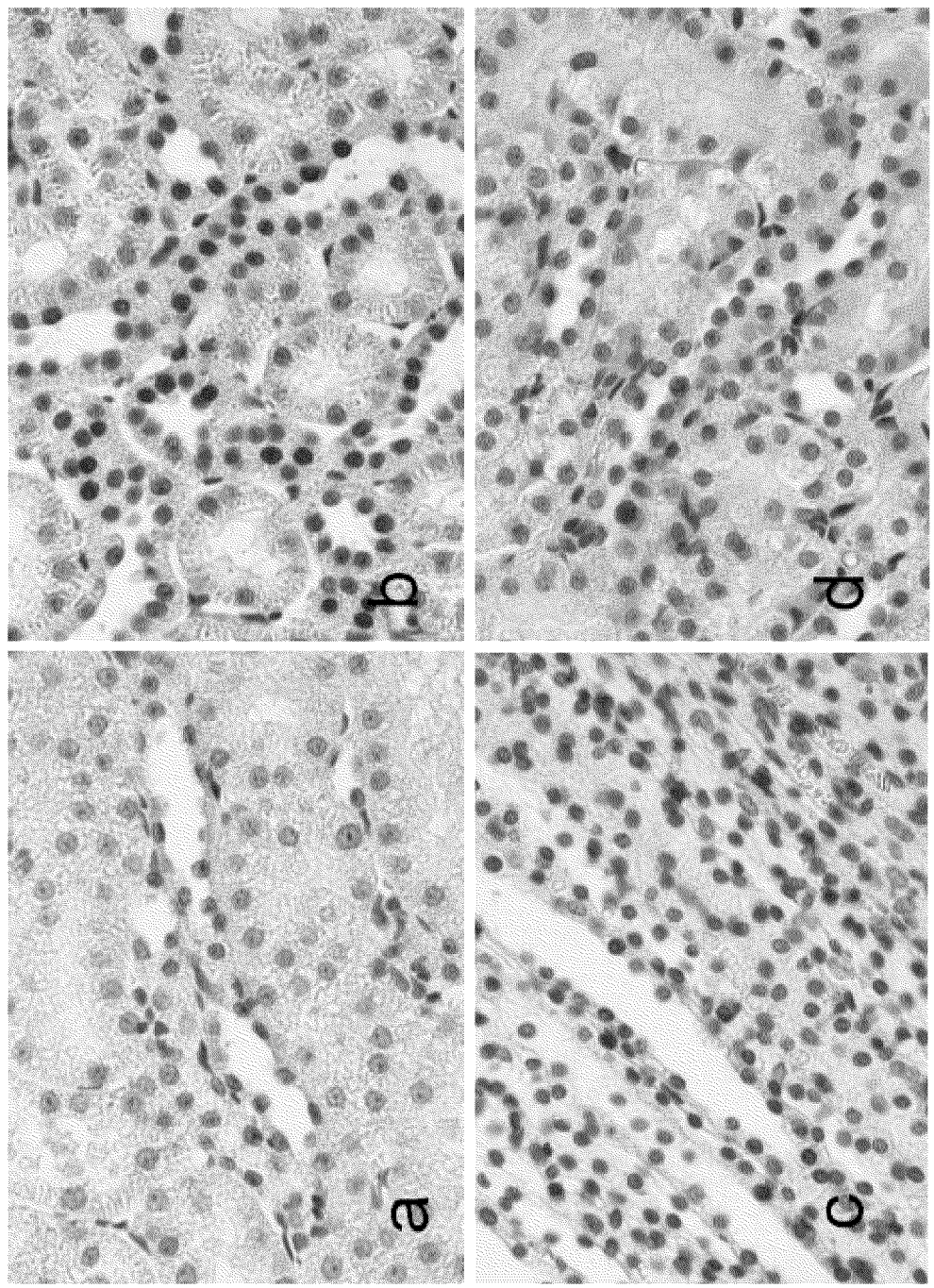
FIG. 1a-1d shows micrographs of renal sections stained for apoptotic cells using TUNEL.

The invention is based on the surprising discovery by the inventors that certain aromatic-cationic peptides can prevent and/or treat acute organ failure, e.g., acute renal injury or acute liver failure in a subject. In some aspects, aromatic-cationic peptides can prevent and/or treat chronic organ damage, e.g., chronic renal injury. It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N.Y., 1987); and *Meth. Enzymol.*, Vols. 154 and 155, Wu & Grossman, and Wu, Eds., respectively. All references cited herein are incorporated herein by reference in their entireties and for all purposes to the same extent as if each individual publication, patent, or patent application was specifically and individually incorporated by reference in its entirety for all purposes.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, phrases such as element A is "associated with" element B mean both elements exist, but should not be interpreted as meaning one element necessarily is causally linked to the other.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may be acute renal injury or acute liver failure or any associated symptoms or complications. In one embodiment, the medical condition is acute renal injury associated with radiocontrast dye administration.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the word "protect" or "protecting" refers to decreasing the likelihood and/or risk that the subject treated with a peptide of the invention will develop a given disease or disorder, e.g., acute renal injury or acute liver failure. Typically, the likelihood of developing the disease or disorder is considered to be reduced if the likelihood is decreased by at least about 10%, preferably at least about 25%, more preferably at least about 50%, even more preferably at least about 75%, and most preferably at least about 90%, in comparison to the likelihood and/or risk that the same subject untreated with a peptide of the invention will develop tissue injury, e.g., acute renal injury or acute liver failure. In particular embodiments, the peptides protect a subject from acute renal injury caused by a contrast agent (i.e., contrast-induced nephropathy) when the peptides are administered prior to or simultaneously with the contrast agent.

The term "subject" as used herein refers to a member of any vertebrate species. The methods of the presently disclosed subject matter are particularly useful for warm-blooded vertebrates. Provided herein is the treatment of mammals such as humans, as well as those mammals of importance due to being endangered, of economic importance (animals raised on farms for consumption by humans) and/or social importance (animals kept as pets or in zoos) to humans. In particular embodiments, the subject is a human.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disease or condition if, after receiving a therapeutic amount of the aromatic-cationic peptides according to the methods of the present invention, the subject shows observable and/or measurable reduction in or absence of one or more signs and symptoms of a particular disease or condition. For example, for acute renal injury, treatment or prevention may include a reduction in metabolic acidosis, hyperkalaemia, oliguria or anuria, restoration in body fluid balance, and improved effects on other organ systems. Kidney function may also be assessed by measuring serum creatinine levels, serum creatinine clearance, or blood urea nitrogen levels. It is also to be appreciated that the various modes of treatment or prevention of medical conditions as described are intended to mean "substantial", which includes total but also less than total treatment or prevention, and wherein some biologically or medically relevant result is achieved.

Peptides

The aromatic-cationic peptides useful in the present invention are water-soluble and highly polar. Despite these properties, the peptides can readily penetrate cell membranes.

The aromatic-cationic peptides useful in the present invention include a minimum of three amino acids, and preferably include a minimum of four amino acids, covalently joined by peptide bonds.

The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein, the term "amino acid" is used to refer to any organic molecule that contains at least one amino group and at least one carboxyl group. Preferably, at least one amino group is at the a position relative to the carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present invention can contain one or more non-naturally occurring amino acids. The non-naturally occurring amino acids may be L-, dextrorotatory (D), or mixtures thereof. The peptide may have no amino acids that are naturally occurring.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids.

If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

In suitable embodiments, the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

In suitable embodiments, the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present invention have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, may be amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

```
Lys-D-Arg-Tyr-NH2,

D-Tyr-Trp-Lys-NH2,

Trp-D-Lys-Tyr-Arg-NH2,

Tyr-His-D-Gly-Met,

Tyr-D-Arg-Phe-Lys-Glu-NH2,

Met-Tyr-D-Lys-Phe-Arg,

D-His-Glu-Lys-Tyr-D-Phe-Arg,

Lys-D-Gln-Tyr-Arg-D-Phe-Trp-NH2,

Phe-D-Arg-Lys-Trp-Tyr-D-Arg-His,

Gly-D-Phe-Lys-Tyr-His-D-Arg-Tyr-NH2,

Val-D-Lys-His-Tyr-D-Phe-Ser-Tyr-Arg-NH2,

Trp-Lys-Phe-D-Asp-Arg-Tyr-D-His-Lys,

Lys-Trp-D-Tyr-Arg-Asn-Phe-Tyr-D-His-NH2,

Thr-Gly-Tyr-Arg-D-His-Phe-Trp-D-His-Lys,

Asp-D-Trp-Lys-Tyr-D-His-Phe-Arg-D-Gly-Lys-NH2,

D-His-Lys-Tyr-D-Phe-Glu-D-Asp-D-His-D-Lys-Arg-Trp-
NH2,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-
Phe,

Phe-Phe-D-Tyr-Arg-Glu-Asp-D-Lys-Arg-D-Arg-His-Phe-
NH2,

Phe-Tyr-Lys-D-Arg-Trp-His-D-Lys-D-Lys-Glu-Arg-D-

Tyr-Thr,

Tyr-Asp-D-Lys-Tyr-Phe-D-Lys-D-Arg-Phe-Pro-D-Tyr-
His-Lys,

Glu-Arg-D-Lys-Tyr-D-Val-Phe-D-His-Trp-Arg-D-Gly-
Tyr-Arg-D-Met-NH2,

Arg-D-Leu-D-Tyr-Phe-Lys-Glu-D-Lys-Arg-D-Trp-Lys-
D-Phe-Tyr-D-Arg-Gly,

D-Glu-Asp-Lys-D-Arg-D-His-Phe-Phe-D-Val-Tyr-Arg-
Tyr-D-Tyr-Arg-His-Phe-NH2,

Asp-Arg-D-Phe-Cys-Phe-D-Arg-D-Lys-Tyr-Arg-D-Tyr-
Trp-D-His-Tyr-D-Phe-Lys-Phe,

His-Tyr-D-Arg-Trp-Lys-Phe-D-Asp-Ala-Arg-Cys-D-Tyr-
His-Phe-D-Lys-Tyr-His-Ser-NH2,

Gly-Ala-Lys-Phe-D-Lys-Glu-Arg-Tyr-His-D-Arg-D-Arg-
Asp-Tyr-Trp-D-His-Trp-His-D-Lys-Asp, and Thr-Tyr-Arg-D-Lys-Trp-Tyr-Glu-Asp-D-Lys-D-Arg-His-
Phe-D-Tyr-Gly-Val-Ile-D-His-Arg-Tyr-Lys-NH2.
```

In some embodiments, peptides useful in the methods of the present invention are those peptides which have a tyrosine residue or a tyrosine derivative. Preferred derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltryosine (Hmt).

In one embodiment, the peptide has the formula Tyr-D-Arg-Phe-Lys-NH2 (referred to herein as SS-01). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH2 (referred to herein as SS-02).

In a suitable embodiment, the amino acid residue at the N-terminus is arginine. An example of such a peptide is D-Arg-2'6'Dmt-Lys-Phe-NH2 (referred to herein as SS-31).

In another embodiment, the amino acid at the N-terminus is phenylalanine or its derivative. Preferred derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp). An example of such a peptide is Phe-D-Arg-Phe-Lys-NH2 (referred to herein as SS-20). In one embodiment, the amino acid sequence of SS-02 is rearranged such that Dmt is not at the N-terminus. An example of such an aromatic-cationic peptide has the formula D-Arg-2'6'Dmt-Lys-Phe-NH2 (SS-31).

In yet another embodiment, the aromatic-cationic peptide has the formula Phe-D-Arg-Dmt-Lys-NH2 (referred to herein as SS-30). Alternatively, the N-terminal phenylalanine can be a derivative of phenylalanine such as 2',6'-dimethylphenylalanine (2'6'Dmp). SS-01 containing 2',6'-dimethylphenylalanine at amino acid position one has the formula 2',6'-Dmp-D-Arg-Dmt-Lys-NH2.

SS-20, SS-31, and their derivatives can further include functional analogs. A peptide is considered a functional analog of SS-20 or SS-31 if the analog has the same function as SS-20 or SS-31. The analog may, for example, be a substitution variant of SS-01 or SS-31, wherein one or more amino acid is substituted by another amino acid.

Suitable substitution variants of SS-20 or SS-31 include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide. Examples of analogs useful in the practice of the present invention include, but are not limited to, the aromatic-cationic peptides shown in Table 5.

TABLE 5

Examples of Peptide Analogs

| Amino Acid Position 1 | Amino Acid Position 2 | Amino Acid Position 3 | Amino Acid Position 4 | Amino Acid Position 5 | Amino Acid Position 6 | Amino Acid Position 7 | C-Terminal Modification |
|---|---|---|---|---|---|---|---|
| D-Arg | Dmt | Lys | Phe | | | | $NH_2$ |
| D-Arg | Dmt | Phe | Lys | | | | $NH_2$ |
| D-Arg | Phe | Lys | Dmt | | | | $NH_2$ |
| D-Arg | Phe | Dmt | Lys | | | | $NH_2$ |
| D-Arg | Lys | Dmt | Phe | | | | $NH_2$ |
| D-Arg | Lys | Phe | Dmt | | | | $NH_2$ |
| D-Arg | Dmt | Lys | Phe | Cys | | | $NH_2$ |
| D-Arg | Dmt | Lys | Phe | Glu | Cys | Gly | $NH_2$ |
| D-Arg | Dmt | Lys | Phe | Ser | Cys | | $NH_2$ |
| D-Arg | Dmt | Lys | Phe | Gly | Cys | | $NH_2$ |
| Phe | Lys | Dmt | D-Arg | | | | $NH_2$ |
| Phe | Lys | D-Arg | Dmt | | | | $NH_2$ |
| Phe | D-Arg | Phe | Lys | | | | $NH_2$ |
| Phe | D-Arg | Phe | Lys | Cys | | | $NH_2$ |
| Phe | D-Arg | Phe | Lys | Glu | Cys | Gly | $NH_2$ |
| Phe | D-Arg | Phe | Lys | Sar | Cys | | $NH_2$ |
| Phe | D-Arg | Phe | Lys | Gly | Cys | | $NH_2$ |
| Phe | D-Arg | Dmt | Lys | | | | $NH_2$ |
| Phe | D-Arg | Dmt | Lys | Cys | | | $NH_2$ |
| Phe | D-Arg | Dmt | Lys | Glu | Cys | Gly | $NH_2$ |
| Phe | D-Arg | Dmt | Lys | Ser | Cys | | $NH_2$ |
| Phe | D-Arg | Dmt | Lys | Gly | Cys | | $NH_2$ |
| Phe | D-Arg | Lys | Dmt | | | | $NH_2$ |
| Phe | Dmt | D-Arg | Lys | | | | $NH_2$ |
| Phe | Dmt | Lys | D-Arg | | | | $NH_2$ |
| Lys | Phe | D-Arg | Dmt | | | | $NH_2$ |
| Lys | Phe | Dmt | D-Arg | | | | $NH_2$ |
| Lys | Dmt | D-Arg | Phe | | | | $NH_2$ |
| Lys | Dmt | Phe | D-Arg | | | | $NH_2$ |
| Lys | D-Arg | Phe | Dmt | | | | $NH_2$ |
| Lys | D-Arg | Dmt | Phe | | | | $NH_2$ |
| D-Arg | Dmt | D-Arg | Phe | | | | $NH_2$ |
| D-Arg | Dmt | D-Arg | Dmt | | | | $NH_2$ |
| D-Arg | Dmt | D-Arg | Tyr | | | | $NH_2$ |
| D-Arg | Dmt | D-Arg | Trp | | | | $NH_2$ |
| Trp | D-Arg | Phe | Lys | | | | $NH_2$ |
| Trp | D-Arg | Tyr | Lys | | | | $NH_2$ |
| Trp | D-Arg | Trp | Lys | | | | $NH_2$ |
| Trp | D-Arg | Dmt | Lys | | | | $NH_2$ |
| D-Arg | Trp | Lys | Phe | | | | $NH_2$ |
| D-Arg | Trp | Phe | Lys | | | | $NH_2$ |
| D-Arg | Trp | Lys | Dmt | | | | $NH_2$ |
| D-Arg | Trp | Dmt | Lys | | | | $NH_2$ |
| D-Arg | Lys | Trp | Phe | | | | $NH_2$ |
| D-Arg | Lys | Trp | Dmt | | | | $NH_2$ |
| Cha | D-Arg | Phe | Lys | | | | $NH_2$ |
| Ala | D-Arg | Phe | Lys | | | | $NH_2$ |

Cha = cyclohexyl

Under certain circumstances, it may be advantageous to use a peptide that also has opioid receptor agonist activity. Examples of analogs useful in the practice of the present invention include, but are not limited to, the aromatic-cationic peptides shown in Table 6.

TABLE 6

Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | $NH_2$ |
| Tyr | D-Arg | Phe | Orn | | $NH_2$ |
| Tyr | D-Arg | Phe | Dab | | $NH_2$ |
| Tyr | D-Arg | Phe | Dap | | $NH_2$ |
| Tyr | D-Arg | Phe | Lys | Cys | $NH_2$ |
| 2'6'Dmt | D-Arg | Phe | Lys | | $NH_2$ |
| 2'6'Dmt | D-Arg | Phe | Lys | Cys | $NH_2$ |
| 2'6'Dmt | D-Arg | Phe | Lys-NH(CH$_2$)$_2$—NH-dns | | $NH_2$ |
| 2'6'Dmt | D-Arg | Phe | Lys-NH(CH$_2$)$_2$—NH-atn | | $NH_2$ |
| 2'6'Dmt | D-Arg | Phe | dnsLys | | $NH_2$ |
| 2'6'Dmt | D-Cit | Phe | Lys | | $NH_2$ |
| 2'6'Dmt | D-Cit | Phe | Lys | Cys | $NH_2$ |
| 2'6'Dmt | D-Cit | Phe | Ahp | | $NH_2$ |
| 2'6'Dmt | D-Arg | Phe | Orn | | $NH_2$ |
| 2'6'Dmt | D-Arg | Phe | Dab | | $NH_2$ |
| 2'6'Dmt | D-Arg | Phe | Dap | | $NH_2$ |
| 2'6'Dmt | D-Arg | Phe | Ahp(2-aminoheptanoic acid) | | $NH_2$ |
| Bio-2'6'Dmt | D-Arg | Phe | Lys | | $NH_2$ |
| 3'5'Dmt | D-Arg | Phe | Lys | | $NH_2$ |
| 3'5'Dmt | D-Arg | Phe | Orn | | $NH_2$ |
| 3'5'Dmt | D-Arg | Phe | Dab | | $NH_2$ |
| 3'5'Dmt | D-Arg | Phe | Dap | | $NH_2$ |
| Tyr | D-Arg | Tyr | Lys | | $NH_2$ |
| Tyr | D-Arg | Tyr | Orn | | $NH_2$ |
| Tyr | D-Arg | Tyr | Dab | | $NH_2$ |
| Tyr | D-Arg | Tyr | Dap | | $NH_2$ |
| 2'6'Dmt | D-Arg | Tyr | Lys | | $NH_2$ |
| 2'6'Dmt | D-Arg | Tyr | Orn | | $NH_2$ |
| 2'6'Dmt | D-Arg | Tyr | Dab | | $NH_2$ |
| 2'6'Dmt | D-Arg | Tyr | Dap | | $NH_2$ |
| 2'6'Dmt | D-Arg | 2'6'Dmt | Lys | | $NH_2$ |
| 2'6'Dmt | D-Arg | 2'6'Dmt | Orn | | $NH_2$ |
| 2'6'Dmt | D-Arg | 2'6'Dmt | Dab | | $NH_2$ |
| 2'6'Dmt | D-Arg | 2'6'Dmt | Dap | | $NH_2$ |
| 3'5'Dmt | D-Arg | 3'5'Dmt | Arg | | $NH_2$ |
| 3'5'Dmt | D-Arg | 3'5'Dmt | Lys | | $NH_2$ |
| 3'5'Dmt | D-Arg | 3'5'Dmt | Orn | | $NH_2$ |
| 3'5'Dmt | D-Arg | 3'5'Dmt | Dab | | $NH_2$ |
| 2'6'Dmt | D-Arg | 2'6'Dmt | Lys | Cys | $NH_2$ |
| Tyr | D-Lys | Phe | Dap | | $NH_2$ |
| Tyr | D-Lys | Phe | Arg | | $NH_2$ |
| Tyr | D-Lys | Phe | Arg | Cys | $NH_2$ |
| Tyr | D-Lys | Phe | Lys | | $NH_2$ |
| Tyr | D-Lys | Phe | Orn | | $NH_2$ |
| 2'6'Dmt | D-Lys | Phe | Dab | | $NH_2$ |
| 2'6'Dmt | D-Lys | Phe | Dap | | $NH_2$ |
| 2'6'Dmt | D-Lys | Phe | Arg | | $NH_2$ |
| 2'6'Dmt | D-Lys | Phe | Lys | | $NH_2$ |
| 3'5'Dmt | D-Lys | Phe | Orn | | $NH_2$ |
| 3'5'Dmt | D-Lys | Phe | Dab | | $NH_2$ |
| 3'5'Dmt | D-Lys | Phe | Dap | | $NH_2$ |
| 3'5'Dmt | D-Lys | Phe | Arg | | $NH_2$ |
| 3'5'Dmt | D-Lys | Phe | Arg | Cys | $NH_2$ |
| Tyr | D-Lys | Tyr | Lys | | $NH_2$ |
| Tyr | D-Lys | Tyr | Orn | | $NH_2$ |
| Tyr | D-Lys | Tyr | Dab | | $NH_2$ |
| Tyr | D-Lys | Tyr | Dap | | $NH_2$ |
| 2'6'Dmt | D-Lys | Tyr | Lys | | $NH_2$ |
| 2'6'Dmt | D-Lys | Tyr | Orn | | $NH_2$ |
| 2'6'Dmt | D-Lys | Tyr | Dab | | $NH_2$ |
| 2'6'Dmt | D-Lys | Tyr | Dap | | $NH_2$ |
| 2'6'Dmt | D-Lys | 2'6'Dmt | Lys | | $NH_2$ |
| 2'6'Dmt | D-Lys | 2'6'Dmt | Orn | | $NH_2$ |
| 2'6'Dmt | D-Lys | 2'6'Dmt | Dab | | $NH_2$ |
| 2'6'Dmt | D-Lys | 2'6'Dmt | Dap | | $NH_2$ |
| 2'6'Dmt | D-Arg | Phe | dnsDap | | $NH_2$ |
| 2'6'Dmt | D-Arg | Phe | atnDap | | $NH_2$ |
| 3'5'Dmt | D-Lys | 3'5'Dmt | Lys | | $NH_2$ |
| 3'5'Dmt | D-Lys | 3'5'Dmt | Orn | | $NH_2$ |
| 3'5'Dmt | D-Lys | 3'5'Dmt | Dab | | $NH_2$ |

TABLE 6-continued

Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |
| 3'5'Dmt | D-Lys | Phe | Arg | | NH$_2$ |
| 3'5'Dmt | D-Orn | Phe | Arg | | NH$_2$ |
| Tyr | D-Lys | Tyr | Arg | | NH$_2$ |
| Tyr | D-Orn | Tyr | Arg | | NH$_2$ |
| Tyr | D-Dab | Tyr | Arg | | NH$_2$ |
| Tyr | D-Dap | Tyr | Arg | | NH$_2$ |
| 2'6'Dmt | D-Arg | 2'6'Dmt | Arg | | NH$_2$ |
| 2'6'Dmt | D-Lys | 2'6'Dmt | Arg | | NH$_2$ |
| 2'6'Dmt | D-Orn | 2'6'Dmt | Arg | | NH$_2$ |
| 2'6'Dmt | D-Dab | 2'6'Dmt | Arg | | NH$_2$ |
| 3'5'Dmt | D-Dap | 3'5'Dmt | Arg | | NH$_2$ |
| 3'5'Dmt | D-Arg | 3'5'Dmt | Arg | | NH$_2$ |
| 3'5'Dmt | D-Lys | 3'5'Dmt | Arg | | NH$_2$ |
| 3'5'Dmt | D-Orn | 3'5'Dmt | Arg | | NH$_2$ |
| Mmt | D-Arg | Phe | Lys | | NH$_2$ |
| Mmt | D-Arg | Phe | Orn | | NH$_2$ |
| Mmt | D-Arg | Phe | Dab | | NH$_2$ |
| Mmt | D-Arg | Phe | Dap | | NH$_2$ |
| Tmt | D-Arg | Phe | Lys | | NH$_2$ |
| Tmt | D-Arg | Phe | Orn | | NH$_2$ |
| Tmt | D-Arg | Phe | Dab | | NH$_2$ |
| Tmt | D-Arg | Phe | Dap | | NH$_2$ |
| Hmt | D-Arg | Phe | Lys | | NH$_2$ |
| Hmt | D-Arg | Phe | Orn | | NH$_2$ |
| Hmt | D-Arg | Phe | Dab | | NH$_2$ |
| Hmt | D-Arg | Phe | Dap | | NH$_2$ |
| Mmt | D-Lys | Phe | Lys | | NH$_2$ |
| Mmt | D-Lys | Phe | Orn | | NH$_2$ |
| Mmt | D-Lys | Phe | Dab | | NH$_2$ |
| Mmt | D-Lys | Phe | Dap | | NH$_2$ |
| Mmt | D-Lys | Phe | Arg | | NH$_2$ |
| Tmt | D-Lys | Phe | Lys | | NH$_2$ |
| Tmt | D-Lys | Phe | Orn | | NH$_2$ |
| Tmt | D-Lys | Phe | Dab | | NH$_2$ |
| Tmt | D-Lys | Phe | Dap | | NH$_2$ |
| Tmt | D-Lys | Phe | Arg | | NH$_2$ |
| Hmt | D-Lys | Phe | Lys | | NH$_2$ |
| Hmt | D-Lys | Phe | Orn | | NH$_2$ |
| Hmt | D-Lys | Phe | Dab | | NH$_2$ |
| Hmt | D-Lys | Phe | Dap | | NH$_2$ |
| Hmt | D-Lys | Phe | Arg | | NH$_2$ |
| Mmt | D-Lys | Phe | Arg | | NH$_2$ |
| Mmt | D-Orn | Phe | Arg | | NH$_2$ |
| Mmt | D-Dab | Phe | Arg | | NH$_2$ |
| Mmt | D-Dap | Phe | Arg | | NH$_2$ |
| Mmt | D-Arg | Phe | Arg | | NH$_2$ |
| Tmt | D-Lys | Phe | Arg | | NH$_2$ |
| Tmt | D-Orn | Phe | Arg | | NH$_2$ |
| Tmt | D-Dab | Phe | Arg | | NH$_2$ |
| Tmt | D-Dap | Phe | Arg | | NH$_2$ |
| Tmt | D-Arg | Phe | Arg | | NH$_2$ |
| Hmt | D-Lys | Phe | Arg | | NH$_2$ |
| Hmt | D-Orn | Phe | Arg | | NH$_2$ |
| Hmt | D-Dab | Phe | Arg | | NH$_2$ |
| Hmt | D-Dap | Phe | Arg | | NH$_2$ |
| Hmt | D-Arg | Phe | Arg | | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine TABLE 6-continued Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---| dnsDap = β-dansyl-L-α,β-diaminopropionic acid
atnDap = β-anthraniloyl-L-α,β-diaminopropionic acid
Bio = biotin The amino acids of the peptides shown in Tables 5 and 6 may be in either the L- or the D-configuration.

Synthesis of the Peptides

The peptides useful in the methods of the present invention may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis," *Methods Enzymol.* 289, Academic Press, Inc, New York (1997).

Methods of Protecting and Treating Renal Injury in a Subject

General. The aromatic-cationic peptides described herein are useful in protecting a subject's kidney from renal injury. Acute renal injury (ARI) refers to a reduction of renal function to excrete waste from a patient's blood. ARI is typically characterized as including a decline of glomerular filtration rate (GFR) to a level so low that little or no urine is formed. Therefore, substances that the kidney usually eliminates remain in the body.

The causes of ARI are multifactorial, but they may be classified into three categories: (1) prerenal ARI, in which the kidneys fail to receive adequate blood supply, e.g., due to fall in systemic blood pressure as in shock/cardiac arrest, or subsequent to hemorrhage; (2) intrinsic ARI, in which the failure occurs within the kidney, e.g., due to drug-induced toxicity; and (3) postrenal ARI, caused by impairment of urine flow out of the kidney, as in ureteral obstruction due to kidney stones or bladder/prostate cancer. ARI may be associated with any one or a combination of these categories.

Early diagnosis and treatment of acute renal injury can in some cases prevent progression of acute renal injury to chronic renal failure. ARI is accompanied by an inflammatory response that if unchecked can lead to renal fibrosis and chronic renal failure. Chronic renal failure (CRF) refers to a progressive loss of renal function and irreversible kidney damage.

Methods for assessing renal function are well known in the art and include, but are not limited to, measurements of blood systemic and glomerular capillary pressure, proteinuria (e.g., albuminuria), microscopic and macroscopic hematuria, serum creatinine level (e.g., one formula for estimating renal function in humans equates a creatinine level of 2.0 mg/dl to 50 percent of normal kidney function and 4.0 mg/dl to 25 percent), decline in the glomerular filtration rate (GFR) (e.g., rate of creatinine clearance), and degree of tubular damage. For example, such assessment may include evaluating at least one kidney function using biological and/or physiological parameters such as serum creatinine level, creatinine clearance rate, 24-hour urinary protein secretion, glomerular filtration rate (GFR), urinary albumin creatinine ratio, albumin excretion rate, and renal biopsy.

Methods for assessing deterioration of renal structure are also well known. Illustrative methods are described in the Examples. Such methods include renal imaging (e.g., MRI, ultrasound), or histological evaluation of renal biopsy. In some embodiments, the methods of the invention reduce deterioration of renal structure as judged, for example, by the extent of tubulointerstitial or glomerular damage and/or the degree of renal fibrosis (e.g., deposition of collagen and fibronectin).

For a detailed review of renal function and disease states, see *The Kidney Physiology and Pathophysiology*, eds. Seldin et al., 3rd ed., Lippincott Williams & Wilkins Publishers, 2000. Normally, less than 0.15 g of protein is excreted into the urine per 24 hour period. Almost all types of kidney disease cause mild (up to 500 mg per day) to moderate (up to 4 g per day) protein leakage into the urine. The normal concentration of albumin in the urine is less than 1.0 mg/dl. Generally, 30-300 mg/dl urinary albumin is considered microalbuminuria, and 300 mg/dl and up is considered macroalbuminuria. The normal values of serum creatinine are 0.6-1.5 mg/dl for men and 0.6-1.1 mg/dl for women.

Methods of Preventing or Treating ARI Caused by Ischemia. An example of a condition in which kidneys fail to receive adequate blood supply to the kidney is ischemia. Ischemia is a major cause of ARI. Ischemia of one or both kidneys is a common problem experienced during aortic surgery, renal transplantation, or during cardiovascular anesthesia. Surgical procedures involving clamping of the aorta and/or renal arteries, e.g., surgery for supra- and juxtarenal abdominal aortic aneurysms and renal transplantation, are also particularly liable to produce renal ischemia, leading to significant postoperative complications and early allograft rejection. In high-risk patients undergoing these forms of surgery, the incidence of renal dysfunction has been reported to be as high as 50%.

Ischemia may be caused by loss of blood, loss of fluid from the body as a result of severe diarrhea or burns, shock, and ischemia associated with storage of the donor kidney prior to transplantation. In these situations, the blood flow to the kidney may be reduced to a dangerously low level for a time period great enough to cause ischemic injury to the tubular epithelial cells, sloughing off of the epithelial cells into the tubular lumen, obstruction of tubular flow that leads to loss of glomerular filtration and acute renal injury.

Subjects may also become vulnerable to ARI after receiving anesthesia, surgery, or α-adrenergic agonists because of related systemic or renal vasoconstriction. Additionally, systemic vasodilation caused by anaphylaxis, and anti-hypertensive drugs, sepsis or drug overdose may also cause ARI because the body's natural defense is to shut down, i.e., vasoconstriction of non-essential organs such as the kidneys.

Accordingly, in one embodiment, a subject at risk for ARI may be a subject undergoing an interruption or reduction of blood supply or blood pressure to the kidney. These subjects may be administered the aromatic-cationic peptides of the invention prior to or simultaneously with such interruption or reduction of blood supply. Likewise, aromatic-cationic peptides may be administered after the therapeutic agent to treat ischemia.

Methods of Preventing or Treating ARI Caused by Drug-Induced Toxicity. Another cause of ARI includes drug-induced toxicity. For example, nephrotoxins can cause direct toxicity on tubular epithelial cells. Nephrotoxins include, but are not limited to, therapeutic drugs, e.g., cisplatin, gentamicin, cephaloridine, cyclosporin, amphotericin, radiocontrast dye (described in further detail below), pesticides (e.g., paraquat), and environmental contaminants (e.g., trichloriethylene and dichloroacetylene). Other examples include puromycin aminonucleoside (PAN); aminoglycosides, such as gentamicin; cephalosporins, such as cephaloridine; calcineurin inhibitors, such as tacrolimus or sirolimus. Drug-induced nephrotoxicity may also be caused by non-steroidal anti-inflammatories, anti-retrovirals, anti-cytokines, immunosuppressants, oncological drugs or ACE inhibitors. The drug-induced nephrotoxicity may further be caused by nalgesic abuse, ciprofloxacin, clopidogrel, cocaine, cox-2 inhibitors, diuretics, foscamet, gold, ifosfamide, immunoglobin, Chinese herbs, interferon, lithium, mannitol, mesalamine, mitomycin, nitrosoureas, penicillamine, penicillins, pentamidine, quinine, rifampin, streptozocin, sulfonamides, ticlopidine, triamterene, valproic acid, doxorubicin, glycerol, cidofovir, tobramycin, neomycin sulfate, colistimethate, vancomycin, amikacin, cefotaxime, cisplatin, acyclovir, lithium, interleukin-2, cyclosporin or indinavir.

In addition to direct toxicity on tubular epithelial cells, some nephrotoxins also reduce renal perfusion, causing injury to zones known to have limited oxygen availability (inner medullary region). Such nephrotoxins include amphotericin and radiocontrast dye. Renal failure can result even from clinically relevant doses of these drugs when combined with ischemia, volume depletion, obstruction, or infection. An example is the use of radiocontrast dye in patients with impaired renal function. The incidence of contrast-dye nephropathy (CIN) is 3-8% in the normal patient, but increases to 25% for patients with diabetes mellitus. Most cases of ARI occur in patients with predisposing comorbidities (McCombs, P. R. & Roberts, B. *Surg Gynecol Obstet,* 148:175-178 (1979)).

Accordingly, in one embodiment, a subject at risk for ARI may be receiving one or more therapeutic drugs that have a nephrotoxic effect. These subjects may be administered the aromatic-cationic peptides of the invention prior to or simultaneously with such therapeutic agents. Likewise, aromatic-cationic peptides may be administered after the therapeutic agent to treat nephrotoxicity.

Methods of Preventing or Treating ARI Caused by Radio-contrast Agents. In one embodiment, the aromatic-cationic peptides of the invention are administered to a subject at risk for contrast-induced nephropathy (CIN), in order to protect the subject from this condition. CIN is an important cause of acute renal failure. CIN is defined as acute renal failure occurring within 48 h of exposure to intravascular radiographic contrast material. CIN remains a common complication of radiographic procedures.

CIN arises when a subject is exposed to radiocontrast dye, such as during coronary, cardiac, or neuro-angiography procedures. Contrast dye is essential for many diagnostic and interventional procedures because it enables doctors to visualize blocked body tissues. Subjects at greatest risk for CIN are the elderly, and those with diabetes, chronic kidney disease, or advanced heart failure. The serum creatinine test can be used to monitor the onset of CIN, monitor treatment, as well as monitor the effectiveness of the peptides of the present invention in protecting subjects from the onset of CIN.

In some embodiments, the aromatic-cationic peptides of the invention are administered to a subject prior to or simultaneously with the administration of a contrast agent in order to provide protection against CIN. For example, the subject may receive the peptides from about 1 to 2 hours, about 1 to 6 hours, about 1 to 12 hours, about 1 to 24 hours, or about 1 to 48 hours prior to receiving the contrast agent. Likewise, the subject may be administered the peptides at about the same time as the contrast agent. Moreover, administration of the peptides to the subject may continue following administration of the contrast agent. In some embodiments, the subject may continue to receive the peptide at intervals of about 1, 2, 3, 4, 5, 6, 7, 8, 12, 24, and 48 hours following administration of the contrast agent, in order to provide a protective or prophylactic effect against CIN.

In some embodiments, the aromatic-cationic peptides of the invention are administered to a subject after administration of a contrast agent in order to treat CIN. For example, the subject may receive the peptides from about 1 to 2 hours, about 1 to 6 hours, about 1 to 12 hours, about 1 to 24 hours, about 1 to 48 hours, or about 1 to 72 hours after receiving the contrast agent. For instance, the subject may exhibit one or more signs or symptoms of CIN prior to receiving the peptides of the invention, such as increased serum creatinine levels and/or decreased urine volume. Administration of the peptides of the invention improves one or more of these indicators of kidney function in the subject compared to a control subject not administered the peptides.

Types of Contrast Agents. The incidence of CIN is influenced by the chemical structure and particularly by the osmolarity and the ionic (or non-ionic) structure of the contrast agent used (See Zirogiannis et al., "Contrast media induced nephropathy in patients undergoing cardiac catheterization." *Hellenic J Cardiol,* 45:07-113 (2004)). A "contrast agent" as used herein, refers to a compound employed to improve the visibility of internal body structures in an image, e.g., a CT or MRI scan. The term "contrast agent" is also referred to herein as an "imaging agent." Imaging agents include those known in the art, such as dyes, fluorescent dyes, gold particles, iron oxide particles and other contrast agents including paramagnetic molecules, x-ray attenuating compounds (for CT and x-ray), contrast agents for ultrasound, γ-ray emitting isotopes (Scintigraphy), and positron-emitting isotopes (PET). Contrast agents can be administered to the subject by, for example, parenteral injection (e.g., intravenously, intra-arterially, intra-thecally, intra-abdominally, subcutaneously, intramuscularly), orally (e.g., as a tablet or a drink), rectally, or via inhalation.

For example, an X-ray contrast agent can comprise barium sulfate, or can comprise iodine in an organic (non-ionic) compound or in an ionic compound. Examples of iodine contrast agents include those shown in Table 7.

TABLE 7

Exemplary Iodinated Contrast Agents

| Name | Type | Iodine Content | Osmolality | Level |
|---|---|---|---|---|
| Diatrizoate (Hypaque 50) | Ionic Monomer | 300 | 1550 | High Osmolar |
| Metrizoate (Isopaque Coronar 370) | Ionic | 370 | 2100 | High Osmolar |
| Ioxaglate (Hexabrix) | Ionic dimer | 320 | 580 | Low Osmolar |
| Iopamidol (Isovue 370) | Non-ionic monomer | 370 | 796 | Low Osmolar |

TABLE 7-continued

Exemplary Iodinated Contrast Agents

| Name | Type | Iodine Content | Osmolality | Level |
|---|---|---|---|---|
| Iohexol (Omnipaque 350) | Non-ionic | 350 | 884 | Low Osmolar |
| Ioxilan (Oxilan) | Non-ionic | | | Low Osmolar |
| Iopromide | Non-ionic | | | Low Osmolar |
| Iodixanol (Visipaque 320) | Non-ionic dimer | 320 | 290 | Iso Osmolar |

An MRI contrast agent can comprise a paramagnetic contrast agent (such as a gadolinium compound), a super paramagnetic contrast agent (such as iron oxide nanoparticles), a diamagnetic agent (such as barium sulfate), and combinations thereof. Metal ions preferred for MRI include those with atomic numbers 21-29, 39-47, or 57-83, and, more preferably, a paramagnetic form of a metal ion with atomic numbers 21-29, 42, 44, or 57-83. Particularly preferred paramagnetic metal ions are selected from the group consisting of Gd(III), Fe(III), Mn(II and III), Cr(III), Cu(II), Dy(III), Tb(III and IV), Ho(III), Er(III), Pr(III) and Eu(II and III). Gd(III) is particularly useful. Note that as used herein, the term "Gd" is meant to convey the ionic form of the metal gadolinium; such an ionic form can be written as GD(III), GD3+, etc. with no difference in ionic form contemplated. A CT contrast agent can comprise iodine (ionic or non-ionic formulations), barium, barium sulfate, Gastrografin (a diatrizoate meglumine and diatrizoate sodium solution), and combinations thereof. In another embodiment, a PET or SPECT contrast agent can comprise a metal chelate.

As stated above, contrast agents include, but are not limited to, molecules bearing one or more iodine moieties. Iodine may be bound either in an organic compound or an ionic compound. The earliest contrast agents were ionic, containing a sodium atom that dissociated from the iodine in aqueous solution. Organic compounds have fewer side effects as they do not dissociate into component molecules.

Iodinated contrast media may be divided into water-soluble, water-insoluble, and oily contrast media. Water-insoluble contrast media include aqueous suspension of propyliodone (Dionosil®), used in bronchography. Oily contrast media include Lipiodol, a stable compound of 40% iodine in poppy seed oil, and Lipiodol Ultra® Fluid and Ethiodol®, ethyl esters of iodinated fatty acids of poppy seed oil containing 48% and 37% iodine, respectively. These oils are used for lymphography, and by some also for hysterosalpingography. Iodophenylundecylic acid (iophendylate) is a contrast medium for oil myelography (brand names: Pantopaque®, Myodil®).

The water-soluble contrast media represent by far the largest group of iodinated contrast media. These contrast media may be classified into high-osmolality, low-osmolality, and iso-osmolality contrast media. The osmolality is related to some of the adverse events of these contrast media. Monomeric ionic contrast media constitute two main groups, oral cholegraphic contrast media and uro/angiographic media. Examples of these media include: acetrizoate (Diaginol®, Urokon®); diatrizoate (Angiografin®, Hypaque®, Renografin®, Urografin®, Urovison®); iodamide (Uromiro®); ioglicate (Rayvist®); iothalamate (Conray®); ioxithalamate (Telebrix®); and metrizoate (Isopaque®, Triosil®).

The uro/angiographic media are all salts of derivatives of tri-iodinated benzoic acid, and differ only in the side-chains at position 3 and 5. The cations of the salts are mainly either sodium or meglumine, or a mixture of both. Sodium salts are generally more toxic to vascular endothelium and to blood-brain barrier and neural tissue than meglumine. A mixture of sodium and meglumine has lower cardiotoxicity than either salts alone. Some manufacturers have partially replaced sodium with calcium and magnesium to reduce toxicity.

The ionic monomeric contrast media for intravascular use are so-called high-osmolar contrast media (HOCM), having an osmolality seven to eight times that of plasma in ordinary clinical use. This hyperosmolality is responsible for several subjective and objective adverse effects such as pain, endothelial damage, thrombosis and thrombophlebitis, disturbance of the blood-brain barrier, bradycardia in cardioangiography and increased pressure in the pulmonary circulation. The introduction of low-osmolar contrast media (LOCM) has substantially reduced these side effects. Osmolality is dependent upon the number of molecules per volume unit solution. The ionic monomeric agents are salts that dissociate into two molecules, one anion containing the radiopaque property due to three iodine atoms, and one cation without radiopaque properties. These agents are also called 3:2 or ratio 1.5 agents (three iodine atoms per two molecules). There are three strategies to obtain contrast media with lower osmolality without loss of X-ray absorption: the production of 1) non-ionic monomers, 2) ionic dimers or 3) non-ionic dimers. Non-ionic contrast media do not dissociate and their water-solubility is generally achieved by several hydrophilic hydroxyl groups. Tri-iodinated non-ionic monomers have approximately half the osmolality of that of ionic monomers (they are 3:1 or ratio 3 agents). Several agents are available in convenient ready-to-use solutions of non-ionic monomeric contrast media have appeared, and include: metrizamide (Amipaque®); iohexol (Omnipaque®); iopamidol (Iopamiro®, Isovue®, Niopam®, Solutrast®); iopentol (Imagopaque®); iopromide (Ultravist®); and ioversol (Optiray®).

These contrast media have hydrophilic hydroxyl groups attached to all three side chains, a feature that has also contributed to reducing their toxicity. In addition to osmolality, toxicity is also dependent upon chemical structure, an intrinsic toxicity sometimes named chemotoxicity. Although the mechanism of contrast medium toxicity is not completely understood, it is believed that chemotoxicity is related to the protein-binding capacity of the medium, which is caused by non-specific weak interactions between the contrast medium and surrounding biological molecules (e.g., enzymes). The interaction is mediated through electrical forces, which are present only for ionic agents, and through interaction between hydrophobic portions of the molecule, which for contrast media is mainly the benzene ring. The many hydrophilic side groups of the second generation non-ionic monomers protect the inner hydrophobic benzene ring from interaction, thereby reducing chemotoxicity. The relative hydrophobicity/hydrophilicity of the molecule is called its partition coefficient, a low partition coefficient being advantageous because a high hydrophilicity contributes to low protein binding.

Dimeric contrast media with two tri-iodinated benzene rings constitute three main groups; ionic intravenous cholegraphic contrast media, monoacidic ionic contrast media, and non-ionic contrast media. The two latter groups both belong to the so-called low-osmolar contrast media. There is only one monoacidic ionic dimer; sodium meglumine ioxaglate (Hexabrix®). The dimeric anion has one carboxyl group, the other has been replaced by a non-ionizing side group. This gives six iodine atoms per two particles; the contrast medium is a 6:2 (=3:1) or ratio 3 agent (similar to the non-ionic monomers). Owing partly to its ionic character, partly to its fewer hydroxyl groups, ioxaglate is more toxic than the non-ionic monomers with similar osmolality (but less toxic than the ionic monomers owing to lower osmolality).

The non-ionic dimers yield six iodine atoms per molecule (ratio 6 agents). Examples of non-ionic dimer contrast media include: iotrolan (Isovist®) and iodixanol (Visipaque®). Iotrolan is nearly iso-osmolar to plasma (0.32 osm/kg $H_2O$), while iodixanol is actually hypo-osmolar to plasma. Iso-osmolarity to plasma (0.29 osm/kg $H_2O$) is achieved at any iodine concentration by addition of an appropriate amount of saline. These agents have a very low toxicity owing partly to their iso-osmolarity, partly their non-ionic character, and partly to the fact that they possess a very large number of hydroxyl groups (low partition coefficient).

The various water-soluble contrast media for urography and angiography (ionic and non-ionic monomers, non-ionic dimers) are all extracellular contrast media, and are excreted unmetabolized by glomerular filtration. Approximately 85-90% of the injected dose is found in urine within the first 6 hours; 95-100% within the first 24 hours. Generally less than 2% may be found in feces.

Non-ionic contrast agents (containing 6 iodine anions in their molecule) were believed to be less nephrotoxic than ionic contrast agents (containing 3 iodine anions in their molecule). However, in a recent study where 443 patients were randomly assigned to a non-ionic (iopamidol) and an ionic (diatrizoate) contrast agent, the incidence of CIN was not statistically different (8.2 and 10.2% respectively) (Zirogiannis et al., "Contrast media induced nephropathy in patients undergoing cardiac catheterization." *Hellenic J Cardiol* 45:107-113 (2004)). Furthermore, recent evidence also points to an association between exposure to a gadolinium-containing contrast agents during MRI studies and incidence of nephrogenic fibrosing dermopathy in patients with advanced renal disease (Agahtehrani and Moussa, *Vascular Disease Management*, 4:49-59 (2007)). Thus, regardless of the type of contrast agent, the mechanism for renal failure appears to be the same, and the aromatic-cationic peptides of the invention are useful in the prevention or treatment of ARI caused by these agents.

Additional Applications for Aromatic-Cationic Peptides in ARI. In a further embodiment, a subject in need thereof may be a subject having impairment of urine flow. Obstruction to the flow of urine can occur anywhere in the urinary tract and has many different possible causes. Such causes include kidney stones or bladder/prostate cancer. Unilateral ureteral obstruction (UUO) is a common clinical disorder associated with obstructed urine flow. It is also associated with tubular cell apoptosis, macrophage infiltration, and interstitial fibrosis. Interstitial fibrosis leads to a hypoxic environment and contributes to progressive decline in renal function despite surgical correction. Thus, a subject having or at risk for UUO may be administered the aromatic-cationic peptides of the invention to protect or treat the subject from ARI.

In yet another aspect of the invention, a method for protecting a kidney from renal fibrosis in a mammal in need thereof is provided. The method comprises administering to the mammal an effective amount of an aromatic-cationic peptide as described above. The peptides described above can be administered to a mammal in need thereof, as described above, by any method known to those skilled in the art.

The term "fibrosis" refers to abnormal processing of fibrous tissue, or fibroid or fibrous degeneration. Fibrosis can result from various injuries or diseases, and can often result from chronic transplant rejection relating to the transplantation of various organs. Fibrosis typically involves the abnormal production, accumulation, or deposition of extracellular matrix components, including overproduction and increased deposition of, for example, collagen and fibronectin. As used herein, the term "renal fibrosis" refers to fibrosis of the kidney. For example, renal fibrosis is associated with overproduction or abnormal deposition of extracellular matrix components, particularly collagen, leading to the degradation or impairment of kidney function.

In another aspect of the invention, a method for treating acute renal injury in a mammal in need thereof is provided. The method comprises administering to the mammal an effective amount of an aromatic-cationic peptide as described above. The peptides described above can be administered to a mammal in need thereof, as described above, by any method known to those skilled in the art.

The methods of the invention may be particularly useful in patients with renal insufficiency, renal failure, or end-stage renal disease attributable at least in part to a nephrotoxicity of an drug or chemical. Other indications may include creatinine clearance levels of lower than 97 (men) and 88 (women) ml/min, blood urea of 20-25 mg/dl or higher. Furthermore, the treatment may be useful in patients with microalbuminuria, macroalbuminuria, and/or proteinuria levels of over 1, 2, 3, 4, 5, 6, 7, 8, 9, or 10 g or more per a 24 hour period, and/or serum creatinine levels of about 1.0, 1.5, 2.0, 2.5, 3, 3.5, 4.0, 4.5, 5, 5.5, 6, 7, 8, 9, 10 mg/dl or higher.

The methods of the invention can be used to slow or reverse the progression of renal disease in patients whose renal function is below normal by 25%, 40%, 50%, 60%, 75%, 80%, 90% or more, relative to control subjects. In some embodiments, the methods of the invention slow the loss of renal function by at least 10%, 20%, 30%, 40%, 50%, 60%, 70%, 80%, 90%, 100% or more, relative to control subjects. In other embodiments, the methods of the invention improve the patient's serum creatinine levels, proteinuria, and/or urinary albumin excretion by at least 10%, 20%, 30%, 40%, 50%, 60%, 70%, or more, relative to control subjects. Non-limiting illustrative methods for assessing renal function are described herein and, for example, in WO 01/66140.

In another embodiment, the peptides useful in the present invention may also be used in protecting a subject's kidney from acute renal injury prior to transplantation. For example, a removed kidney can be placed in a solution containing the peptides described above. The concentration of peptides in the standard buffered solution can be easily determined by those skilled in the art. Such concentrations may be, for example, between about 0.01 µM to about 10 µM, about 0.1 µM to about 10 µM, about 1 M to about 5 µM, or about 1 µM to about 100 µM.

Methods of Treating ARI. In another aspect of the invention, the invention provides a method for treating acute renal injury in a subject in need thereof. The method comprises administering to the subject an effective amount of an aromatic-cationic peptide as described above. The peptides described above can be administered to a subject in need thereof, as described above, by any method known to those skilled in the art.

Subjects in need of protection from or treatment of acute renal injury also include subjects suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO•), superoxide anion radical ($O_2^{•-}$), nitric oxide (NO•), hydrogen peroxide ($H_2O_2$), hypochlorous acid (HOCl) and peroxynitrite anion ($ONOO^-$).

Ischemic or toxic insults can lead to a secondary condition of an acute, often reversible loss of renal function called acute tubular necrosis (ATN), which is another common cause of ARI. The course of ATN is triphasic. The initiating phase of ATN is characterized by a precipitous drop in glomerular filtration rate (GFR), triggered by ischemia and associated hemodynamic changes, and accompanied by sublethal or lethal tubular epithelial injury. The established or persistent phase of ATN is characterized by persistent reduction in GFR. Sublethal tubular injury includes loss of brush border, vacuolization and flattening of proximal tubules, and dilation of tubules. Cellular necrosis may be seen in the proximal tubule. The renal interstitium may be edematous, whereas leukocytic infiltration may be observed in the medulla. The distal tubular lumen may be occluded by casts, and distal, rather than proximal, tubular epithelial cells are more likely involved by apoptosis. Such structural and functional derangements resolve during the recovery or diuretic phase wherein reparative and regenerative responses restore renal architecture and normalize GFR.

Common mechanisms of ARI caused by ischemia and nephrotoxicants involve mitochondrial dysfunction and ATP deficits, which result in renal proximal tubular cell (RPTC) injury and necrosis. RPTCs are highly specialized both in terms of morphology and function allowing for efficient transport of water, ions and macromolecules via specific transport mechanisms. RPTCs contain very high density of mitochondria, and oxygen is used to sustain oxidative phosphorylation and synthesis of ATP, which is needed in large quantities for renal tubular transport processes. During ischemia, these transport processes are severely disrupted due to loss of intracellular ATP. Restoration of blood flow will help to limit cell death, but recovery of mitochondrial function depends on the duration of ischemia. With prolonged ischemia, there is evidence that the rate of oxidative phosphorylation continues to deteriorate despite reperfusion. Progressive ischemia leads to inhibition of several components of the mitochondrial electron transport chain, including complex I, complex V, and the adenine nucleotide translocator, and decrease in ATP production. In addition, ischemia decreases cardiolipin and cytochrome c content in cardiac mitochondria, both of which will inhibit cytochrome c oxidase activity. Thus, mitochondria can suffer damage during ischemia that would limit their capacity to generate ATP upon restoration of oxygen and substrates with reperfusion.

Furthermore, damaged mitochondria generate enormous amounts of ROS during reperfusion, and there is an excess of hydroxyl radicals as a result of iron overload following ischemia. Mitochondria are normally protected from oxidative damage by a multi-layer network of mitochondrial antioxidant systems, but they can undergo oxidative damage when ROS production exceeds the antioxidant capacity of mitochondria. ROS can initiate damage to nucleic acids, proteins and lipids in mitochondria. Protein oxidation and nitration result in altered function of many enzymes in the mitochondrial electron transport chain, while oxidation of the adenine nucleotide translocator impairs the influx of ADP into the matrix for ATP synthesis. ROS have been shown to damage renal mitochondria by enhancing membrane permeability, decreasing $F_0F_1$ATPase activity and reducing ATP production.

Mitochondrial dysfunction may therefore lead to necrosis or apoptosis. Necrosis is characterized by cell swelling and disruption of the cell membrane, leading to release of cellular contents, especially proteolytic enzymes, which may result in destruction of neighboring cells. Apoptosis, on the other hand, is defined as programmed cell death wherein the organism eliminates senescent, abnormal cells without affecting surrounding cells, and is deemed to be preferable for the survival of the organism since it eliminates dying cells by phagocytosis. The decision step between death by apoptosis or necrosis appears to be dependent on intracellular ATP content. Apoptosis involves energy-requiring steps, especially in the formation of the apoptosome complex between Apaf-1 and cytochrome c. Thus in the event of significant cellular ATP depletion, death can only occur by necrosis.

There is accumulating evidence for a role of mitochondrial ROS in the acute renal toxicity due to nephrotoxicants (Baliga et al. *Drug Metab Rev*, 31:971-997 (1999)). Cisplatin induced mitochondrial oxidative stress, decreased ATP and glutathione, cardiolipin peroxidation and apoptosis, and cisplatin nephrotoxicity can be ameliorated with hydroxyl radical scavengers (Santos, N. A., et al., *Cancer Chemother Pharmacol*, 61:145-155 (2008)). Radiocontrast dyes increase the rate of renal tubular cell apoptosis in vivo (Beeri, R., et al. Rapid DNA fragmentation from hypoxia along the thick ascending limb of rat kidneys. *Kidney Int*, 47:1806-1810 (1995)) and in vitro (Hizoh et al., *Nephrol Dial Transplant*, 13:911-918 (1998); Heinrich et al., *Radiology*, 235:843-849 (2005)). However, nephrotocixity of radiocontrast dye media cannot solely be explained by oxidative stress, and mitochondrial energetics and integrity appear to play an important role as well (Zager et al., Radiographic contrast media-induced tubular injury: evaluation of oxidant stress and plasma membrane integrity. *Kidney Int*, 64:128-139 (2003); Humes et al., *Am J Physiol*, 252:F246-255 (1987)). Oxidative damage has also been implicated in postrenal obstructive ARI, and there is evidence that the intrinsic mitochondria-mediated apoptotic pathway is involved in stretch-induced tubular cell apoptosis (Zhang, G., et al., *Exp Nephrol*, 9:71-80 (2001)).

When epithelial cells are damaged, they release inflammatory mediators, including IL-1β and TNFα, that lead to an intense inflammatory response initiated by the infiltration of leukocytes and the release of proinflammatory cytokines, chemokines and ROS. Leukocyte infiltration is observed with renal ischemia-reperfusion, ureteral obstruction, and nephrotoxins, and the inflammatory process contribute to ARI. Infiltrating lymphocytes and macrophages become activated and begin secreting profibrotic cytokines and growth factors, such as TGFβ, IL-13 and PDGF, which further activate macrophages and fibroblasts. TGFβ plays a pivotal role in epithelial-mesenchymal transition (EMT) by down-regulating E-cadherin and up-regulating α-SMA expression, and increasing collagen production. Fibrosis occurs when the synthesis of new collagen by myofibroblasts exceeds the rate at which it is degraded, such that the total amount of collagen increases over time. The chemokines, such as MCP-1, also play a role in fibrosis by recruiting macrophages and myofibroblasts to the site of injury. Collagen turnover and ECM remodeling is regulated by various matrix metalloproteases (MMPs).

Methods of Protecting or Treating a Subject from Tissue Injury or Organ Failure

The discovery that the aromatic-cationic peptides of the present invention are useful in preventing or treating ARI is also applicable to tissue injury and organ failure in other systems besides the kidney. For instance, the aromatic-cationic peptides of the invention are predicted to minimize mitochondrial dysfunction, cell death, inflammation, and fibrosis. In some embodiments, the present invention provides a method of treating a subject having a tissue injury, e.g., noninfectious pathological conditions such as pancreatitis, ischemia, multiple trauma, hemorrhagic shock, and immune-mediated organ injury.

The tissue injury can be associated with, for example, aortic aneurysm repair, multiple trauma, peripheral vascular disease, renal vascular disease, myocardial infarction, stroke, sepsis, and multi-organ failure. In one aspect, the invention relates to a method of treating a subject having a tissue such as from heart, brain, vasculature, gut, liver, kidney and eye that is subject to an injury and/or ischemic event. The method includes administering to the subject a therapeutically effective amount of an aromatic-cationic peptide to provide a therapeutic or prophylactic effect. Another embodiment of the present invention provides the administration of the peptides of the present invention to improve a function of one or more organs selected from the group consisting of: renal, lung, heart, liver, brain, pancreas, and the like. In a particular embodiment, the improvement in lung function is selected from the group consisting of lowered levels of edema, improved histological injury score, and lowered levels of inflammation.

In some embodiments, the peptides are useful for the prevention and/or treatment of acute hepatic injury caused by ischemia, drugs (acetaminophen, alcohol), viruses, obesity (non-alcoholic steatohepatitis), and obstruction (bile duct obstruction, tumors). In some embodiments, the aromatic-cationic peptides of the invention are administered to a subject to prevent or treat acute liver failure (ALF). ALF is a clinical condition that results from severe and extensive damage of liver cells leading to failure of the liver to function normally. ALF results from massive necrosis of liver cells leading to hepatic encephalopathy and severe impairment of hepatic function. It is caused by various kinds of diseases, such as viral hepatitis (A, B, C), drug toxicity, frequent alcohol intoxication, and autoimmune hepatitis. ALF is a very severe clinical condition with high mortality rate. Drug-related hepatotoxicity is the leading cause of ALF in the United States.

In some embodiments, the aromatic-cationic peptides of the invention are administered to a subject prior to or simultaneously with the administration of an drug or agent known or suspected to induced hepatotoxicity, e.g., acetaminophen, in order to provide protection against ALF. For example, the subject may receive the peptides from about 1 to 2 hours, about 1 to 6 hours, about 1 to 12 hours, about 1 to 24 hours, or about 1 to 48 hours prior to receiving the drug or agent. Likewise, the subject may be administered the peptides at about the same time as the drug or agent to provide a prophylactic effect against ALF caused by the drug or agent. Moreover, administration of the peptides to the subject may continue following administration of the drug or agent. In some embodiments, the subject may continue to receive the peptide at intervals of about 1, 2, 3, 4, 5, 6, 7, 8, 12, 24, and 48 hours following administration of the drug or agent, in order to provide a protective or prophylactic effect.

In some embodiments, the aromatic-cationic peptides of the invention are administered to a subject exhibiting one or more signs or symptoms of ALF, including, but not limited to, elevated levels of hepatic enzymes (transaminases, alkaline phosphatase), elevated serum bilirubin, elevated serum ammonia, elevated serum glucose, elevated serum lactate, or elevated serum creatinine Administration of the peptides of the invention improves one or more of these indicators of liver function in the subject compared to a control subject not administered the peptides. The subject may receive the peptides from about 1 to 2 hours, about 1 to 6 hours, about 1 to 12 hours, about 1 to 24 hours, about 1 to 48 hours, or about 1 to 72 hours after the first signs or symptoms of ALF.

Modes of Administration

The peptides useful in the methods of the present invention are administered to a subject in an amount effective in protecting a subject's from acute renal injury or acute liver failure in a subject in need thereof. Also, the peptides useful in the methods of the present invention are administered to a subject in an amount effective in treating acute renal injury or acute liver failure in a subject in need thereof.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with ARI or ALF. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the methods of the present invention, the aromatic-cationic peptides may be administered to a subject having one or more signs of ARI caused by a disease or condition. Administration of an effective amount of the aromatic-cationic peptides may improve at least one sign or symptom of ARI in the subject, e.g., metabolic acidosis (acidification of the blood), hyperkalaemia (elevated potassium levels), oliguria or anuria (decrease or cessation of urine production), changes in body fluid balance, and effects on other organ systems. For example, a "therapeutically effective amount" of the aromatic-cationic peptides is meant levels in which the physiological effects of acute renal failure are, at a minimum, ameliorated. Typically, the efficacy of the biological effect is measured in comparison to a subject or class of subjects not administered the peptides.

The effective amount is determined during pre-clinical trials and clinical trials by methods familiar to physicians and clinicians. An effective amount of a peptide useful in the methods of the present invention, preferably in a pharmaceutical composition, may be administered to a subject in need thereof by any of a number of well-known methods for administering pharmaceutical compounds.

In a preferred embodiment, the peptide may be administered systemically or locally. In one embodiment, the peptide is administered intravenously. For example, the aromatic-cationic peptides useful in the methods of the present invention may be administered via rapid intravenous bolus injection. Preferably, however, the peptide is administered as a constant rate intravenous infusion.

The peptide may also be administered orally, topically, intranasally, intramuscularly, intraperitoneally, subcutaneously, or transdermally.

The peptides useful in the methods of the invention may also be administered to subjects by sustained release, as is known in the art. Sustained release administration is a method of drug delivery to achieve a certain level of the drug over a particular period of time. The level typically is measured by serum or plasma concentration. A description of methods for delivering a compound by controlled release can be found in PCT Application No. WO 02/083106.

Any formulation known in the art of pharmacy is suitable for administration of the aromatic-cationic peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, oral, interperitoneal, topical, intranasal, subcutaneous, or transdermal administration, formulations of the aromatic-cationic peptides useful in the methods of the present inventions may utilize conventional diluents, carriers, or excipients etc., such as are known in the art can be employed to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. The salt or buffering agent may be present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

EXAMPLES

Example 1

Protection Against Prerenal ARI Caused by Ischemia-Reperfusion (I/R)

The effects of the aromatic-cationic peptides of the invention in protecting a subject from ARI caused by ischemia-reperfusion were investigated in an animal model of ARI caused by I/R.

Sprague Dawley rats (250–300g) were assigned to four groups: (1) sham surgery group without PR; (2) I/R+saline vehicle treatment; (3) I/R+SS-20 treatment; (4) PR+SS-31 treatment. Each experimental group consisted of 8 rats. SS-20 and SS-31 (3 mg/kg, dissolved in saline) were administered to rats 30 min before ischemia and immediately before onset of reperfusion. The control rats were given saline alone on the same schedule.

Rats were anesthetized with a mixture of ketamine (90 mg/kg, i.p.) and xylazine (4 mg/kg, i.p.). The left renal vascular pedicle was occluded temporarily using a micro-clamp for 30 or 45 min. At the end of the ischemic period, reperfusion was established by removing of the clamp. At that time, the contralateral right kidney was removed. After 24 h reperfusion, animals were sacrificed and blood samples were obtained by cardiac puncture. Renal function was determined by blood urea nitrogen (BUN) and serum creatinine (BioAssay Systems DIUR-500 and DICT-500).

Renal Morphologic Examination: Kidneys were fixed in 10% neutral-buffered formalin and embedded in paraffin wax. Three micron sections were stained with hematoxylin-eosin (H&E) and periodic acid-Schiff (PAS) and analyzed by light microscopy.

Lesions were scored using the following criteria: [1] mitosis and necrosis of individual cells; [2] necrosis of all cells in adjacent proximal convoluted tubules with survival of surrounding tubules; [3] necrosis confined to the distal third of the proximal convoluted tubule with a band of necrosis extending across the inner cortex; and [4] necrosis affecting all three segments of the proximal convoluted tubule.

TUNEL Assay for Apoptosis: Renal tissue sections were deparaffinized and rehydrated by xylenes, graded alcohol series and deionized $H_2O$, and then incubated in 20 µg/ml proteinase K for 20 min at RT. In situ cell death detection POD kit (Roche, Ind., USA) was used according to the manufacturer's instructions. Briefly, endogenous peroxidase activity in the kidney sections was blocked by incubation for 10 min with 0.3% $H_2O_2$ in methanol. The sections were then incubated in a humidified chamber in the dark for 30 min at 37° C. with TUNEL reaction mixture. After washing, the slides were incubated with 50-100 µl Converter-POD in a humidified chamber for 30 min at RT. The slides were incubated in DAB solution (1-3 min), and counterstained with hemotoxylin, dehydrated through a graded series of alcohol, and mounted in Permount for microscopy.

Immunohistochemistry: Renal sections were cut from paraffin blocks and mounted on slides. After removal of paraffin with xylene, the slides were rehydrated using graded alcohol series and deionized $H_2O$. Antigen Retrieval was heated in citrate buffer (10 mM Citric Acid, 0.05% Tween 20, pH 6.0). Endogenous peroxidase was blocked with hydrogen peroxide 0.3% in methanol. Immunohistochemistry was then performed using primary antibody against heme oxygenase-1 (HO-1) (rat anti-HO-1/HMOX1/HSP32 monoclonal antibody (R&D Systems, Minn., USA) at 1:200 dilution)) and secondary antibody (HRP-conjugated goat anti-rat IgG, VECTASTAIN ABC (VECTOR Lab Inc. Mich., USA)). Substrate reagent 3-amino-9-ethylcarbazole (AEC, Sigma, MO, USA) was used to develop red color. Hematoxylin was used for counterstaining Western Blotting: Kidney tissue was homogenized in 2 ml of RIPA lysis buffer (Santa Cruz, Calif., USA) on ice and centrifuged at 500×g for 30 min to remove cell debris. Aliquots of the supernatants were stored at −80° C. Thirty (30) µg of protein of each sample was suspended in loading buffer and boiled for 5 min then each sample was subjected to a 10% SDS-PAGE gel electrophoresis. The resolved proteins were transferred to a PVDF membrane. After blocking the membrane in 5% non-fat dry milk and 1% bovine serum albumin for 1 h, the nitrocellulose blot was incubated with a 1:2000 diluted anti-HO-1/HMOX1/HSP32 or a 1:1000 diluted anti-AMPKα-1, monoclonal antibodies (R&D Systems, Minn., USA) then incubated with horseradish peroxidase-conjugated secondary antibodies. The protein bands in the blot were detected with the use of an Enhanced Chemi Luminescence detection system (Cell Signaling, Mass., USA) and X-ray film. Relative density measurements provide quantification.

ATP Content Assay: The kidney tissue was immediately put into 10 ml 5% trichloroacetic acid with 10 mM DTT, 2 mM EDTA and cut into small pieces. The tissue was homogenized on ice, incubated for another 10 min, centrifuged for 10 min at 2000×g, and neutralized with 10N KOH to pH 7.6. After centrifugation for 10 min at 2000×g, aliquots of the resulting supernatant were stored at $-80°$ C. ATP was measured by bioluminescence (ATP bioluminescent kit, Sigma, Mo., USA).

Results. The effects of the aromatic-cationic peptides of the invention on a model of ARI caused by ischemia-reperfusion were investigated. Renal mitochondria were isolated in accordance with the procedures described above and oxygen consumption was measured. The results are as follows.

TABLE 8

BUN and Serum Creatinine Values

|  | Sham | I/R + Saline | I/R + SS-20 | I/R + SS-31 |
|---|---|---|---|---|
| BUN (mg/dl) | 40.8 ± 4.6 | 170 ± 1.7* | 130.7 ± 5.5# | 113.8 ± 11.4# |
| Serum Creatinine (mg/dl) | 0.56 ± 0.04 | 1.73 ± 0.12* | 1.06 ± 0.11# | 1.05 ± 0.16# |

The above table shows treatment with either SS-20 or SS-31 improved BUN and serum creatinine values in rats after 45 min ischemia and 24 h reperfusion. BUN and serum creatinine were assayed using kits from BioAssay Systems (DIUR-500 and DICT-500). The * indicates that $p<0.05$ from the sham group. The # indicates $p<0.05$ from the IR=saline group.

FIG. 1 shows that treatment with either SS-20 or SS-31 prevented tubular cell apoptosis after 30 min ischemia and 24 h reperfusion. Renal sections were stained for apoptotic cells using TUNEL. Very few TUNEL-positive cells were observed in the medulla region of animals not subjected to I/R (FIG. 1a). A large number of TUNEL-positive epithelial cells were observed in the medulla of animals after 30 min ischemia and 24 h reperfusion (FIG. 1b). Treatment with SS-20 (3 mg/kg) or SS-31 (3 mg/kg) 30 min before onset of 30 min ischemia and just prior to reperfusion significantly prevented TUNEL-positive cells in the medulla (FIG. 1c and FIG. 1d).

Figure 2:
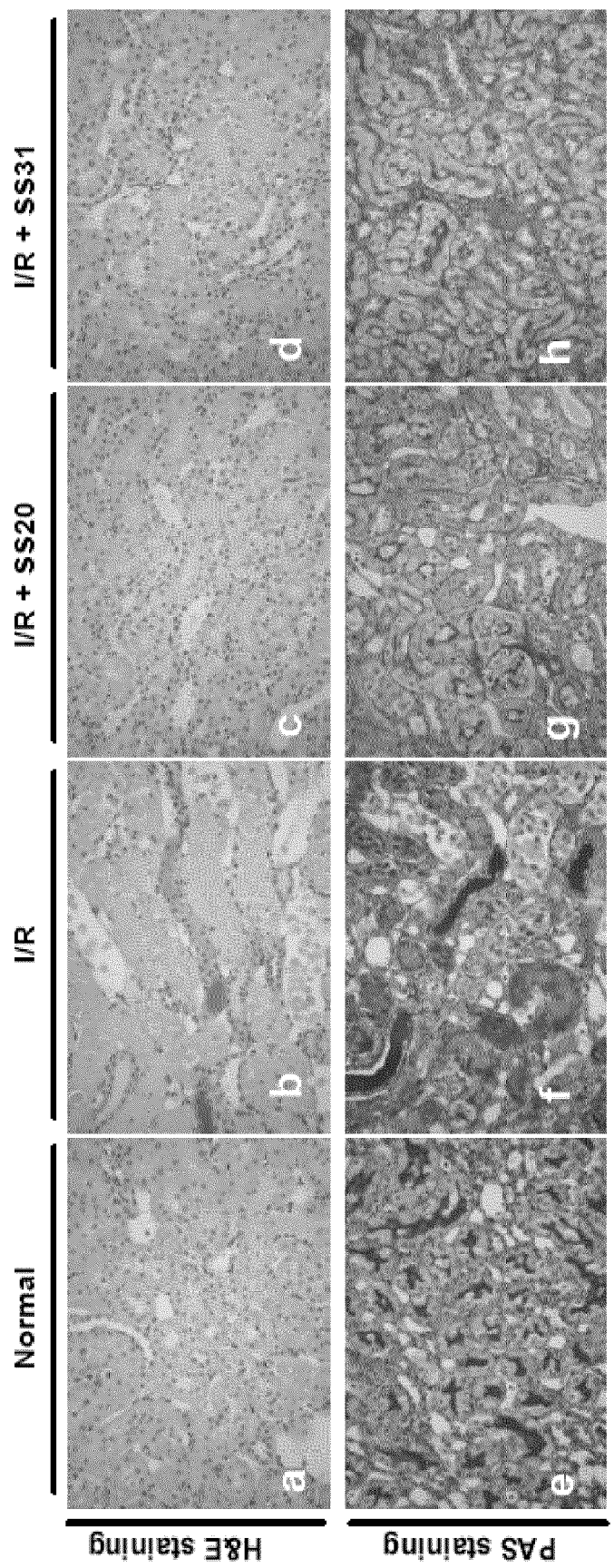
FIG. 2 shows micrographs of renal sections stained with H&E (FIG. 2a-2d) and PAS (FIG. 2e-2h).

FIG. 2 shows that treatment with either SS-20 or SS-31 prevented tubular cell injury after 45 min ischemia and 24 h reperfusion. Renal sections were stained with H&E (FIG. 2a-2d) and PAS (FIG. 2e-2h). Ischemia-reperfusion resulted in loss of brush border, vacuolization and necrosis in the proximal tubules in the inner medulla, and the distal tubules were occluded by casts (FIG. 2b). Pretreatment with either SS-20 or SS-31 protected brush border and prevented necrosis in the proximal tubules (FIG. 2c and FIG. 2d).

Figure 3:
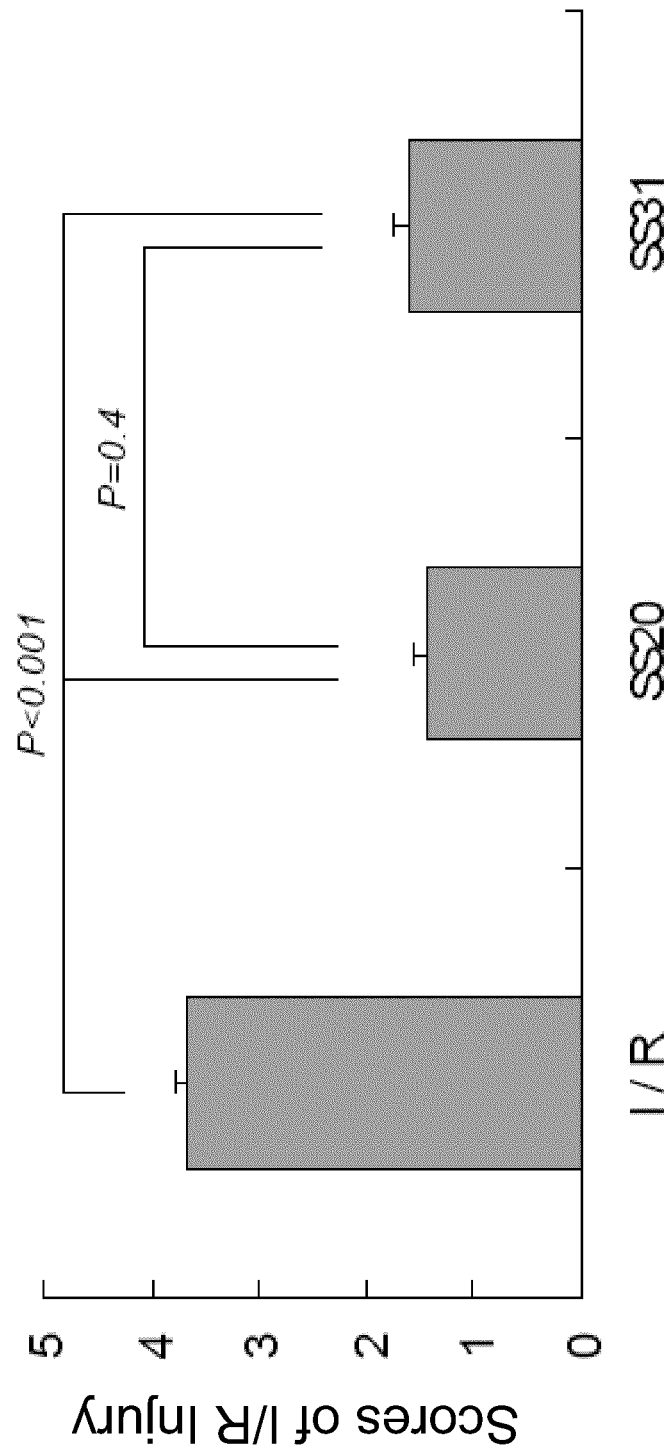
FIG. 3 is a chart showing that treatment with SS-20 or SS-31 significantly improved histopathological score resulting from 45 min ischemia and 24 h reperfusion.

FIG. 3 shows that treatment with SS-20 or SS-31 significantly improved histopathological score resulting from 45 min ischemia and 24 h reperfusion. Data are presented as the mean ±SD. A one-way ANOVA and Scheffe's tests were used for multiple pairwise comparisons.

FIG. 4 shows that treatment with SS-20 or SS-31 significantly increased rate of ATP production after reperfusion. ATP content in renal tissue was determined at the end of 15 min ischemia (FIG. 4a), and also after 1 h reperfusion following 45 min ischemia (FIG. 4b). ATP was already significantly reduced after 15 min ischemia, and this was not altered by pretreatment with either SS-20 or SS-31. ATP content was still very low after 1 h reperfusion in the vehicle control group, but was significantly higher in the animals treated with SS-20 or SS-31.

Figure 5:
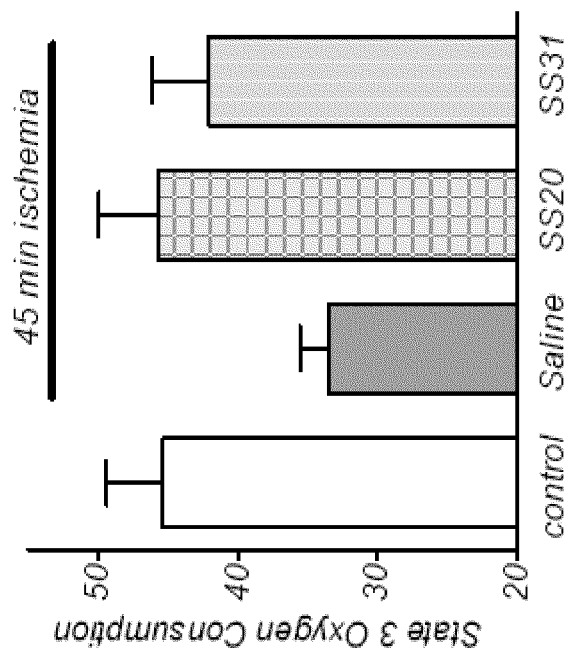
FIG. 5 is a chart showing pretreatment with SS-20 or SS-31 significantly improved renal mitochondrial respiration after 45 min ischemia.

FIG. 5 shows the results of pretreatment with SS-20 or SS-31 significantly improved renal mitochondrial respiration after 45 min ischemia. State 3 respiration was initiated with the addition of ADP. Oxygen consumption was significantly reduced in mitochondria isolated from rats after 45 min ischemia. Pretreatment with SS-20 or SS-31 significantly improved oxygen consumption such that ischemic mitochondria were no different from non-ischemic controls.

In summary, these results indicate that the peptide SS-31 and SS-20 are effective in reducing the incidence of ARI caused by ischemia-reperfusion. As such, the aromatic-cationic peptides of the invention are useful in methods of protecting a subject from ARI caused by ischemia.

Example 2

Protection Against Postrenal ARI Caused by Ureteral Obstruction

The effects of the aromatic-cationic peptides of the invention in protecting a subject from ARI caused by ureteral obstruction were investigated in an animal model of ureteral obstruction. This Example describes the results of such experiments.

Sprague-Dawley rats underwent unilateral ureteral ligation (UUO) with 4-0 silk suture through a midline abdominal incision under sterile conditions. Ureteral obstruction was carried out by ligating the left ureter at the end of lower ureter, just above the ureterovesical junction.

SS-31 (1 mg/kg or 3 mg/kg; n=8) was administered intraperitoneally, one day prior to UUO and continuing for 14 days. A separate group of animals was given saline, as a vehicle control (n=16).

Renal Histology: Trichrome sections of paraffin embedded specimens were examined by a board-certified pathologist (SVS, renal pathology specialist), and fibrosis scored on a scale of 0-+++.

Immunohistochemical Analysis: Immunohistochemical staining for macrophages was carried out using a monoclonal antibody to ED-1 (Serotec) as previously described. Macrophages were counted in 10 high-power fields (×400) by two different independent investigators in a blinded fashion. The TUNEL assay was performed as described in Example 1. The presence of fibroblasts was examined using immunohistochemistry, as described in Example 1. The antibody utilized was DAKO # S100-A4 (1:100 dilution). The S100-A4 antigen is also known as FSP-1 (fibroblast specific protein). Antigen was retrieved by incubating cells with Proteinase K for 20 min in an oven. The remaining immunoperoxidase protocol was carried out according to routine procedures. Staining for S100-A4 was found in spindle-shaped interstitial cells, and also in cells which were round, and were identified as inflammatory cells by the pathologist. Only spindle-shaped cells were included in the counts. Samples incubated without primary antibody exhibited no staining 8-OH dG staining was carried using Proteinase K for antigen retrieval. The antibody used was from the Japan Institute Control of Aging, and was used at a dilution of 1:200-1:500.

Polymerase Chain Reaction Analysis: PCR for heme oxygenase-1 (HO-1) isolated from kidneys was performed as follows. Rat kidneys were harvested and were kept at −80° C. until use. Total RNA was extracted using the Trizol ®-Chloroform extraction procedure. mRNA was purified using the Oligotex mRNA extraction kit (Qiagen, Valencia, Calif.) according to manufacturer's instructions. mRNA concentration and purity were determined by measuring absorbance at 260 nm. RT-PCR was preformed using Qiagen One-step PCR kit (Qiagen, Valencia, Calif.). PCR was performed in an automated thermal cycler ThermoHybrid, PX2 with an initial activation step for 15 min at 95° C. followed by 35 cycles of denaturation for 45 s at 94° C., annealing for 30 s at 60° C., extension for 60 s at 72° C. PCR products were separated by a 2% agarose gel electrophoresis. Bands on gels were visualized by ethidium bromide staining and analyzed using Image J densitometric analysis software. Primers for HO-1 were: CTG AAG AAG ATT GCG CAG AA (SEQ ID NO: 1) and ATG GCA TAA ATT CCC ACT GC (SEQ ID NO: 2) [427 bp]. GAPDH was used as a control.

Results. In accordance with the procedures just described, the effects of the aromatic-cationic peptides of the invention in protecting a subject from ARI caused by ureteral obstruction were investigated in an animal model of ureteral obstruction. UUO (14 days) produces a characteristic set of changes in the kidney including increased interstitial fibrosis, tubular apoptosis, macrophage infiltration and tubular proliferation. Animals were pre-treated with SS-31 one day prior to UUO and daily through 14-days. Control animals received saline only throughout the period of UUO.

Figure 6B:
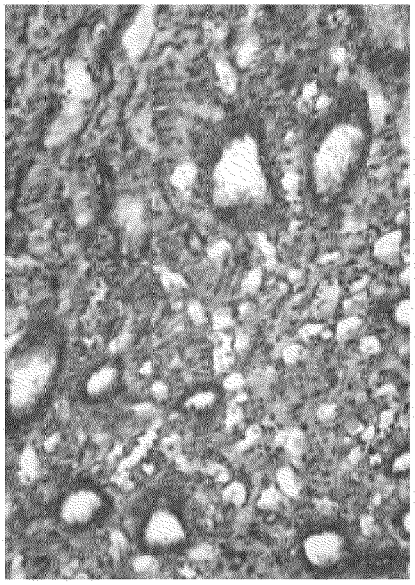
FIG. 6a-6c show inflammation or fibrosis in tubules, glomeruli, or interstitium of contralateral unobstructed kidney (CK), obstructed kidney (OK), or SS-31 treated kidneys, respectively.
Figure 6D:
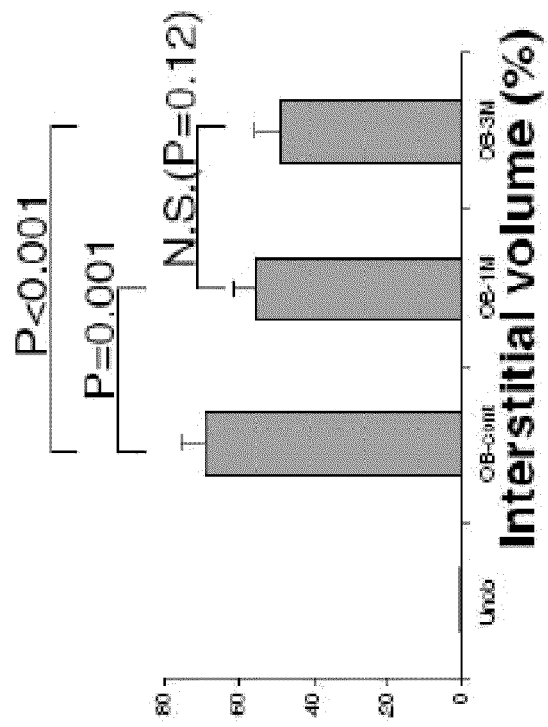
FIG. 6d is a chart showing the interstitial in the CK, OK, and SS-31 treated kidney.
Figure 6A:
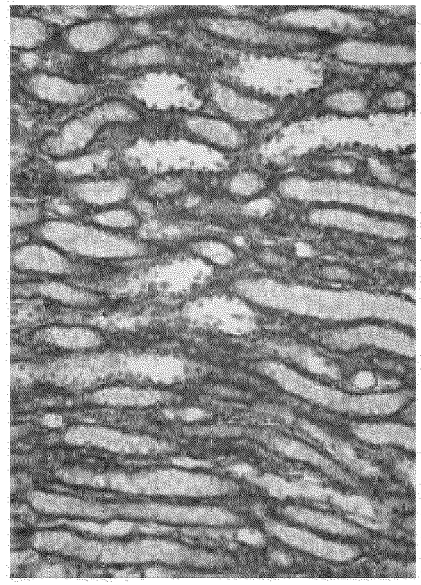
Figure 6C:
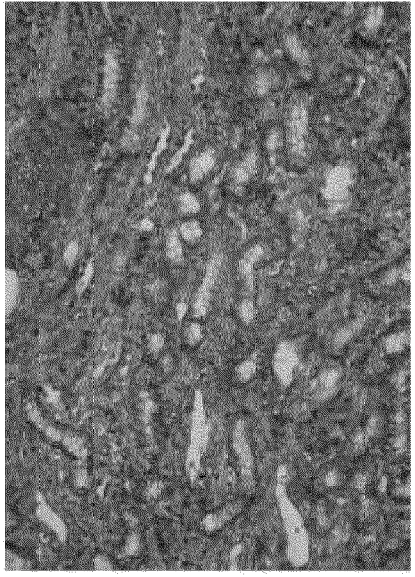

Contralateral unobstructed kidney (FIG. 6a, CK) showed very little, if any, inflammation or fibrosis in tubules, glomeruli or interstitium (data not shown). The obstructed kidney (FIG. 6b, OK) of the control vehicle treatment group showed moderate (1-2+) medullary trichrome staining, along with areas of focal peripelvic 1+ staining. The cortex showed less fibrosis than the medulla. OK also showed moderate inflammation, generally scored as 1+ in the cortex and 2+ in the medulla. SS-31 treated kidneys (FIG. 6c) showed significantly less trichrome staining, being 0-trace in the cortex and tr-1+ in the medulla). When interstitial volume was measured, medullary interstitial volume in the control OK was 69.2±2.1% as compared to 0.5±0.1% in the CK (FIG. 6d). Treatment with 1 mg/kg SS-31 modulated the increase in interstitial volume to 54.9±2.3%; a higher dose of SS-31 was also effective. Thus, SS-31 decreases medullary fibrosis in a 14-day UUO model.

Figure 7:
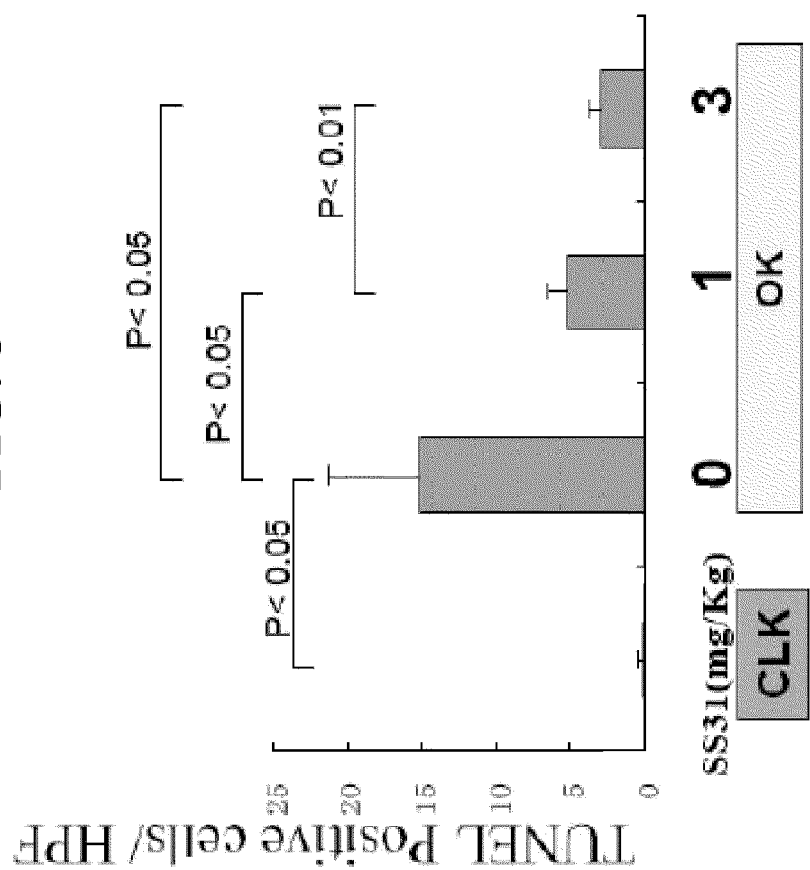
FIG. 7 is a chart showing that SS-31 decreases fibroblast expression in a 14-day UUO model.

Fibroblasts were visualized by immunoperoxidase for fibroblast-specific protein (FSP-1). Increased expression of FSP-1 was found in the OK group (16.9±2.3 cells/HPF), with only a small number of interstitial fibroblasts present in the control CK group (1.1±0.3 FSP+cells/HPF) (FIG. 7). SS-31 (1 mg/kg) significantly decreased the amount of fibroblast infiltration in the OK to 43.4% of control; SS-31 (3 mg/kg) treatment further decreased the amount of fibroblast infiltration in the OK to 28.0% of the untreated OK. Thus, SS-31 decreases fibroblast expression in a 14-day UUO model.

Figure 8:
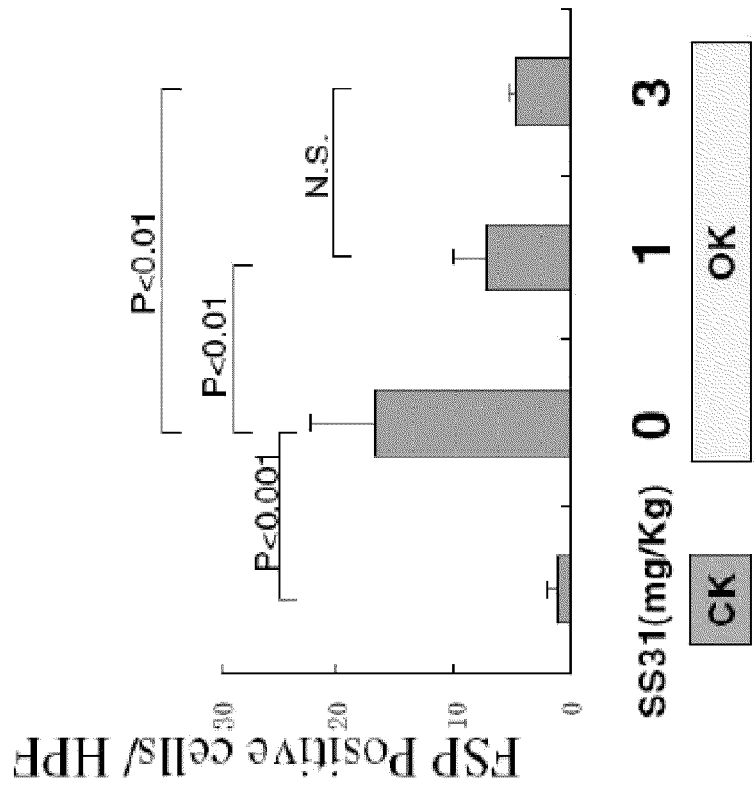
FIG. 8 is a chart showing that SS-31 decreases tubular apoptosis in a 14-day UUO model.

In the untreated OK, 2 weeks of UUO resulted in a significant increase in apoptotic tubular cells as compared to the CK. Apoptotic cells were visualized by use of the TUNEL assay. SS-31 at 1 mg/kg significantly decreased tubular apoptosis from 15.1±3.1 apoptotic cells per HPF to 5.1±0.5 cells per HPF ($p<0.05$); SS-31 at 3 mg/kg caused a further significant decrease in renal tubular apoptosis (3.0±0.3 apoptotic cells/HPF) (FIG. 8). Thus, SS-31 decreases tubular apoptosis in a 14-day UUO model.

Figure 9:
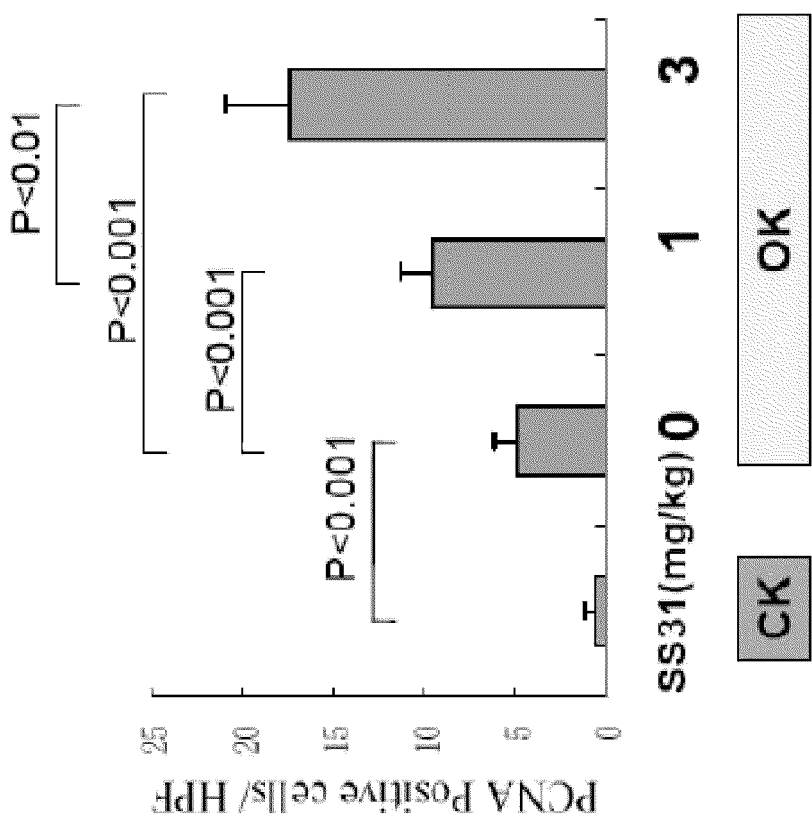
FIG. 9 is a chart showing that SS-31 decreases macrophage expression in a 14-day UUO model.

There was a significant increase in macrophage infiltration into the OK as compared to the CK after 2 weeks of UUO (33.8±6.3 cells/HPF vs. 0.04±0.03 cells/HPF). Macrophages were visualized by immunoperoxidase for ED-1. Both 1 and 3 mg/kg SS-31 significantly decreased macrophage infiltration into the OK (FIG. 9). Thus, SS-31 decreases macrophage expression in a 14-day UUO model.

Figure 10:
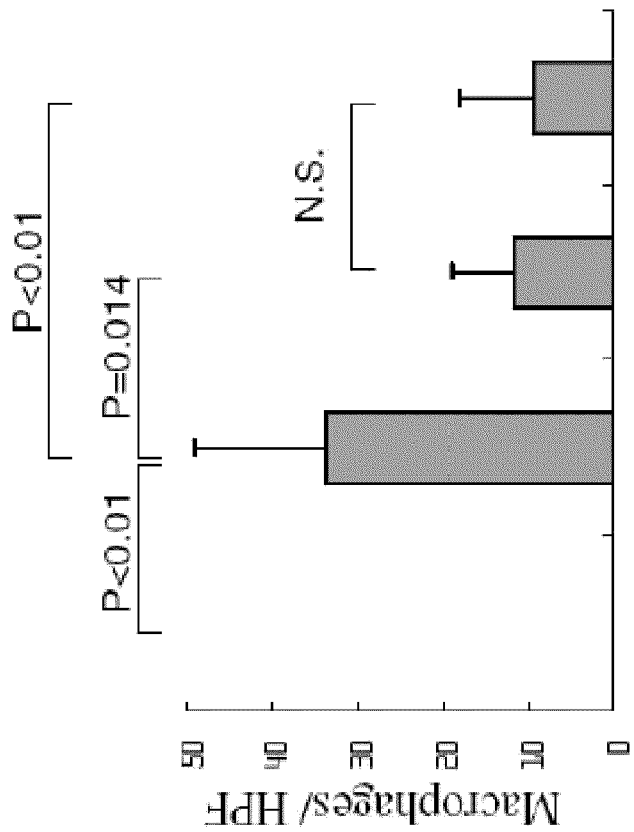
FIG. 10 is a chart showing that SS-31 increases tubular proliferation in a 14-day UUO model.

The obstructed kidney was associated with increased proliferation of renal tubular cells, as visualized by immunoperoxidase for PCNA. SS-31 caused a significant increase in renal tubular proliferation in the OK. Tubular proliferation was increased 2-fold at the 1 mg/kg dose and 3.5-fold at 3 mg/kg at the 3 mg/kg dose (FIG. 10). Thus, SS-31 increases tubular proliferation in a 14-day UUO model.

Figure 11A:
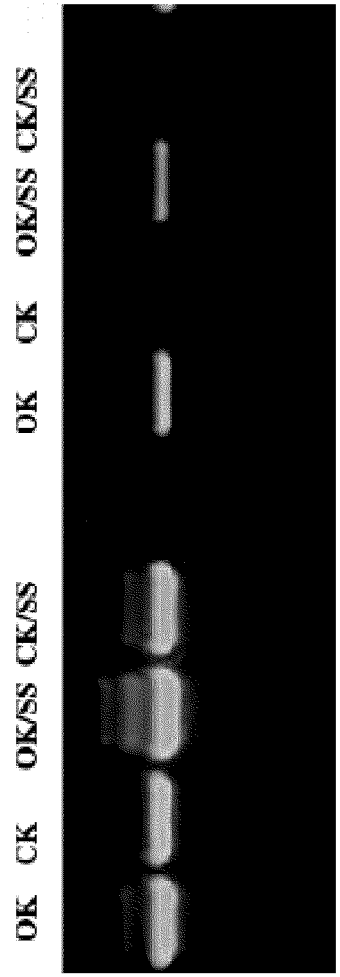
FIG. 11a is a photograph of the results of RT-PCR to analyze for HO-1 expression.
Figure 11C:
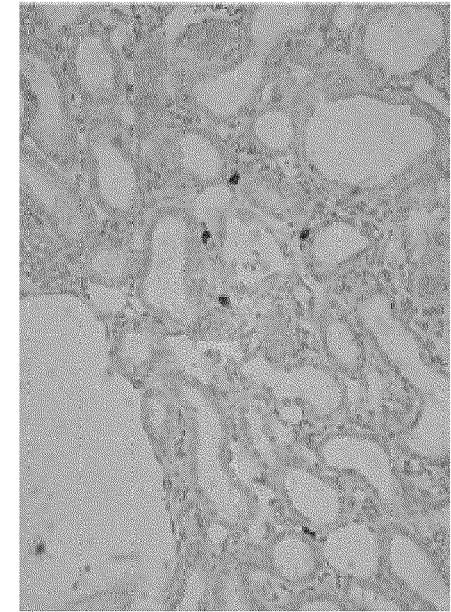
FIGS. 11b and 11c are micrographs of the results of 8-OH dG staining in both tubular and interstitial compartments of the obstructed kidney.
Figure 11B:
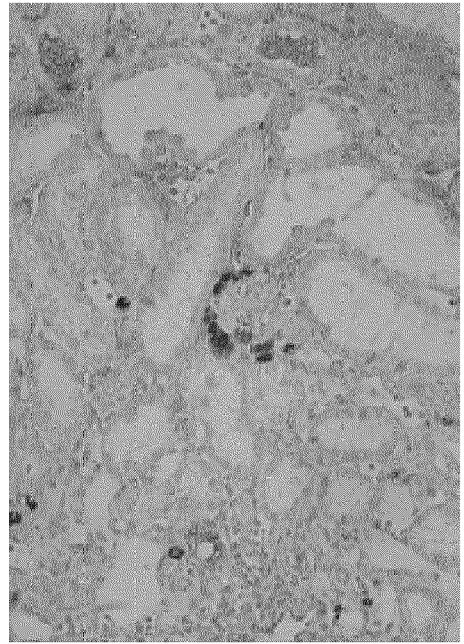

The obstructed kidney (OK) showed elevated oxidative damage, as assessed by increased expression of heme oxygenase-1 (HO-1) and 8-OH dG. RT-PCR was used for HO-1 expression UUO was associated with an increase in HO-1 expression (HO-1/GADPH 1.09 versus 0.07 in the unobstructed control) (FIG. 11a). Treatment with SS-31 decreased HO-1 expression in the obstructed kidney. 8-OH dG staining was detected in both tubular and interstitial compartments of the obstructed kidney (FIG. 11b). The number of 8-OH dG positive cells/HPF was significantly increased in the OK compared to the CK (5.0±1.4 cells/HPF vs. 1.4±0.1 cells/HPF), and this was significantly reduced with SS-31 treatment (FIG. 11c). Thus, SS-31 decreases oxidative damage in a 14-day UUO model.

In summary, these results indicate that the peptide SS-31 is effective in reducing interstitial fibrosis, tubular apoptosis, macrophage infiltration and tubular proliferation in a animal model of API caused by ureteral obstruction. As such, the aromatic-cationic peptides of the invention are useful in methods of protecting a subject from acute renal injury caused by ureteral obstruction.

Example 3

Treatment and Prevention of CIN in Indo/L-NAME Animal Models

The effects of the aromatic-cationic peptides of the invention in protecting a subject from CIN were investigated in an animal model of ARI caused by radiocontrast dye administration. This Example describes the results of such experiments.

Experiment 1

Animal Model: A model of radiocontrast dye-induced renal failure as described by Agmon et al. *J Clin Invest* 94:1069-1075 (1994) in this Example. As in humans, radiocontrast dye is generally non-toxic when administered to animals with normal renal function. However, radiocontrast dye can induce ARI in animals with impaired renal function. In this model, impaired renal function was induced by the administration of indomethacin (10 mg/kg) and L-NAME (10 mg/kg). The animals were divided into 3 groups:
 1. Group (1) control (n=8)
 2. Group (2) Indomethcin/L-NAME (given 15 min apart) followed by iothalamate (AngioConray 6 ml/kg) (n=7)
 3. Group (3) SS-31 (3 mg/kg, ip) was given 15 min prior to administration of indomethacin/L-NAME/iothalamate, and a second dose of SS-31 (3 mg/kg) was repeated immediately after drug exposure (n=9)

Experimental Protocol: Rats were kept in metabolic cages (Nalge Co., Rochester, N.Y.) with free access to tap water and standard rat chow. After a baseline 24-h urinary collection, the rats were anesthetized with a mixture of ketamine (90 mg/kg, i.p.) and xylazine (4 mg/kg, i.p.). The left femoral vein and artery were cannulated and a baseline blood sample drawn (1 ml) for measurement of creatinine level. The animals then received the various drug treatments as indicated above. Iothalamate Meglumine 60% (contrast dye; Angio-Conray 6 ml/kg) was then injected through the arterial cannula. The left femoral artery was then ligated and the cannula removed. Rats were then returned to the metabolic cages for another 24-h urine collection. At the end of this period, a blood sample was drawn from the tail vein (1 ml). After this, the animals were anesthetized, kidneys were removed, and the animals euthanized.

Renal Function: Renal function was assessed by determining GFR at baseline and 24 h following dye administration. GFR was determined by creatinine clearance which was estimated over a 24 h interval before and after dye administration. Creatinine clearance was analyzed by measuring plasma (Pcr), urinary creatinine (Ucr) levels (Bioassay Systems; DICT-500) and urine volume.

Renal Histology: Kidneys were fixed in 10% neutral-buffered formalin and embedded in paraffin wax. Three micron sections were stained with hematoxylin-eosin (H&E) and periodic acid-Schiff (PAS) and analyzed by light microscopy by a board certified pathologist.

Results: In accordance with the procedures just described, the effects of the aromatic-cationic peptides of the invention in protecting a subject from CIN were investigated in an animal model of ARI caused by radiocontrast dye administration. The results are as follows.

In the control rats, there was no significant difference in GFR between the first 24 h period (235.0±30.5 µl/min/g) and the second 24 h period (223.7±44.0 µl/min/g) (FIG. 12). When contrast dye was administered to animals pre-treated with indomethacin and L-NAME, GFR declined from 230.8±21.0 µl/min/g to 87.6±10.6 µl/min/g in 24 h. Treatment with SS-31 before and after dye administration reduced the decline in renal function, and GFR declined only from 247.9±20.4 µl/min/g to 157.9±26.6 µl/min/g. The effect of SS-31 on GFR following dye injection was significant ($P<0.05$ when compared to the vehicle treated group). Six of nine SS-31 treated rats were almost completely protected from the effects of the dye. Thus, SS-31 reduced renal dysfunction caused by radiocontrast dye.

PAS staining revealed control rat kidneys with normal morphology, demonstrated by intact brush borders on proximal tubules (FIG. 13*a*). Dye treatment resulted in a loss of the characteristic renal brush border in proximal tubule cells, as well as some vacuolization (FIG. 13*b*). These effects were attenuated with SS-31 treatment, PAS staining in these samples revealed intact brush borders and normal glomeruli (FIG. 13*c*). Thus, SS-31 protected renal tubules from radiocontrast dye injury.

The TUNEL stain was used to visualize apoptotic renal tubules. Control kidneys showed few apoptotic cells/hpf (FIG. 14*a*). Vehicle-treated, dye-injected kidneys had numerous apoptotic cells/hpf (FIG. 14*b*). This effect was greatly attenuated in SS-31-treated, dye injected kidneys (FIG. 14*c*). Thus, SS-31 prevented renal tubular apoptosis induced by radiocontrast dye injury.

In summary, these results indicate that the peptide SS-31 is effective in reducing renal dysfunction protecting renal tubules from radiocontrast dye injury. As such, the aromatic-cationic peptides of the invention are useful in methods of protecting a subject from acute renal injury caused by contrast agents.

Experiment 2

Figure 15:
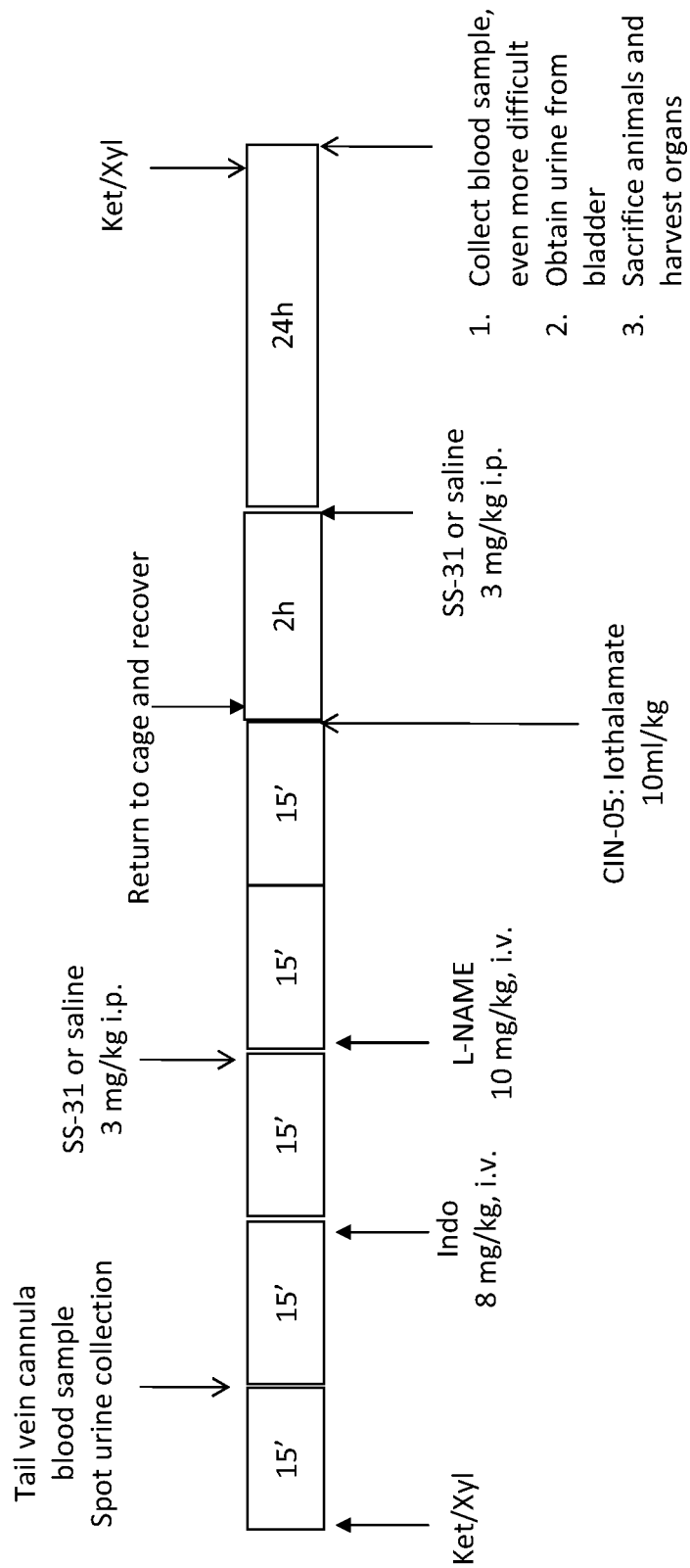
FIG. 15 is a flow chart showing the protocol and dosing schedule for the study presented in Example 3, Experiment 2.

Animal model: The same indomethacin and L-NAME model described above was used in this experiment. In this model, impaired renal function was induced by the administration of indomethacin (8 mg/kg) and L-NAME (10 mg/kg). The animals were divided into 2 groups with the dosing schedules and study protocol presented in FIG. 15.

Renal function: Renal function was assessed by determining serum and urinary creatinine using DICT-kit from Bioassays Systems (Hayward, Calif.) at baseline and 26 h following dye administration. Urinary protein concentration was also determined at baseline and 26 h following dye administration by BCA Protein Assay kit (Thermo Scientific, Rockford, Ill.). Samples were analyzed by students t-test and differences were considered significant at $p<0.05$.

Renal Histology: Kidneys were fixed in 10% neutral-buffered formalin and embedded in paraffin wax. Three micron sections were stained with hematoxylin-eosin (H&E) and periodic acid-Schiff (PAS) and analyzed by light microscopy by a board certified pathologist.

Results: In accordance with the procedures just described, the effects of the aromatic-cationic peptides of the invention in protecting a subject from CIN were investigated in an animal model of ARI caused by radiocontrast dye administration. The results are as follows.

TABLE 9

Results of Renal Function Analysis

|  | Baseline | 1 day |
|---|---|---|
| A: Indo/L-Name/Dye/PBS | | |
| No. of animals | 9 | 7 |
| Body Weight (g) | 278 ± 2.5 | 263 ± 2.2 |
| SCr (mg/dL) | 0.61 ± 0.02 | 0.85 ± 0.07 |
| Ucr (mg/dL) | 11.88 ± 3.11 | 58.97 ± 11.62 |
| U vol (ml) | N.A. | N.A. |
| U protein (mg/ml) Bradford | N.A. | N.A. |
| U protein (mg/ml) BCA | 4.32 ± 1.65 | 21.72 ± 4.63 |
| B: Indo/L-Name/Dye/SS-31 | | |
| No. of animals | 9 | 7 |
| Body Weight (g) | 278 ± 5 | 258 ± 5 |
| SCr (mg/dL) | 0.67 ± 0.09 | 0.73 ± 0.04 |
| Ucr (mg/dL) | 15.54 ± 3.87 | 38.12 ± 8.19 |
| U vol (ml) | N.A. | N.A. |
| U protein (mg/ml) Bradford | N.A. | N.A. |
| U protein (mg/ml) BCA | 4.28 ± 1.15 | 11.76 ± 2.71 |

Data presented were Mean ± SEM

For the rats pre-treated with indomethacin and L-NAME, the administration of contrast dye induced a serum creatinine increase from the baseline level 0.61±0.02 (mg/dL) to 0.85±0.07 (mg/dL); and the urinary protein concentration increased from 4.32±1.65 (mg/ml) to 21.72±4.63 (mg/ml) at 26 h. This represented a 40% Scr increase, and four-fold protein concentration increase at 26 h post contrast dye administration. In contrast, treatment with SS-31 before and after dye administration reduced the decline in renal function, and the serum creatinine increased only from the baseline level 0.67±0.09 (mg/dL) to 0.73±0.04 (mg/dL); and the urinary protein concentration increased from 4.28±1.15 (mg/ml) to 11.76±2.71 (mg/ml). This represented only a 9% Scr increase, and 1.7-fold protein concentration increase at 26 h post contrast dye administration. Five out of seven SS-31 treated rats were protected from the contrast dye induced nephropathy (i.e., a Scr increase less than 25% at 26 h post dye).

PAS staining revealed that dye treatment resulted in a loss of the characteristic renal brush border in proximal tubule cells, as well as some vacuolization (FIG. 16a). These effects were attenuated with SS-31 treatment, PAS staining in these samples revealed intact brush borders and normal glomeruli (FIG. 16b). FIG. 16c shows the control rat kidneys with normal morphology, demonstrated by intact brush borders on proximal tubules. Thus, SS-31 prevented renal tubular apoptosis induced by radiocontrast dye injury.

In summary, these results indicate that the peptide SS-31 is effective in reducing renal dysfunction protecting renal tubules from radiocontrast dye injury. As such, the aromatic-cationic peptides of the invention are useful in methods of protecting a subject from acute renal injury caused by contrast agents.

Example 4

Treatment and Prevention of CIN in Diabetic Animal Models

Experiment 1

Animal model: Impaired renal function caused by diabetes is one of the major pre-disposing factors for contrast induced nephropathy (McCullough, P et al., *J. Am. College of Cardiology*, 2008, 51, 1419-1428). In this experiment, a total of 57 SD rats were fed with high fat diet for 6 weeks, followed by the injection with low dose streptozotocin (30 mg/kg). After 9 more weeks, the blood glucose, serum creatinine and Cystatin C was measured. Based on the following selection criteria: Scr>250 μM, Cystatin C>750 ng/ml and blood glucose>=16.7 uM, 20 rats were selected to proceed with the contrast induced nephropathy study.

The animals were divided into 2 groups. Group 1 rats were fed administered iohexol and SS-31; Group 2 rats were administered iohexol and a control vehicle. On day 1, serum samples were collected from the rats in each group and total protein in urine was measured using a Bradford assay. On days 2 and 3, 3 mg/kg SS-31 (Group 1) or a vehicle (Group 2) was administered s.c. 30 min prior to the dye injection (6 mL/kg i.v. tail vein). SS-31 (Group 1) or PBS (Group 2) administration was repeated at both 2 h and 24 h post-dye administration. Serum and urine samples were collected at days 4 and 5. The rats were euthaniszed on day 5 to harvest kidneys and vital organs. Samples were analyzed by students t-test and differences were considered significant at p<0.05.

Renal function: Renal function was assessed by determining serum and urinary creatinine using Jiancheng Cr kit (Nanjing, P.R.C) at baseline, 48 h and 72 h following dye administration. The creatinine clearance was calculated based on the Scr, Ucr and Urinary volume. Urinary protein concentration was determined by Bradford Protein Assay kit (Sigma, St. Louis, Mo.). The Cystatin C was measured Westang Rat Cystatin C kit (Shanghai, P.R.C.)

Results: In accordance with the procedures just described, the effects of the aromatic-cationic peptides of the invention in attenuating the CIN in a diabetic animal model were investigated. The results are summarized in the Table 10 and FIG. 17a and FIG. 17b.

TABLE 10

Results of Renal Function Analysis

| | Baseline | T1 | T2 |
|---|---|---|---|
| Group 1: HFD/STZ/Iohexol/SS-31 | | | |
| No. of animals | | 10 | |
| Body Weight (g) | 478.5 ± 9.30 | 479.0 ± 8.5 | 474.9 ± 8.4 |
| Scr (μmol/L) | 305.7 ± 15.1 | 285.4 ± 12.0 | 295.7 ± 20.6 |
| Cystatin C (ng/ml) | 708.6 ± 51.3 | 1008.1 ± 46.4 | 1303.6 ± 147.1 |
| Ucr (μmol/L) | 3187.0 ± 196.9 | 2816 ± 163.6 | 2675.4 ± 100.8 |
| U vol (ml) | 15.4 ± 2.6 | 17.4 ± 1.6 | 20.5 ± 2.3 |
| U protein (mg/4 h) | 4.83 ± 1.03 | 4.71 ± 0.60 | 3.59 ± 1.0 |
| GFR (μl/min/100 g) | 140.0 ± 11.1 | 149.3 ± 15.6 | 162.7 ± 18.7 |
| U albumin (μg/ml) | 15.9 ± 2 | 17.6 ± 2.8 | 9.6 ± 3.3 |
| U albumin (μg/4 h) | 241.5 ± 44.6 | 291.9 ± 46 | 187.2 ± 64.1 |
| Group 2: HFD/STZ/Iohexol/PBS | | | |
| No. of animals | | 10 | |
| Body Weight (g) | 489.3 ± 11.5 | 487.6 ± 11.5 | 482.2 ± 11.5 |
| Scr (μmol/L) | 260.0 ± 12.0 | 257.2 ± 21.9 | 249.5 ± 18.8 |
| Cystatin C (ng/ml) | 655.9 ± 49.1 | 938.4 ± 57.9 | 1576.7 ± 149.9 |
| Ucr (μmol/L) | 3367.5 ± 376.0 | 3498.0 ± 691.0 | 3079.4 ± 381.3 |
| U vol (ml) | 14.37 ± 2.0 | 13.2 ± 2.3 | 16.6 ± 2.8 |
| U protein (mg/4 h) | 3.44 ± 0.75 | 3.04 ± 0.32 | 4.52 ± 1.0 |
| GFR (μl/min/100 g) | 158.5 ± 18.6 | 153.6 ± 17.3 | 177.3 ± 23.0 |
| U albumin (μg/ml) | 10.4 ± 1.4 | 22.4 ± 7.3 | 9 ± 2.2 |
| U albumin (μg/4 h) | 130.2 ± 15.6 | 184.7 ± 46.8 | 115.3 ± 17.7 |

Figure 17B:
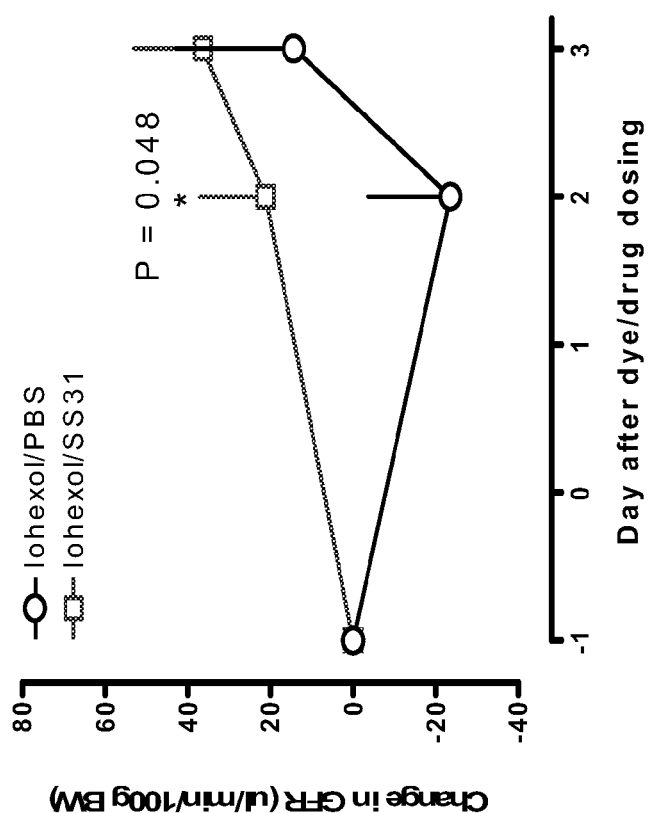
FIG. 17b is a chart showing the change in GFR in control and SS-31 treated rats following radiocontrast dye administration.
Figure 17A:
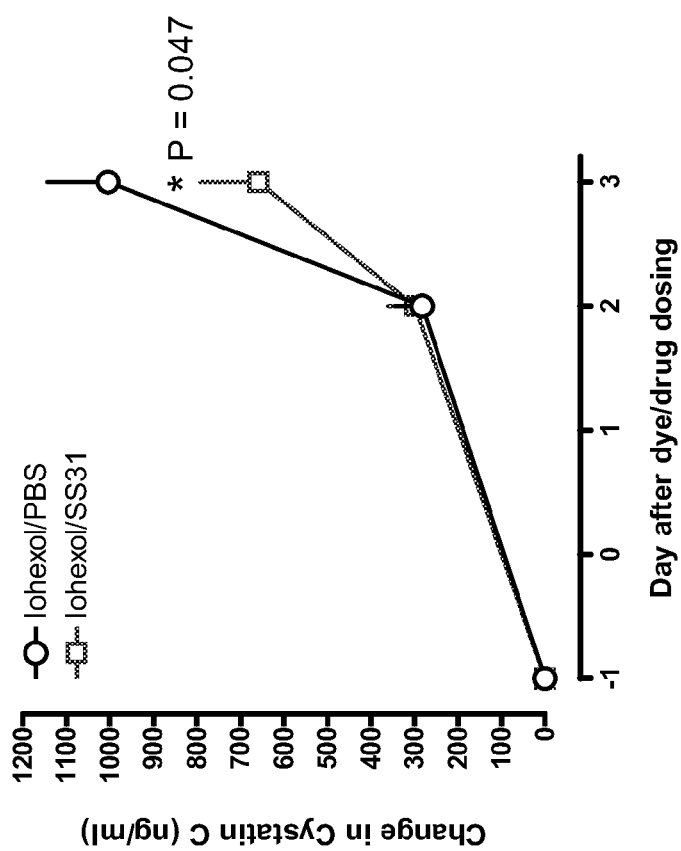
FIG. 17a is a chart showing the change in serum Cystatiin C in control and SS-31 treated rats after radiocontrast dye administration.

When contrast dye was administered in diabetic rats, for the vehicle treated group, the serum Cystatin C (an AKI biomarker) level raised from 655.9±49.1 (baseline) to 938.4±57.9 (48 h post dye) and 1576.7±149.9 (ng/ml) at 72 h post dye administration; whereas for the SS-31 treated group, the Cystatin C only raised from 708.6±51.3 to 1008.1±46.4 and 1303.6±147.1 (ng/ml) in the same period of time (FIG. 17a). At 72 hr, the effect of SS-31 in attenuating the increase of Cystatin C was statistically significant (P<0.05).

When contrast dye was administered in diabetic rats, for the vehicle treated group, the creatinine clearance decreased more than 20% at 48 h post the dye injection (FIG. 17b). In contrast, for the SS-31 treated group, there was no significant change in creatinine clearance before and after the dye injection in the same period of time. The effect of SS-31 in attenuating the creatinine clearance induced by dye administration was statistically significant (P<0.05). Thus, SS-31 reduced renal dysfunction caused by radiocontrast dye in a diabetic animal model. As such, the aromatic-cationic peptides of the invention are useful in methods of protecting a subject from acute renal injury caused by contrast agents.

Experiment 2

In this experiment, 30 SD rats were fed with high fat diet for 6 weeks, followed by the injection with low dose streptozotocin (30 mg/kg). After 9 more weeks, the rats were used in the contrast induced nephropathy study. The animals were divided into 2 groups with the doses, dosing schedules and study protocol as follows. On day 0, the weight of the animals was determined and glucose and serum samples were collected. On day 1, Scr was assayed and spot urine collection performed. On days 2 and 3, 3 mg/kg SS-31 (Group 1) or a vehicle (Group 2) was administered s.c. 30 min prior to the dye injection (6 mL/kg i.v. tail vein). SS-31 (Group 1) or PBS (Group 2) administration was repeated at 2 h, 1 day, 2, days, 3 days, 4 days, and 5 day post-dye administration. On day 8, serum and urine samples were collected and the rats were euthaniszed to harvest kidneys and vital organs.

Renal function: Renal function was assessed by determining serum and urinary creatinine using Jiancheng Cr kit (Nanjing, P.R.C) at baseline, 24 h, 3 day and 6 days following contrast dye (Iohexol) administration. The creatinine clearance was calculated based on the Scr, Ucr and Urinary volume. Samples were analyzed by students t-test and differences were considered significant at $p<0.05$.

Results: In accordance with the procedures just described, the effects of the aromatic-cationic peptides of the invention in attenuating the CIN in a diabetic animal model were investigated. The results are presented in Table 11 and in FIG. 18.

TABLE 11

Results of Renal Function Analysis

|  | Baseline | T1 | T2 | T3 |
|---|---|---|---|---|
| Group A: HFD/STZ/Iohexol/SS-31 | | | | |
| No. of animals | | | 15 | |
| Body weight (g) | 541.9 ± 23.4 | 566.5 ± 20.3 | 565.6 ± 21 | 558.3 ± 20.1 |
| Scr (μmol/L) | 214.6 ± 15.4 | 168.6 ± 21.9 | 236.2 ± 26.6 | 175.3 ± 25.9 |
| Blood Glucose (mmol/L) | 12.2 ± 2.4 | | 19.9 ± 3.4 | 15.6 ± 2.4 |
| Ucr (μmol/L) | 4182.5 ± 699.8 | 4488.9 ± 861.6 | 4744.8 ± 1350.6 | 4030.7 ± 620 |
| U vol (ml) | 18.1 ± 4.4 | 15.2 ± 4.3 | 12.8 ± 3.6 | 9.6 ± 2.3 |
| U protein (mg/4 h) | 5.4 ± 1.1 | 3.6 ± 0.8 | 4.3 ± 0.9 | 2.4 ± 0.4 |
| GFR (μl/min/100 g) | 159.2 ± 25.1 | 159.9 ± 9 | 100.9 ± 16.7 | 121.5 ± 9.1 |
| Group B: HFD/STZ/Iohexol/PBS | | | | |
| No. of animals | | | 15 | |
| Body weight (g) | 545.5 ± 21.8 | 561.8 ± 18.4 | 561.1 ± 19.3 | 554.6 ± 18.5 |
| Scr (μmol/L) | 217.4 ± 12.1 | 214.7 ± 33.6 | 253.7 ± 33 | 183.4 ± 28.8 |
| Blood Glucose (mmol/L) | 12.1 ± 2.2 | | 19.1 ± 3.1 | 16.7 ± 2.3 |
| Ucr (μmol/L) | 4584.4 ± 1270.8 | 4596.2 ± 699.2 | 4619.8 ± 693 | 3468.7 ± 521.2 |
| U vol (ml) | 20.5 ± 4.2 | 11.7 ± 3 | 8.8 ± 2 | 9.8 ± 2 |
| U protein (mg/4 h) | 6.5 ± 1.7 | 2.7 ± 0.4 | 2.8 ± 0.4 | 2.8 ± 0.6 |
| GFR (μl/min/100 g) | 172 ± 16.1 | 125.2 ± 7.3 | 83.8 ± 7.5 | 125.4 ± 15.4 |

Figure 18:
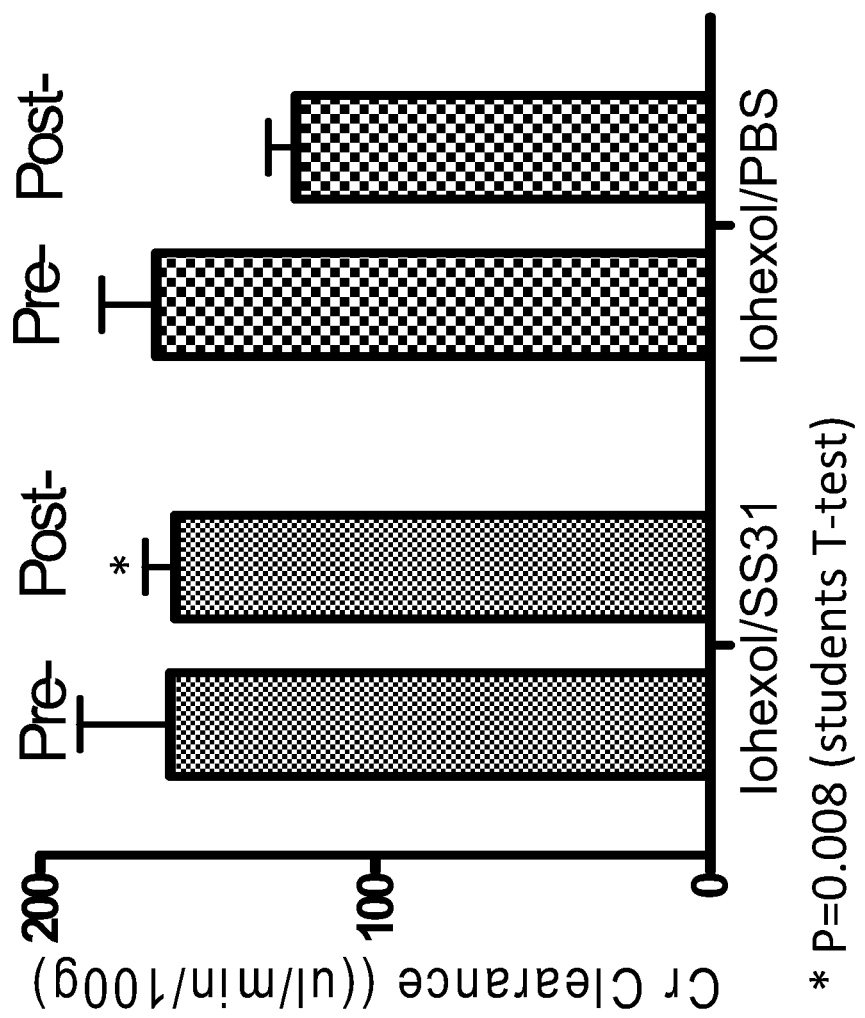
FIG. 18 is a chart showing the creatinine clearance in control and SS-31 treated rats before and after radiocontrast dye administration.

When contrast dye was administered in diabetic rats, for the vehicle treated group, the creatinine clearance decreased more than 27% at 24 h post the dye injection from 172±16.1 to 125.2±7.3 (μl/min/100 g) (FIG. 18). In contrast, for the SS-31 treated group, there was no significant change in creatinine clearance before and after the dye injection in the same period of time 159.2±25.1 to 159.9±9 (μl/min/100 g). The effect of SS-31 in attenuating the creatinine clearance induced by dye administration was statistically significant ($p<0.05$). Thus, SS-31 reduced renal dysfunction caused by radiocontrast dye in a diabetic animal model. As such, the aromatic-cationic peptides of the invention are useful in methods of protecting a subject from acute renal injury caused by contrast agents.

Experiment 3

Figure 19:
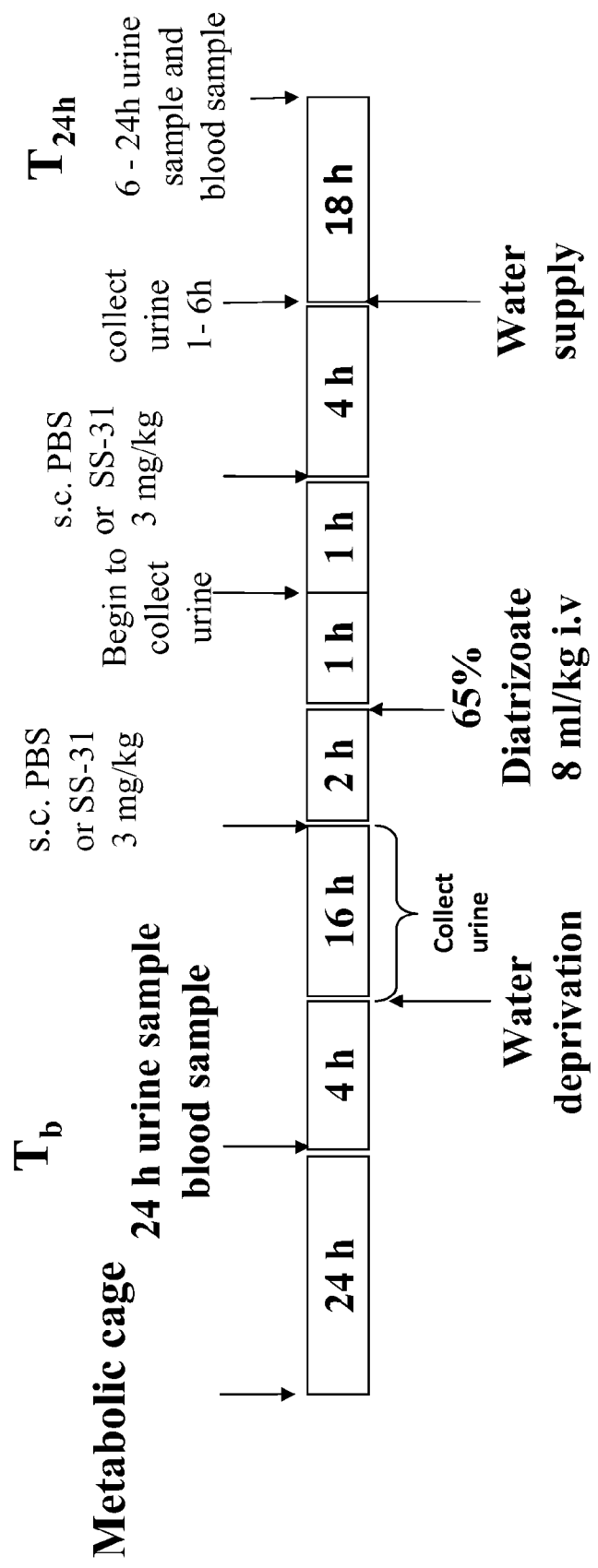
FIG. 19 is a flow chart showing the protocol and dosing schedule for the study presented in Example 4, Experiment 3.

In this experiment, 20 SD rats were fed with high fat diet for 6 weeks, followed by the injection with low dose streptozotocin (35 mg/kg). After 15 more weeks, the rats were subjected to contrast induced nephropathy study. The HFD/STZ animals were divided into 2 groups with the doses, dosing schedules and study protocol presented in FIG. 19. In addition, we included a normal control group was included in which 9 rats from the same batch on regular chow diet were subjected to the same protocol.

Renal function: Renal function was assessed by determining serum and urinary creatinine using Jiancheng Cr kit (Nanjing, P.R.C) at baseline, 24 h, 3 day and 6 days following contrast dye (Iohexol) administration. The creatinine clearance was calculated based on the Scr, Ucr and urinary volume. Samples were analyzed by students t-test and differences were considered significant at $p<0.05$.

Results: In accordance with the procedures just described, the effects of the aromatic-cationic peptides of the invention in attenuating the CIN in a diabetic animal model were investigated. The results are presented in Table 12.

TABLE 12

Serum Creatinine Results for Study Groups

| | | Scr (μM) | | |
|---|---|---|---|---|
| Group | No. | Tb | T22h | % change T22 |
| Group A: NPD/PBS/Dye/PBS | 1 | 30 | 30 | 0% |
| | 3 | 37 | 34 | -8% |
| | 4 | 38 | 34 | -11% |
| | 5 | 41 | 34 | -17% |
| | 6 | 35 | 35 | 0% |
| | 7 | 37 | 33 | -11% |
| | 8 | 35 | 38 | 9% |
| | 9 | 37 | 33 | -11% |
| Group B: HFD/STZ/PBS/Dye/PBS | 13 | 23 | 32 | 39% |
| | 20 | 21 | 27 | 29% |
| | 28 | 31 | 35 | 13% |
| | 30 | 21 | 27 | 29% |
| | 33 | 26 | 24 | -8% |
| | 36 | 28 | 32 | 14% |
| | 41 | 27 | 25 | -7% |
| | 46 | 24 | 29 | 21% |
| | 55 | 26 | 25 | -4% |
| | 63 | 22 | 27 | 23% |
| Group C: HFD/STZ/SS-31/Dye/SS-31 | 34 | 25 | 25 | 0% |
| | 38 | 25 | 26 | 4% |
| | 45 | 27 | 24 | -11% |
| | 60 | 23 | 25 | 9% |
| | 64 | 29 | 27 | -7% |
| | 65 | 24 | 28 | 17% |
| | 67 | 25 | 30 | 20% |
| | 69 | 25 | 35 | 40% |
| | 72 | 29 | 19 | -34% |

From the above table, one can see that in the control animals (group A), the Scr did not increase at 24 h post contrast dye insult in any of the animals. For HFD/STZ rats, in the vehicle treated group, 5 out 10 animals had elevated Scr more than 20% post 24 h contrast dye administration. In contrast, with the treatment of SS-31, only 2 out 9 rats had an increase in Scr more than 20% in the same period of time. Thus, SS-31 reduced renal dysfunction caused by radiocontrast dye in a diabetic animal model. As such, the aromatic-cationic peptides of the invention are useful in methods of protecting a subject from acute renal injury caused by contrast agents.

Example 5

Treatment and Prevention of CIN in a Glycerol-Induced Rhabdomyolysis Animal Model The effects of the aromatic-cationic peptides of the invention in protecting and/or treating a subject from CIN were investigated in a glycerol-induced rhabdomyolysis animal model of ARI caused by radiocontrast dye administration. This Example describes the results of such experiments.

Experiment 1

Figure 20:
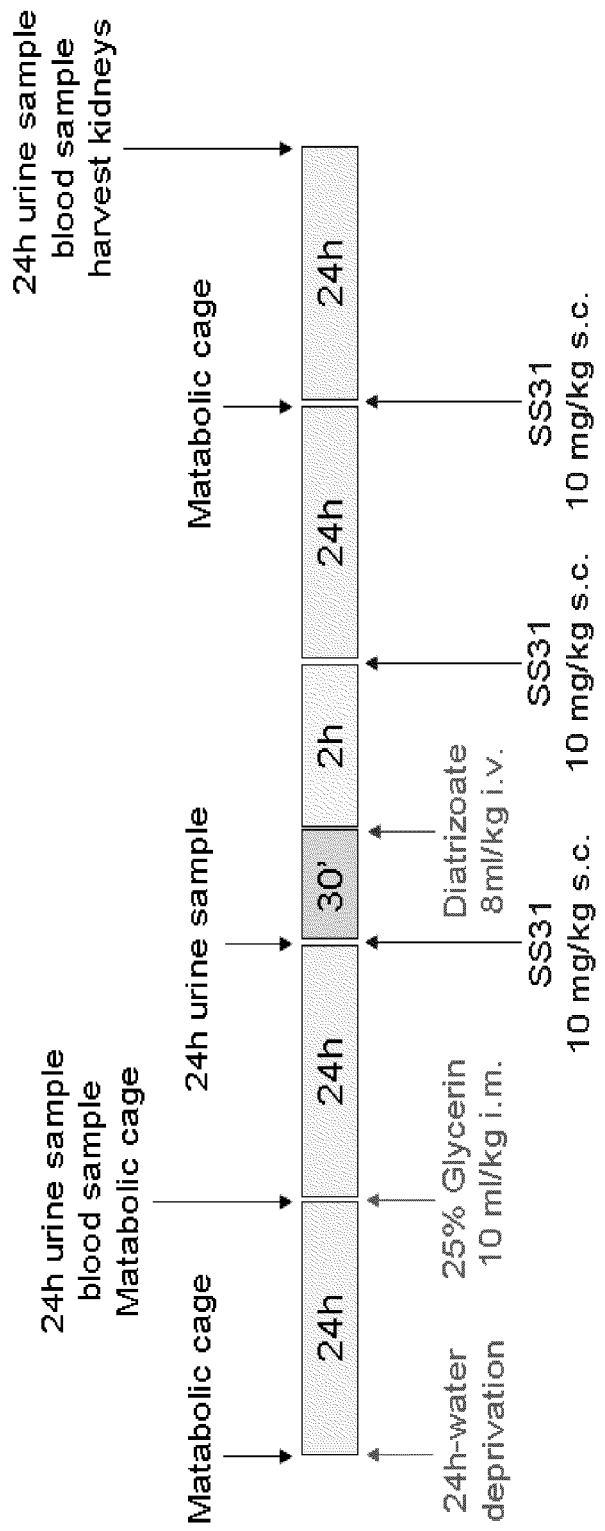
FIG. 20 is a flow chart showing the protocol and dosing schedule for the study presented in Example 5, Experiment 1.

Animal model: Previous studies indicated that the administration of contrast dye in animals with kidneys that were damaged by glycerol-induced rhabdomyolysis can cause CIN (Parvez, Z et al. *Investigative Radiology*, 1989, 24, 698-702; Duan et al. *Acta Radiologica*, 2000, 41, 503-507). In this model, SD rats with body weight of 300-400 g were dehydrated for 24 h followed by i.m. injection of 25% glycerol solution (v/v) at the dose of 10 ml/kg. Twenty-four hours (24 h) later, the rats were grouped and subjected to a contrast induced nephropathy study protocol as detailed in FIG. 20. The effects of SS-31 on ARI can be examined by comparing the renal functions in animals from group C with those from group B. Samples were analyzed by students t-test and differences were considered significant at $p<0.05$.

Renal function: Renal function was assessed by determining serum and urinary creatinine using Jiancheng Cr kit (Nanjing, P.R.C) at baseline, 24 h after dehydration and 48 h post the contrast dye administration. The creatinine clearance was calculated based on the Scr, Ucr and urinary volume. Urinary microalbumin concentration was determined by a competition ELISA assay.

Results: In accordance with the procedures just described, the effects of aromatic-cationic peptides in attenuating the CIN in a glycerol-induced rhabdomyolysis animal model were investigated. The results are presented in FIG. 21 and FIG. 22.

Figure 21A:
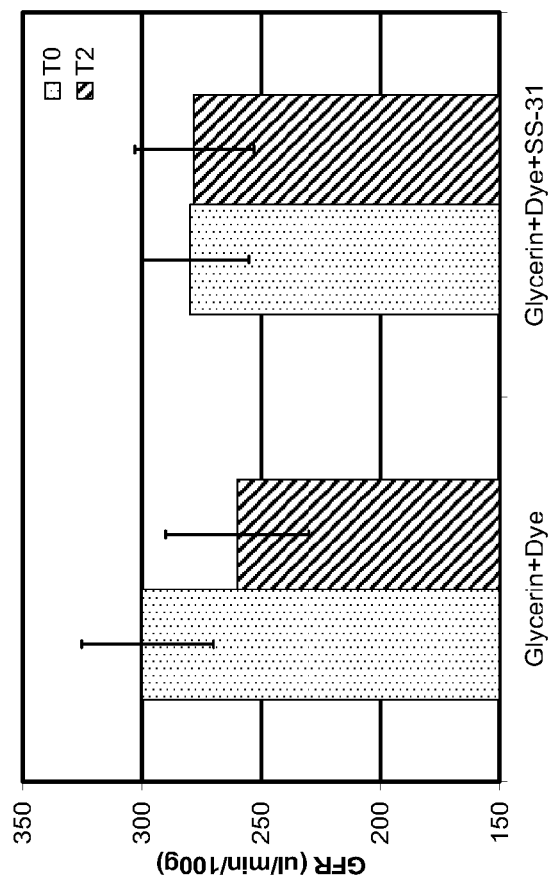
FIG. 21a is a chart showing the GFR in control and SS-31 treated rats in a glycerin model of CIN before and after radiocontrast dye administration.

When contrast dye was administered in glycerol induced rhabdomyolysis rats, the creatinine clearance decreased 13% at 48 h post the dye injection for the vehicle treated group (FIG. 21). In contrast, there was no significant change in creatinine clearance before and after the dye injection in the same period of time for the SS-31 treated group (FIG. 21a).

Figure 21B:
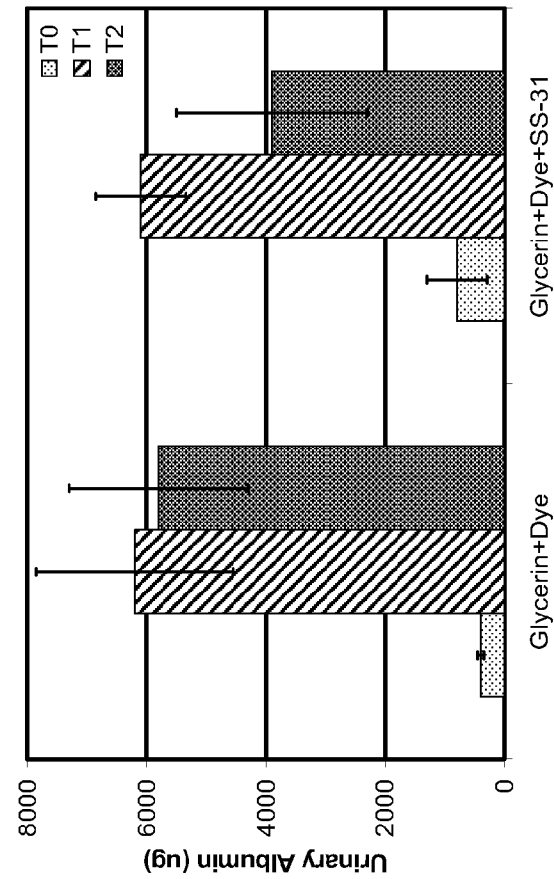
FIG. 21b is a chart showing the urinary albumin in control and SS-31 treated rats in a glycerin model of CIN before and after radiocontrast dye administration.

Albuminuria is an indicator of increased permeability of the glomerular membrane, and it can be induced by contrast dye. After 24 h dehydration (T0), the urinary microalbumin level was 385.1±59.8 (μg/24 h) for Gly/Dye/PBS group and 757.7±462.9 (μg/24 h) for Gly/Dye/SS-31 group (no peptide treatment at this time point) (FIG. 21b). With the i.m. administration of glycerol, 24 h post injection (T1), the urinary microalbumin level increased substantially in both groups to due to the glycerol-induced rhabdomyolysis. However, at T2 time point, the total albuminuria in the SS-31 treated group decreased significantly compared to the vehicle treated group, which suggests a protective effect for SS-31 on the permeability of the glomerular basement membrane caused by the contrast dye in this glycerol-induced rhabdomyolysis model.

PAS staining revealed the dye treatment resulted in a loss of the characteristic renal brush border in proximal tubule cells, swelling glomeruli and marked protein cast deposition in the renal tubule cells (FIG. 22a). These effects were attenuated with SS-31 treatment because PAS staining in these samples revealed intact brush borders, normal glomeruli and minimum protein cast in the tubular cells (FIG. 22b). Thus, SS-31 protected renal tubules from radiocontrast dye injury.

Experiment 2

Figure 23:
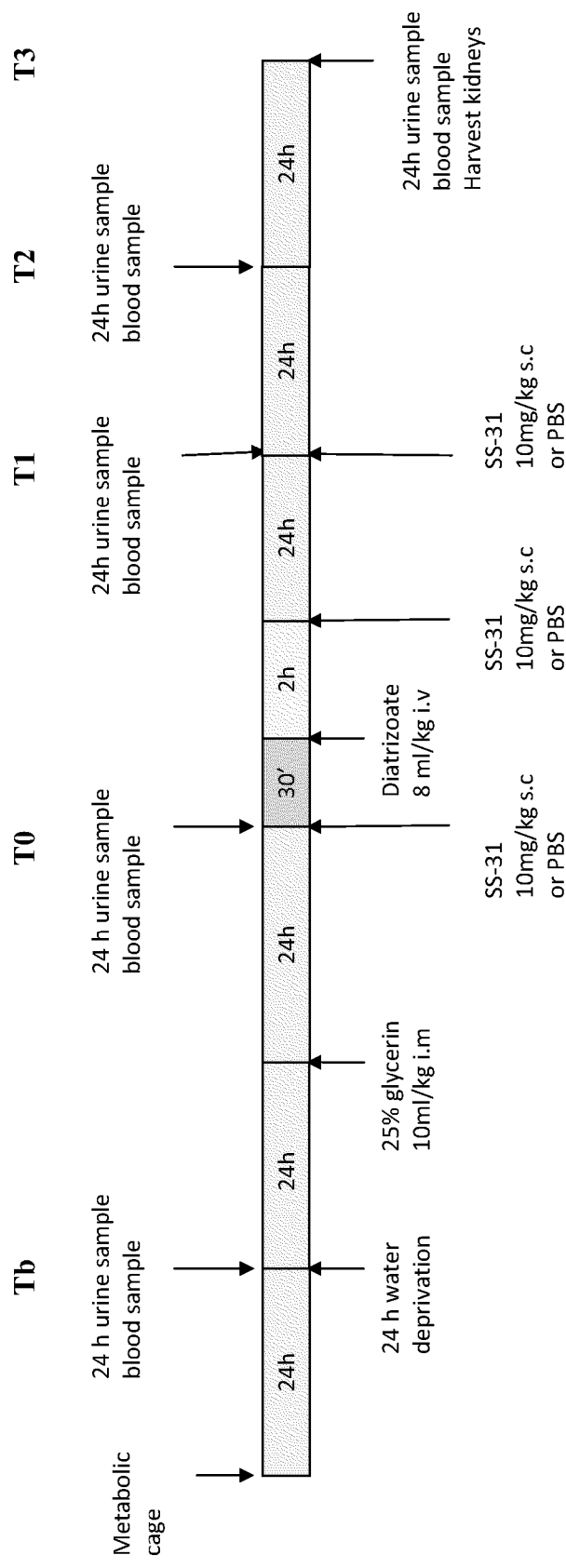
FIG. 23 is a flow chart showing the protocol and dosing schedule for the study presented in Example 5, Experiment 2.

SD rats with body weight of 300-400 grams were dehydrated for 24 h followed by i.m. injection with 25% glycerol solution (v/v) at the dose of 10 ml/kg. Twenty-four hours later, the rats were grouped and subjected to contrast induced nephropathy study protocol. Sixteen SD rats with body weight of 300-350 g were randomized into three groups with the doses, dosing schedules and study protocol presented in FIG. 23. The effects of SS-31 on ARI can be examined by comparing the renal functions in animals from group A with that from group B. Samples were analyzed by Student's t-test and differences were considered significant at $p<0.05$.

Renal function: Renal function was assessed by determining serum and urinary creatinine using Jiancheng Cr kit (Nanjing, P.R.C) at baseline, 24 h after dehydration and 48 h post the contrast dye administration. The creatinine clearance was calculated based on the Scr, Ucr and urinary volume. Urinary protein concentration was determined by Bradford Protein Assay kit (Sigma, St. Louis, Mo.).

Results: In accordance with the procedures just described, the effects of the aromatic-cationic peptides of the invention in attenuating the CIN in a glycerol-induced rhabdomyolysis animal model were investigated. The results are presented in FIGS. 24, 25, and 26.

Figure 24:
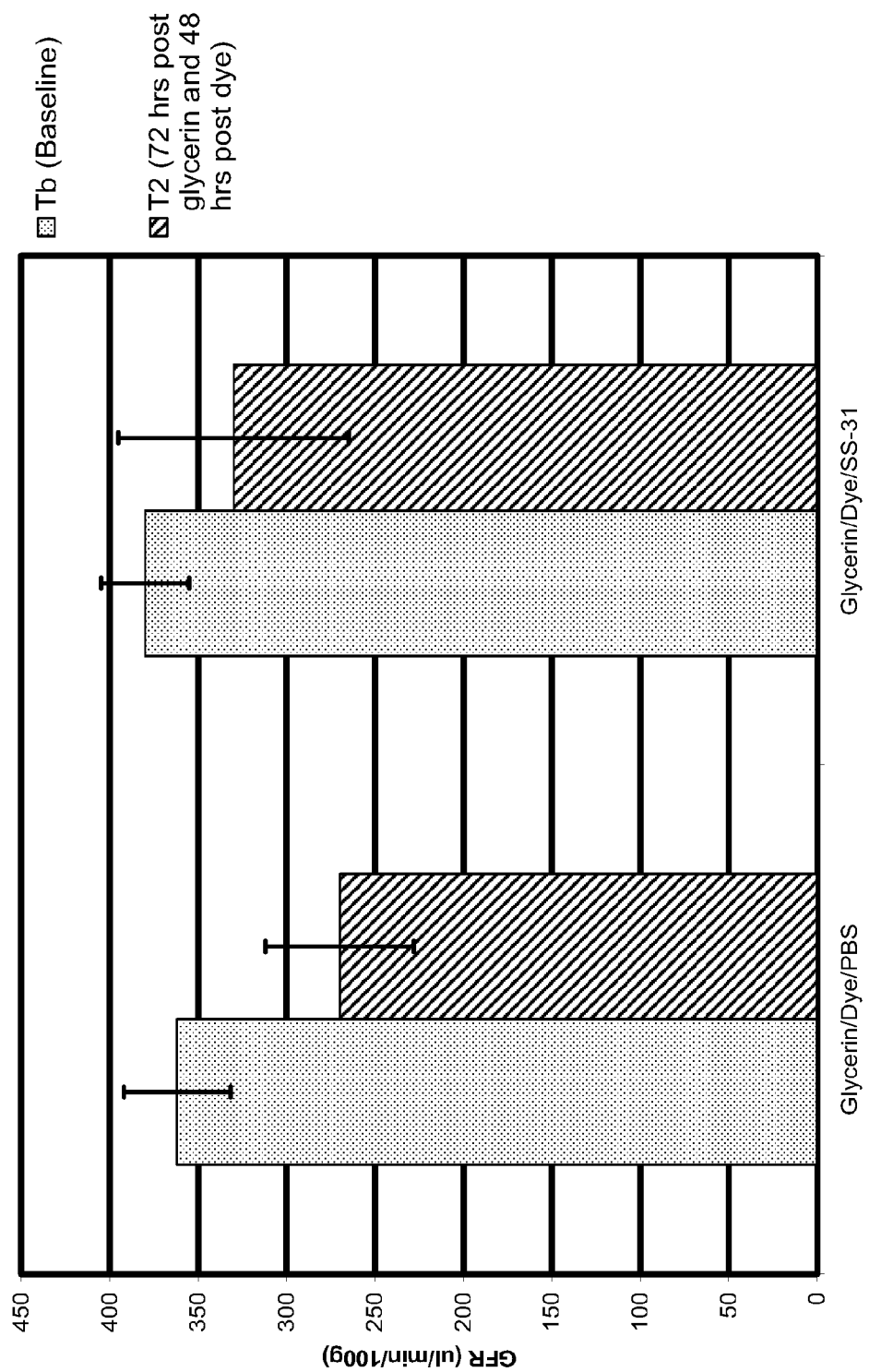
FIG. 24 is a chart showing the GFR in control and SS-31 treated rats in a glycerin model of CIN before and after radiocontrast dye administration.

When contrast dye was administered in glycerol-induced rhabdomyolysis rats, the creatinine clearance decreased 25% at 48 h post the dye injection for the vehicle treated group (FIG. 24). In contrast, the reduction of creatinine clearance was 13% in the same period of time for the SS-31 treated group. Thus, SS-31 reduced renal dysfunction caused by radiocontrast dye in a glycerol induced rhabdomyolysis animal model.

Figure 25:
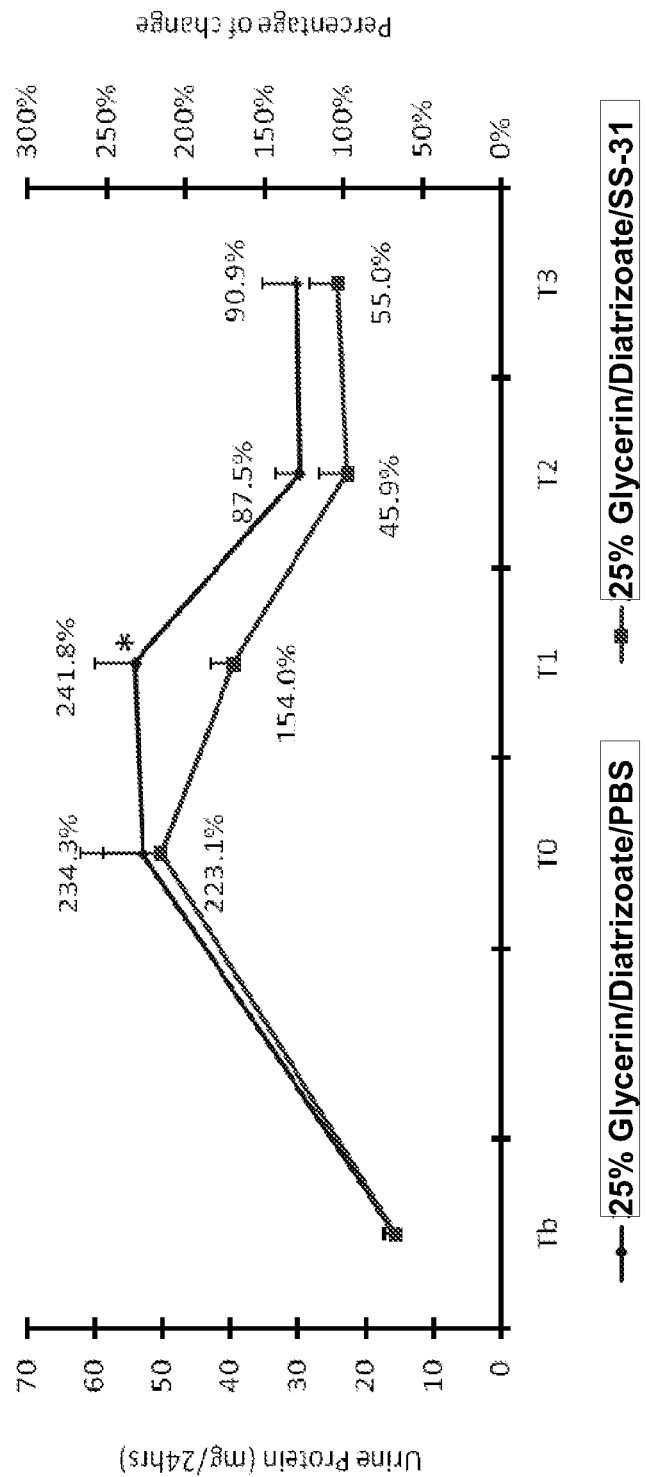
FIG. 25 is a chart showing the urine protein in control and SS-31 treated rats in a glycerin model of CIN before and after radiocontrast dye administration.

Proteinuria is a sign of renal damage, and the presence of excess protein in urine indicates either an insufficiency of absorption or impaired filtration. It was previously reported that glycerol and contrast media can increase the permeability of the glomerular membrane and cause excessive amount of urinary protein leaking (Thomsen H. S. et al., *Acta Radiologica*, 1989, 30, 217-222). In the vehicle treated group, the 24 h urinary protein level at each different time point was: Tb (baseline)=15.8±1.6 mg; T0 (24 h post glycerin)=52.9±9.1 mg; T1 (48 h post glycerin and 24 h post dye)=54.1±5.8 mg, T2 (72 h post glycerin and 48 h post dye)=29.7±3.6 mg; and T3 (96 h post glycerin and 72 h post dye)=30.2±5.1 mg (FIG. 25).

In the SS-31 treatment group, the 24 h urinary protein level at Tb (15.5±1.5 mg) and T0 (50.2±8.6 mg) was comparable to the vehicle control group, when there was no peptide administration at these time points. However, at the time point of T1 (48 h post glycerin and 24 hrs post dye), the 24 h urinary protein in the SS-31 treated group was reduced to 39.5±3.5 mg (FIG. 25). Compared to the vehicle treated group at the same time point, the difference was statistically significant (p<=0.05). This demonstrated that SS-31 peptide accelerated the recovery of the glomerular basement membrane permeability dysfunction in this CIN animal model. Thus, the aromatic-cationic peptides of the invention are useful in methods for treating ARI caused by radiocontrast dye.

Figure 26A:
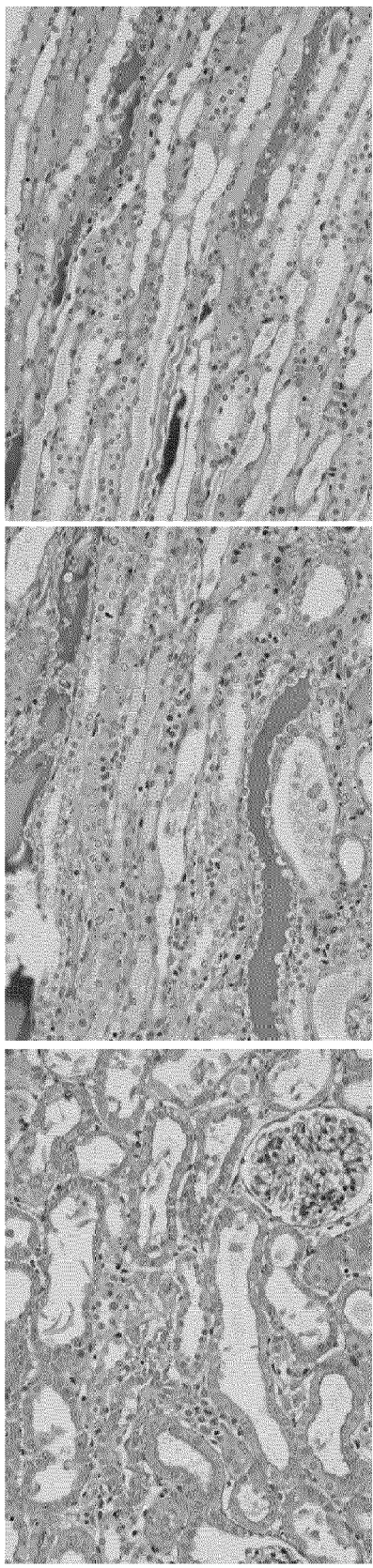
FIG. 26a shows a series of micrographs of PAS staining of renal sections from rats treated with glycerin, Diatrizoate, and a control (PBS).
Figure 26B:
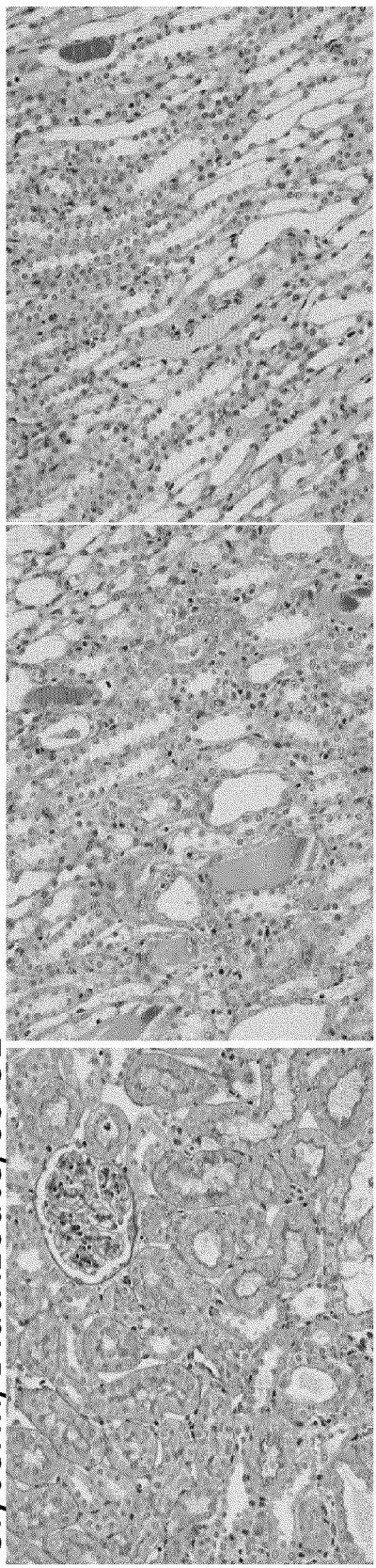
FIG. 26b shows a series of micrographs of PAS staining of renal sections from rats treated with glycerin, Diatrizoate, and SS-31.

PAS staining revealed the dye treatment resulted in a loss of the characteristic renal brush border in proximal tubule cells, swelling glomeruli and marked protein cast deposition in the renal tubule cells (FIG. 26a). These effects were attenuated with SS-31 treatment because PAS staining in these samples revealed intact brush borders, normal glomeruli and minimum protein cast in the tubular cells (FIG. 26b). Thus, SS-31 protected renal tubules from radiocontrast dye injury.

Experiment 3

Figure 27:
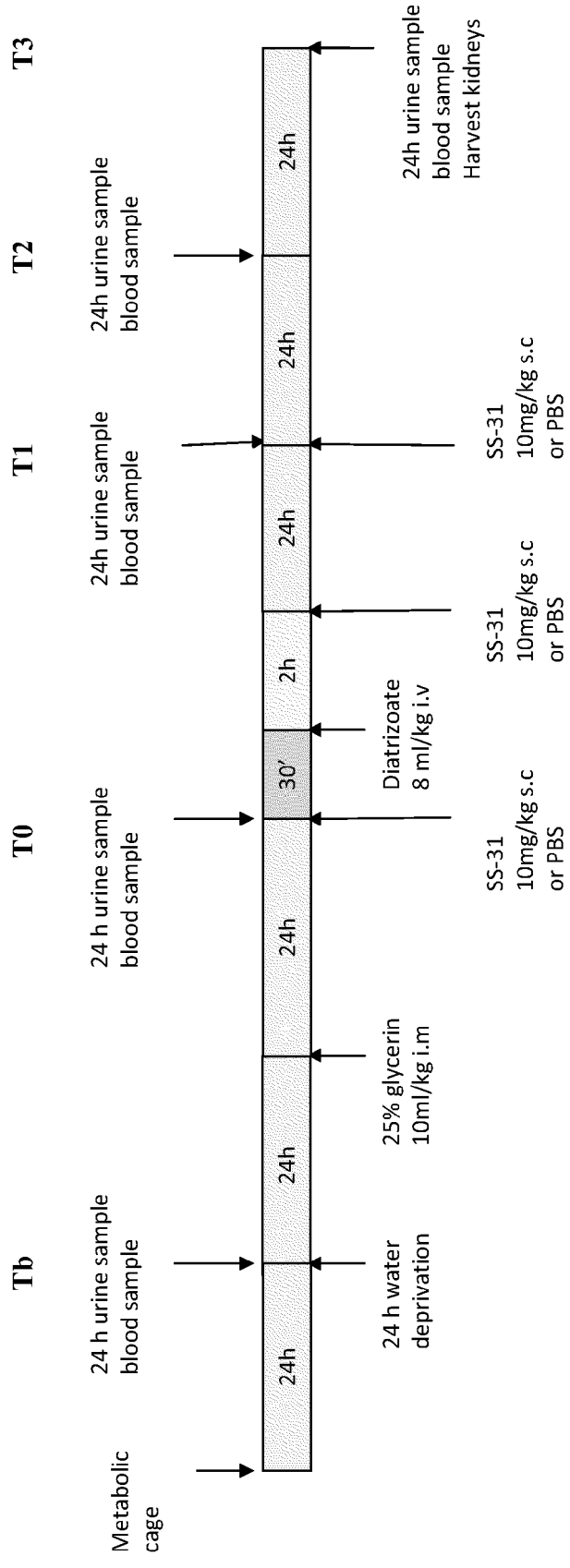
FIG. 27 is a flow chart showing the protocol and dosing schedule for the study presented in Example 5, Experiment 3.

SD rats with body weight of 300-400 grams were dehydrated for 24 h followed by i.m. injection with 25% glycerol solution (v/v) at the dose of 10 ml/kg. Twenty-four hours (24 h) later, the rats were grouped and subjected to contrast induced nephropathy study protocol. Eighteen SD rats with body weight of 350-400 g were randomized into three groups with the doses, dosing schedules and study protocol presented in FIG. 27. The effects of SS-31 on ARI can be examined by comparing the renal functions in animals from group A with that from group B.

Renal function: Renal function was assessed by determining serum and urinary creatinine using Jiancheng Cr kit (Nanjing, P.R.C) at baseline, 24 h after dehydration and 48 h post the contrast dye administration. The creatinine clearance was calculated based on the Scr, Ucr and Urinary volume. Urinary protein concentration was determined by Bradford Protein Assay kit (Sigma, U.S.A.). Samples were analyzed by students t-test and differences were considered significant at $p<0.05$.

Results: In accordance with the procedures just described, the effects of the aromatic-cationic peptides of the invention in attenuating the CIN in a glycerol-induced rhabdomyolysis animal model were investigated. The results are presented in FIG. 28 and FIG. 29.

Figure 28:
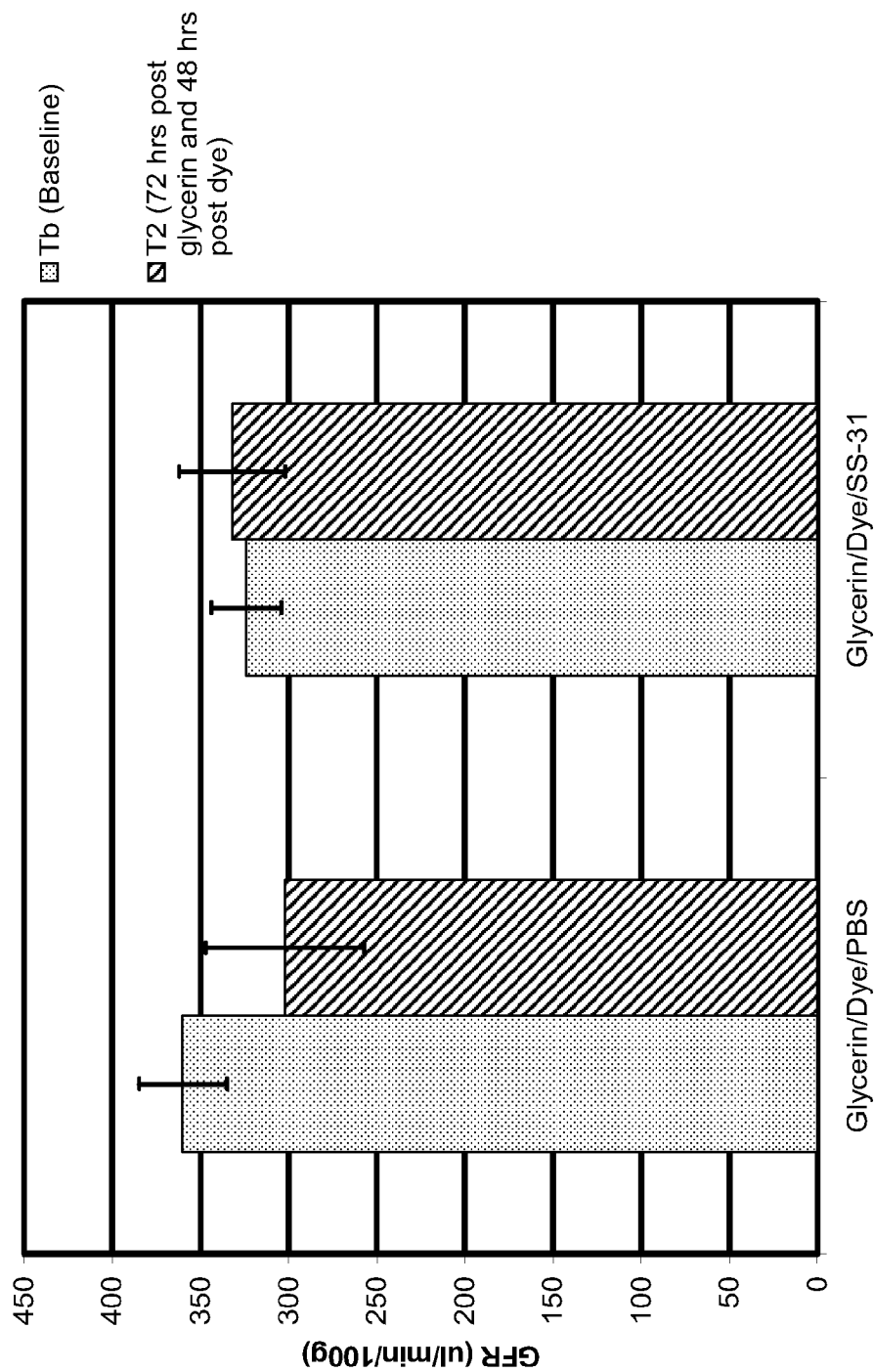
FIG. 28 is a chart showing the GFR in control and SS-31 treated rats in a glycerin model of CIN before and after radiocontrast dye administration.

When contrast dye was administered in glycerol-induced rhabdomyolysis rats, for the vehicle treated group, the creatinine clearance decreased 24% at 48 h post the dye injection (FIG. 28). In contrast, for the SS-31 treated group, there was no significant change in the creatinine clearance in the same period of time (FIG. 28). Thus, SS-31 reduced renal dysfunction caused by radiocontrast dye in a glycerol-induced rhabdomyolysis animal model.

Figure 29:
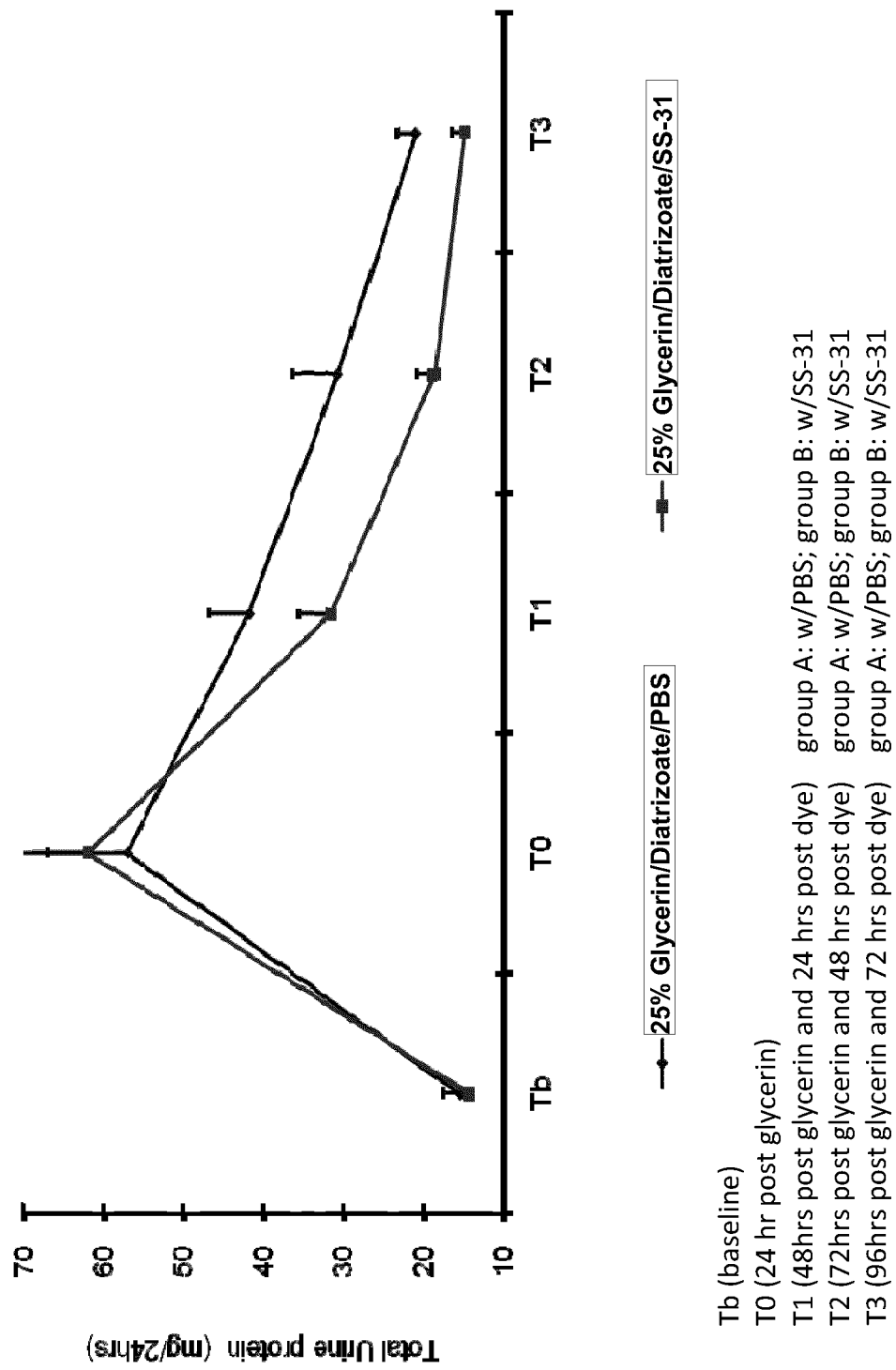
FIG. 29 is a chart showing the urine protein in control and SS-31 treated rats in a glycerin model of CIN before and after radiocontrast dye administration.

As discussed above, proteinuria is a sign of renal damage, and the presence of excess protein in urine indicates either an insufficiency of absorption or impaired filtration. Comparing the protein level at different time point in the vehicle treated group with the SS-31 treated group, the peptide treated group recovered faster than the vehicle group (FIG. 29). This demonstrated that SS-31 peptide accelerated the recovery of the glomerular basement membrane permeability dysfunction in this CIN animal model. Thus, the aromatic-cationic peptides of the invention are useful in methods for the treatment of ARI caused by radiocontrast dye.

Figure 30A:
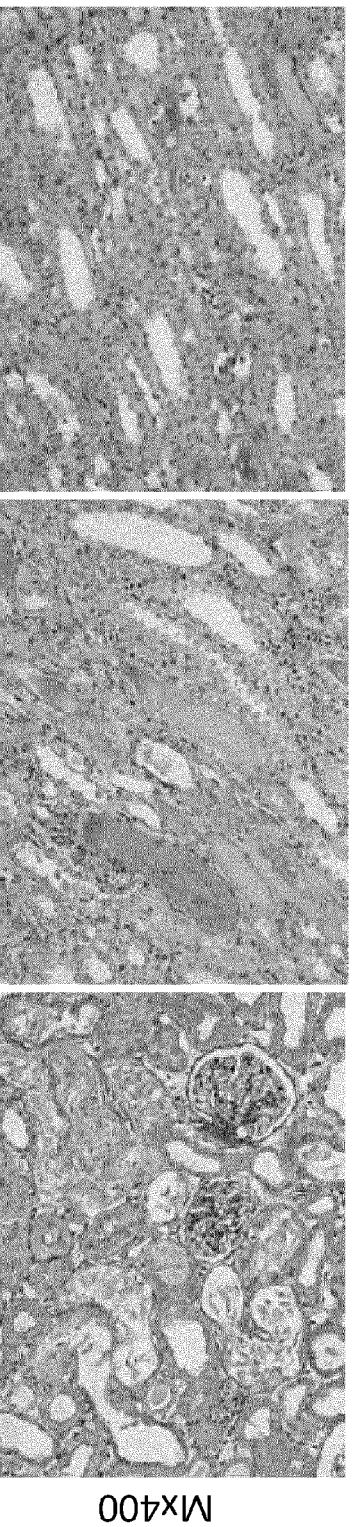
FIG. 30a shows a series of micrographs of PAS staining of renal sections from rats treated with glycerin, Diatrizoate, and a control (PBS).
Figure 30B:
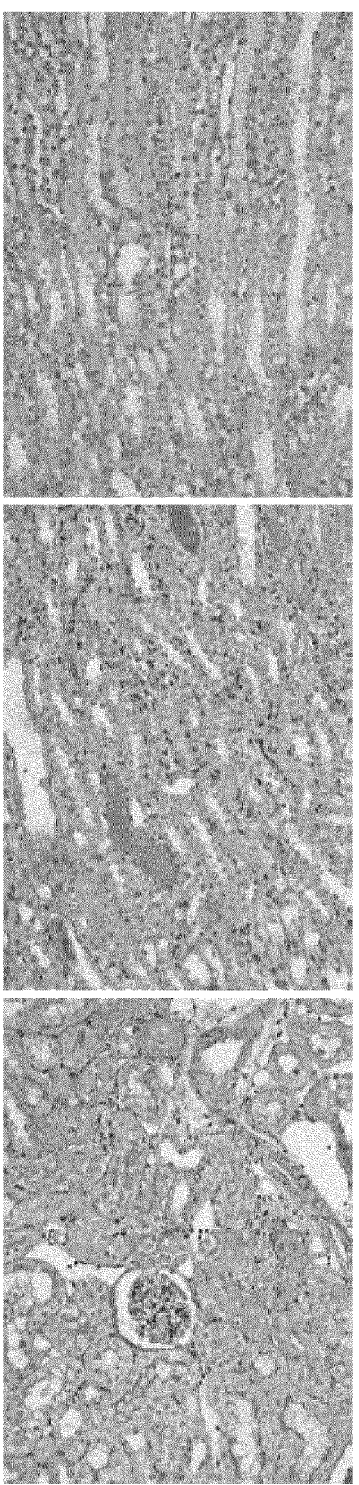
FIG. 30b shows a series of micrographs of PAS staining of renal sections from rats treated with glycerin, Diatrizoate, and SS-31.

PAS staining revealed the dye treatment resulted in a loss of the characteristic renal brush border in proximal tubule cells, swelling glomeruli and marked protein cast deposition in the renal tubule cells (FIG. 30a). These effects were attenuated with SS-31 treatment because PAS staining in these samples revealed intact brush borders, normal glomeruli and minimum protein cast in the tubular cells (FIG. 30b). Thus, SS-31 protected renal tubules from radiocontrast dye injury.

In summary, the results from the above examples clearly demonstrated the usefulness of the aromatic-cationic peptides of the invention in protecting a subject from acute kidney injury caused by contrast agents in several animal models. In addition, it accelerated the recovery of the injured kidneys evidenced in Experiment 7 and 8.

Example 6

Treatment and Prevention of Nephrotoxicity in the $CCl_4$ Chronic Kidney Injury Model Animal model: Generation of reactive radicals has been implicated in carbon tetrachloride-induced nephrotoxicity, which are involved in lipid peroxidation, accumulation of dysfunctional proteins, leading to injuries in kidneys (Ozturk, F. et al. *Urology*, 2003, 62, 353-356). This Example describes the effect of administration of aromatic-cationic peptides for the prevention of carbon tetrachloride ($CCl_4$)-induced chronic nephrotoxicity.

Study design and experimental protocol: In this model, SD rats with body weight of 250 g were fed with 0.35 g/L phenobarbital solution (Luminal water) for two weeks, then divided into three groups and treated as follows.

TABLE 13

Treatment Groups

| Group | # of rats | Inducing Agent For 7 weeks | Compound | Dose Vol. (ml/kg) | Dose (mg/kg) | Schedule | Vehicle |
|---|---|---|---|---|---|---|---|
| 1 Naïve control | 9 | Luminal water + Olive oil i.g., 1 ml/kg, twice per week | PBS only s.c. | 2 | N/A | 5 days a week, q.d., for 7 wks | PBS 2 ml/kg |
| 2 CCl4 control | 12 | Luminal water + 50% $CCl_4$ i.g., 2 ml/kg, twice per wk | PBS only s.c. | 2 | N/A | 5 days a week, q.d., for 7 wks | PBS |
| 3 SS-31 | 12 | Luminal water + 50% $CCl_4$ i.g., 2 ml/kg, twice per wk | SS-31 s.c. | 2 | 10 mg/kg | 5 days a week, q.d., for 7 wks | PBS |

At the end of fifth week, four rats from each group were sacrificed for liver histopathological sectioning and fibrosis examination. In the end of 7th week, all remaining rats in each group were sacrificed, and kidney and liver tissues were harvest for histopathological sectioning and examination.

Renal Histology: Kidneys were fixed in 10% neutral-buffered formalin and embedded in paraffin wax. Three micron sections were stained with hematoxylin-eosin (H&E) and analyzed by light microscopy by a certified pathologist.

Results: In accordance with the procedures described above, the effects of the aromatic-cationic peptides of the invention in protecting against $CCl_4$ induced chronic nephrotoxcity were investigated. The results are presented in Table 14 below:

TABLE 14

Summary of Renal Histology Results

|  | Glomeruli | Tubular epithelial cell degeneration | Tubular epithelial cell necrosis |
| --- | --- | --- | --- |
| Naïve group | 5/5 – | 5/5 – | 5/5 – |
| $CCl_4$ group | 6/6 – | 4/6 ++ | 2/6 ++ |
|  |  | 2/6 + | 1/6 + |
|  |  |  | 3/6 – |
| $CCl_4$ group + SS-31 | 5/5 – | 5/5 – | 5/5 – |

Note:
"–" = No abnormal findings;
"±" = Minimal;
"+" = Slight;
"++" = Moderate;
"+++" = severe SS-31 protected renal tubules from $CCl_4$ nephrotoxicity. H&E staining revealed the $CCl_4$ treatment resulted in tubular epithelial cell degeneration and necrosis (FIG. 31a); in contrast, the renal histology of SS-31 treated animals (FIG. 31b) showed no observable histopathological change, and it was almost identical to the naïve control animal (FIG. 31c).

Thus, the results from the above example demonstrated the usefulness of the aromatic-cationic peptides of the invention in protecting a subject from chronic kidney injury caused by $CCl_4$ nephrotoxicity.

Example 7

Prevention of ARI caused by Cisplatin

The effects of the aromatic-cationic peptides of the invention in protecting a subject from cisplatin-induced ARI were investigated in an animal model of ARI caused by cisplatin.

Sprague-Dawley rats (350-400 g) were given a single dose of cisplatin (7 mg/kg) intraperitoneally on Day 1. One group of rats (n=8) received one dose of SS-31 (3 mg/kg) subcutaneously just prior to cisplatin administration, and repeated once daily for 3 more days. A second group of rats (n=8) A second group of rats (n=8) received an equal volume of saline on the day of cisplatin administration and for 3 more days after.

Experimental Protocol: Rats had free access to tap water and standard rat chow prior to cisplatin administration. Control blood samples were obtained from the tail vein before cisplatin administration. Saline or SS-31 (dissolved in saline) was administered to the rats subcutaneously prior to cisplatin injection. Cisplatin (dissolved in saline) was administered at a dose of 7 mg/kg intraperitoneally. All rats then received either saline or SS-31 (3 mg/kg) daily for 3 days. Rat were placed in metabolic cages for the last 24 hours for urine collection. At the end of this period, a blood sample was withdrawn from the tail vein. After this, the animals were anesthetized, kidneys were removed, and the animals euthanized.

Renal function: Renal function was assessed by blood urea nitrogen (BUN), serum creatinine, urine creatinine, and urine protein (Beckman ALX Chemical Analyzer). GFR was estimated from creatinine clearance which was determined from urinary creatinine, urine flow rate, and serum creatinine.

Renal Histology: Kidneys were fixed in 10% neutral-buffered formalin and embedded in paraffin wax. Three micron sections were stained with periodic acid-Schiff (PAS) and analyzed by light microscopy.

Results: In accordance with the procedures just described, the effects of the aromatic-cationic peptides of the invention in protecting a subject from cisplatin nephrotoxicity were investigated in an animal model of ARI caused by cisplatin administration. Between group comparisons were determined using the Student's t-test.

Figure 32B:
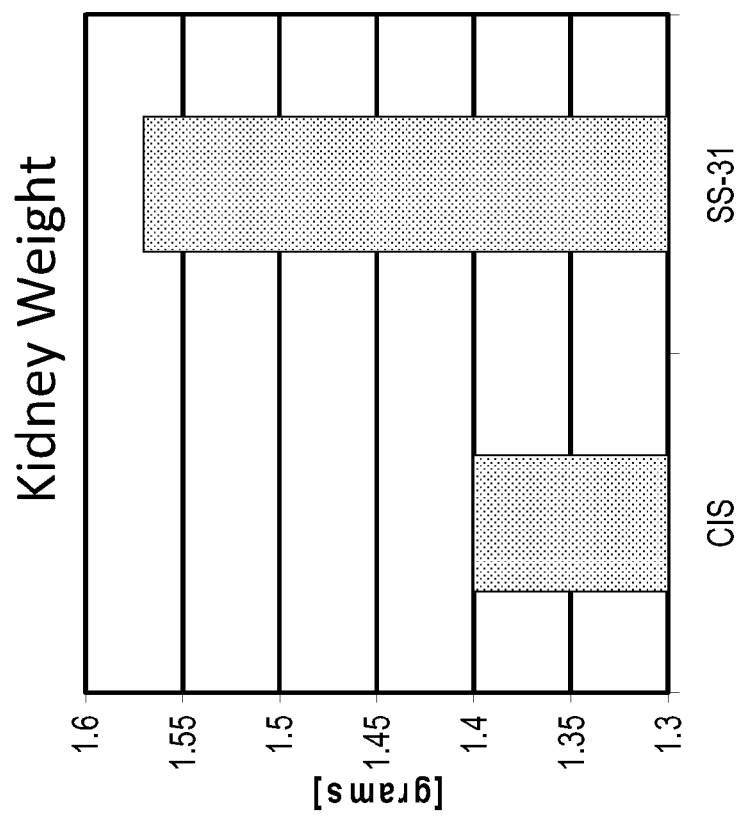
FIG. 32 is a series of charts showing the effects of the aromatic-cationic peptides of the invention on total body weight (FIG. 32a), kidney weight (FIG. 32b), serum creatinine (FIG. 32c), BUN (FIG. 32d), and creatinine clearance (FIG. 32e) in rats administered the nephrotoxic agent cisplatin.
Figure 32A:
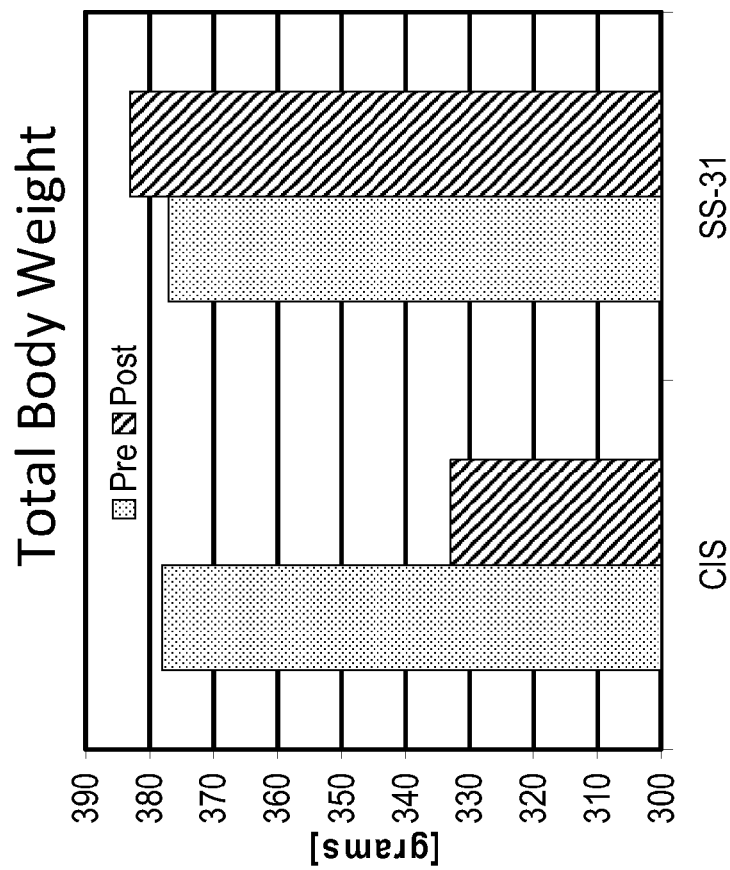

In the saline treated rats, there was a significant reduction in body weight 3 days after cisplatin administration (333±12.6 g) when compared to body weight before cisplatin administration (378.4±8.2 g) (p<0.0001) (FIG. 32a). Body weight in the SS-31 treatment group was similar to saline group before cisplatin treatment (376.9±5.2 g; p=0.673), and body weight did not change 3 days after cisplatin treatment (384±28 g; p=0.46). There was a significant difference in the effect of cisplatin treatment on body weight in the SS-31 treatment group compared to saline (p=0.004). Kidney weight was also higher in the SS-31 treated group (1.6±0.2 g) compared to the saline treated group (1.4±0.2 g) (p=0.036) (FIG. 32b).

Figure 32E:
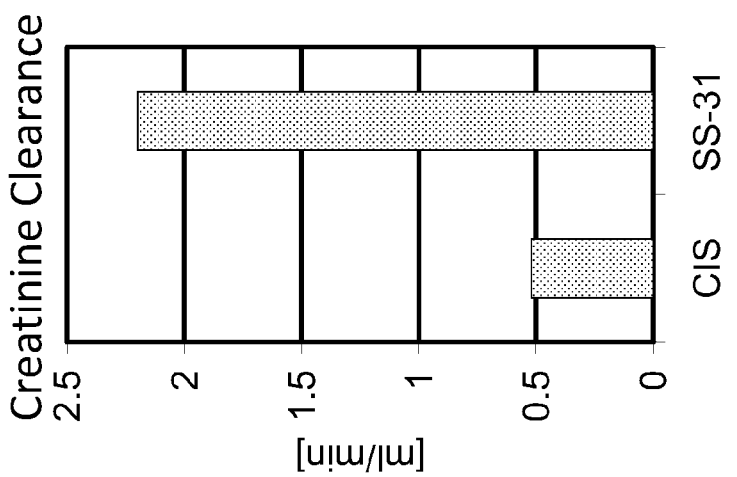
Figure 32D:
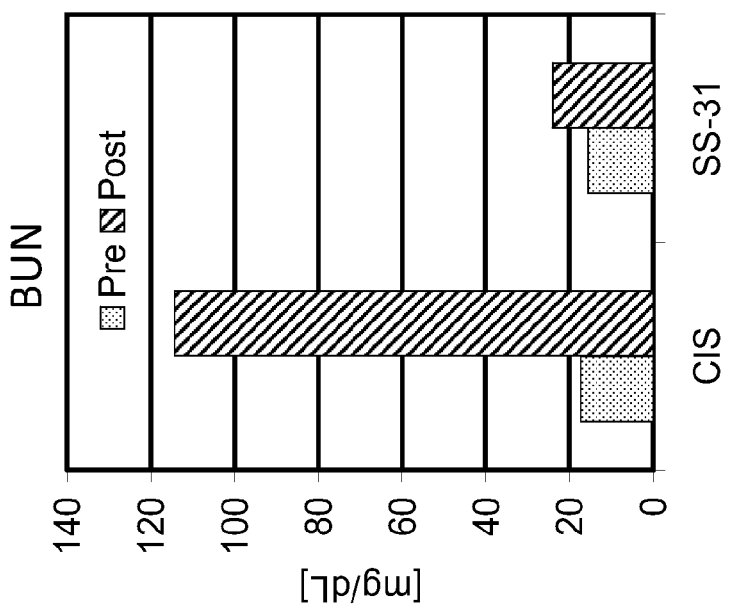
Figure 32C:
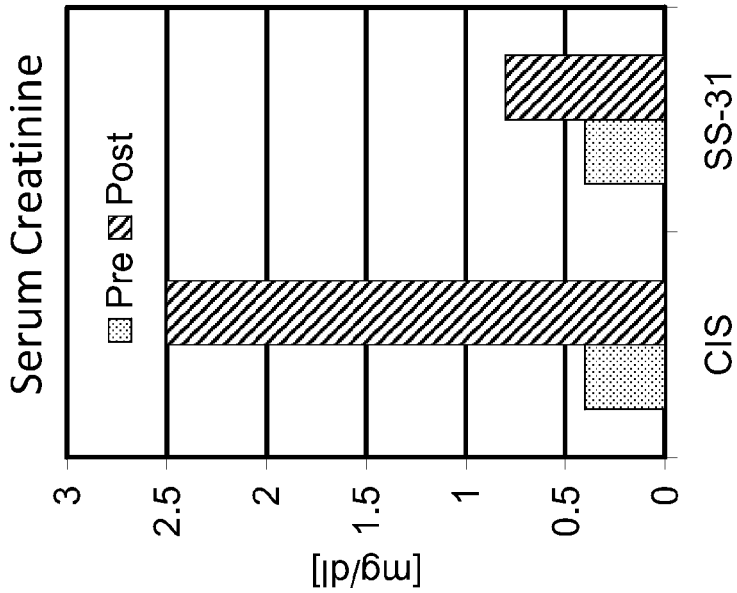

In the saline treated rats, serum creatinine increased from 0.4±0.09 mg/dl to 2.5±2.8 mg/dl) 3 days after cisplatin treatment (p=0.065) (FIG. 32c). In contrast, serum creatinine only increased from 0.4±0.09 mg/dl to 0.8±0.73 mg/dl in the SS-31 treatment group. The variation among rats was too large to reach statistical significance. However, 5 out of 8 rats that received SS-31 had no change in serum creatinine (<0.4 mg/dl), whereas only one out of 8 saline rats had serum creatinine less than 1.0 mg/dl. Creatinine clearance was significantly higher in the SS-31 treated rats 3 days after cisplatin treatment (2.2±1.3 ml/min) compared to the saline group (0.5±0.6 ml/min) (p=0.024) (FIG. 32e).

In the saline treated rats, BUN increased from 17.3±1.5 mg/dl to 114.4±105 mg/dl) 3 days after cisplatin treatment (p=0.035) (FIG. 32d). In contrast, BUN only increased from 15.5±1.7 mg/dl to 29.3±25 mg/dl in the SS-31 treatment group (p=0.167). BUN was significantly lower in the SS-31 treated group 3 days after cisplatin treatment (p=0.042).

In summary, SS-31 protected kidneys from damage caused by cisplatin. As such, the aromatic-cationic peptides of the invention are useful in methods of protecting a subject from acute renal injury caused by nephrotoxic agents.

Example 8

Protection and Treatment of ALF by Aromatic-Cationic Peptides

To demonstrate the effects on prevention and/or treatment of ALF, the aromatic-cationic peptides of the invention are tested on animal models of ALF. Suitable animal models induce ALF in experimental animals using surgical procedures, toxic liver injury, or a combination of both (See Belanger and Butterworth, "Acute Liver Failure: A Critical Appraisal of Available Animal Models." *Metabolic Brain Disease*, 20:409-423 (2005)).

To test the effect of the aromatic-cationic peptides of the invention on the prevention of ALF, the peptides are administered prior to or simultaneously with the drug or surgical insult. A comparison of hepatic function following the insult is made between subjects who received the peptides and those subjects who did not receive the peptides. Hepatic function is assessed using one or more indicators such as levels of serum hepatic enzymes (transaminases, alkaline phosphatase), serum bilirubin, serum ammonia, serum glucose, serum lactate, or serum creatinine Efficacy of the aromatic-cationic peptides of the invention in preventing ALF is indicated by a reduction in the occurrence or severity of the ALF (indicated by the markers above) as compared to control subjects.

To test the effect of the aromatic-cationic peptides of the invention on the treatment of ALF, the peptides are administered following the drug or surgical insult used to induce the ALF in the animal model. Following a course of treatment (ranging from several hours to several days), a comparison of hepatic function is made between subjects who received the peptides and those subjects which did not receive the peptides. Hepatic function is assessed using one or more indicators such as levels of serum hepatic enzymes (transaminases, alkaline phosphatase), serum bilirubin, serum ammonia, serum glucose, serum lactate, or serum creatinine Efficacy of the aromatic-cationic peptides of the invention in treating ALF is indicated by a reduction in one or more signs or symptoms of ALF (indicated by the markers above) as compared to control subjects.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and compositions within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Other embodiments are set forth within the following claims.

What is claimed is:

1. A method for treating contrast-induced nephropathy in a subject in need thereof, the method comprising administering to the subject an effective amount of a peptide selected from the group-consisting of Phe-D-Arg-Phe-Lys-NH$_2$ (SS-20) and D-Arg-2'6'Dmt-Lys-Phe-NH$_2$ (SS-31).

2. The method of claim 1, wherein the contrast-induced nephropathy comprises an inflammatory response.

3. The method of claim 1, wherein the contrast-induced nephropathy comprises a decrease in glomerular filtration rate (GFR) compared to a healthy control subject.

4. The method of claim 1, wherein the contrast-induced nephropathy comprises a decrease in urinary output compared to a healthy control subject.

5. The method of claim 1, wherein the contrast-induced nephropathy comprises an increase in renal tubular apoptosis compared to a healthy control subject.

6. The method of claim 1, wherein the contrast-induced nephropathy comprises loss of renal tubular brush border and/or renal vacuolization.

7. The method of claim 1, wherein the contrast-induced nephropathy comprises increased serum Cystatin C levels and/or serum creatinine levels compared to a healthy control subject.

8. The method of claim 1, wherein the contrast-induced nephropathy comprises proteinuria and/or increased urinary creatinine compared to a healthy control subject.

* * * * *